(12) United States Patent
Jayasinghe et al.

(10) Patent No.: US 12,644,879 B2

(45) Date of Patent: *Jun. 2, 2026

(54) METHOD OF NANOPORE SEQUENCING

(71) Applicant: Oxford Nanopore Technologies PLC, Oxford (GB)

(72) Inventors: Lakmal Jayasinghe, Oxford (GB); John Joseph Kilgour, Oxford (GB); Neil Roger Wood, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 1027 days.

This patent is subject to a terminal disclaimer.

(21) Appl. No.: 17/693,922

(22) Filed: Mar. 14, 2022

(65) Prior Publication Data

US 2022/0283141 A1    Sep. 8, 2022

Related U.S. Application Data

(63) Continuation of application No. 15/551,884, filed as application No. PCT/GB2016/050391 on Feb. 17, 2016, now Pat. No. 11,307,192.

(30) Foreign Application Priority Data

Feb. 19, 2015    (GB) ..................................... 1502810

(51) Int. Cl.

| | |
|---|---|
| *G01N 33/487* | (2006.01) |
| *B82B 3/00* | (2006.01) |
| *C12Q 1/6869* | (2018.01) |
| *G16B 30/00* | (2019.01) |

(52) U.S. Cl.
CPC ......... *G01N 33/48721* (2013.01); *B82B 3/00* (2013.01); *C12Q 1/6869* (2013.01); *G16B 30/00* (2019.02); *C12Q 2565/631* (2013.01)

(58) Field of Classification Search
CPC ................................ C12Q 1/68; C12Q 1/6869
See application file for complete search history.

(56) References Cited

U.S. PATENT DOCUMENTS

| | | | |
|---|---|---|---|
| 5,795,782 | A | 8/1998 | Church et al. |
| 6,015,714 | A | 1/2000 | Baldarelli et al. |
| 6,114,121 | A | 9/2000 | Fujiwara et al. |
| 6,150,112 | A | 11/2000 | Weissman et al. |
| 6,362,002 | B1 | 3/2002 | Denison et al. |
| 6,426,231 | B1 | 7/2002 | Bayley et al. |
| 6,627,067 | B1 | 9/2003 | Branton et al. |
| 6,824,659 | B2 | 11/2004 | Bayley et al. |
| 6,863,833 | B1 | 3/2005 | Bloom et al. |
| 6,916,665 | B2 | 7/2005 | Bayley et al. |
| 6,927,070 | B1 | 8/2005 | Bayley et al. |
| 7,189,503 | B2 | 3/2007 | Akeson et al. |
| 8,105,846 | B2 | 1/2012 | Bayley et al. |
| 8,785,211 | B2 | 7/2014 | Bayley et al. |

| | | | | |
|---|---|---|---|---|
| 8,822,160 | B2 | 9/2014 | Bayley et al. | |
| 8,828,208 | B2 | 9/2014 | Canas et al. | |
| 9,073,990 | B2 | 7/2015 | Paas et al. | |
| 9,127,313 | B2 | 9/2015 | Brown et al. | |
| 9,222,082 | B2 | 12/2015 | Jayasinghe et al. | |
| 9,447,152 | B2 | 9/2016 | Clarke et al. | |
| 9,562,887 | B2 | 2/2017 | Maglia et al. | |
| 9,580,480 | B2 | 2/2017 | Lu et al. | |
| 9,588,079 | B2 | 3/2017 | Gundlach et al. | |
| 9,732,381 | B2 | 8/2017 | Stoddart et al. | |
| 9,751,915 | B2 | 9/2017 | Clarke et al. | |
| 9,777,049 | B2 * | 10/2017 | Bruce ................... | G01N 27/447 |
| 9,797,009 | B2 * | 10/2017 | Heron ................... | C12Q 1/6869 |
| 9,885,078 | B2 * | 2/2018 | Jayasinghe ............ | C07K 14/31 |
| 10,006,905 | B2 * | 6/2018 | Maglia ................. | C12Q 1/6869 |
| 10,167,503 | B2 | 1/2019 | Clarke et al. | |
| 10,266,885 | B2 | 4/2019 | Jayasinghe et al. | |
| 10,385,389 | B2 | 8/2019 | Heron et al. | |
| 10,400,014 | B2 | 9/2019 | Howorka et al. | |
| 10,443,097 | B2 | 10/2019 | Jayasinghe et al. | |
| 10,472,673 | B2 | 11/2019 | Maglia et al. | |
| 10,514,378 | B2 | 12/2019 | Maglia et al. | |
| 10,669,581 | B2 | 6/2020 | Stoddart et al. | |
| 10,802,015 | B2 | 10/2020 | Maglia et al. | |
| 10,844,432 | B2 | 11/2020 | Jayasinghe et al. | |
| 10,882,889 | B2 | 1/2021 | Bruce et al. | |
| 10,975,428 | B2 | 4/2021 | Jayasinghe et al. | |
| 10,976,300 | B2 | 4/2021 | Maglia et al. | |
| 10,976,311 | B2 | 4/2021 | Maglia et al. | |
| 10,995,372 | B2 | 5/2021 | Jayasinghe et al. | |
| 11,034,734 | B2 | 6/2021 | Howorka et al. | |

(Continued)

FOREIGN PATENT DOCUMENTS

| | | |
|---|---|---|
| CA | 2381139 A1 | 3/2001 |
| CN | 102116783 A | 7/2011 |

(Continued)

OTHER PUBLICATIONS

Dekker C, Solid-state nanopores. Nature nanotechnology 2:209-215 (Year: 2007).*

International Search Report and Written Opinion for Application No. PCT/GB2016/050391, mailed Jun. 15, 2016.

International Preliminary Report on Patentability for Application No. PCT/GB2016/050391, mailed Aug. 31, 2017.

[No Author Listed] EBI Accession No. A0A085GH19. Oct. 29, 2014.

[No Author Listed] EBI Accession No. A0A0DILDB9. Apr. 29, 2015.

[No Author Listed] EBI Accession No. EMBLCDS:ABV05494. Sep. 11, 2007 .

(Continued)

*Primary Examiner* — Ethan C Whisenant

(74) *Attorney, Agent, or Firm* — Wolf, Greenfield & Sacks, P.C.

(57) ABSTRACT

The invention relates to a novel method of producing hetero-oligomeric pores. The invention also relates to hetero-oligomeric pores produced using the method and polynucleotide characterisation using the hetero-oligomeric pores.

11 Claims, 3 Drawing Sheets

Specification includes a Sequence Listing.

(56) References Cited

U.S. PATENT DOCUMENTS

| | | | |
|---|---|---|---|
| 11,104,709 B2 | 8/2021 | Maglia et al. | |
| 11,169,138 B2 | 11/2021 | Maglia et al. | |
| 11,186,868 B2 * | 11/2021 | Jayasinghe | G01N 33/48721 |
| 11,307,192 B2 * | 4/2022 | Jayasinghe | C12Q 1/6869 |
| 11,725,235 B2 | 8/2023 | Heron et al. | |
| 11,739,377 B2 | 8/2023 | Jayasinghe et al. | |
| 11,761,956 B2 | 9/2023 | Maglia et al. | |
| 11,845,780 B2 | 12/2023 | Bruce et al. | |
| 11,939,359 B2 | 3/2024 | Jayasinghe et al. | |
| 11,965,183 B2 * | 4/2024 | Heron | C12Q 1/68 |
| 12,173,364 B2 | 12/2024 | Stoddart et al. | |
| 12,227,800 B2 | 2/2025 | Jayasinghe et al. | |
| 12,258,375 B2 | 3/2025 | Bruce et al. | |
| 12,371,458 B2 | 7/2025 | Maglia et al. | |
| 2001/0044137 A1 | 11/2001 | Heyman et al. | |
| 2002/0028458 A1 | 3/2002 | Lexow | |
| 2002/0094526 A1 | 7/2002 | Bayley et al. | |
| 2002/0197614 A1 | 12/2002 | Mosaic | |
| 2003/0044816 A1 | 3/2003 | Denison et al. | |
| 2003/0099951 A1 | 5/2003 | Akeson et al. | |
| 2003/0165936 A1 | 9/2003 | Rabbani et al. | |
| 2003/0211502 A1 | 11/2003 | Sauer et al. | |
| 2003/0215881 A1 | 11/2003 | Bayley et al. | |
| 2004/0209299 A1 | 10/2004 | Pinter et al. | |
| 2004/0214177 A1 | 10/2004 | Bension | |
| 2005/0053961 A1 | 3/2005 | Akeson et al. | |
| 2006/0063171 A1 | 3/2006 | Akeson et al. | |
| 2006/0105461 A1 | 5/2006 | Tom-Moy et al. | |
| 2007/0218471 A1 | 9/2007 | Kim et al. | |
| 2008/0121534 A1 | 5/2008 | White et al. | |
| 2008/0311582 A1 | 12/2008 | Bayley et al. | |
| 2009/0111115 A1 | 4/2009 | Drmanac et al. | |
| 2009/0256116 A1 | 10/2009 | Shumaker-Parry et al. | |
| 2009/0283412 A1 | 11/2009 | Sansinena et al. | |
| 2009/0298075 A1 | 12/2009 | Travers et al. | |
| 2009/0298188 A1 | 12/2009 | Peti-Peterdi | |
| 2010/0120098 A1 | 5/2010 | Grunenwald et al. | |
| 2010/0196203 A1 | 8/2010 | Sanghera et al. | |
| 2010/0297638 A1 | 11/2010 | Bayley et al. | |
| 2011/0053284 A1 * | 3/2011 | Meller | G01N 33/48721 |
| | | | 506/13 |
| 2011/0120871 A1 | 5/2011 | Reid et al. | |
| 2011/0121840 A1 | 5/2011 | Sanghera et al. | |
| 2011/0177498 A1 | 7/2011 | Clarke et al. | |
| 2011/0229877 A1 | 9/2011 | Jayasinghe et al. | |
| 2011/0311965 A1 | 12/2011 | Maglia et al. | |
| 2012/0055792 A1 * | 3/2012 | Gundlach | G01N 27/44704 |
| | | | 204/600 |
| 2012/0058468 A1 | 3/2012 | Mckeown | |
| 2012/0064599 A1 | 3/2012 | Jayasinghe et al. | |
| 2012/0100530 A1 | 4/2012 | Moysey et al. | |
| 2012/0107802 A1 | 5/2012 | Stoddart et al. | |
| 2012/0219960 A1 * | 8/2012 | Bayley | C12Q 1/6869 |
| | | | 435/6.19 |
| 2012/0322679 A1 | 12/2012 | Brown et al. | |
| 2014/0051069 A1 | 2/2014 | Jayasinghe et al. | |
| 2014/0186823 A1 | 7/2014 | Clarke et al. | |
| 2014/0194324 A1 | 7/2014 | Gormley et al. | |
| 2014/0262784 A1 | 9/2014 | Clarke et al. | |
| 2014/0296083 A1 | 10/2014 | Brown et al. | |
| 2015/0008126 A1 | 1/2015 | Maglia et al. | |
| 2015/0011398 A1 | 1/2015 | Lewis et al. | |
| 2015/0031020 A1 | 1/2015 | Jayasinghe et al. | |
| 2015/0068904 A1 | 3/2015 | Bruce et al. | |
| 2015/0152495 A1 | 6/2015 | Stava et al. | |
| 2015/0175663 A1 | 6/2015 | Yokoi et al. | |
| 2015/0177237 A1 | 6/2015 | Turner et al. | |
| 2015/0191709 A1 | 7/2015 | Heron et al. | |
| 2015/0218629 A1 | 8/2015 | Heron et al. | |
| 2015/0346149 A1 | 12/2015 | Brown et al. | |
| 2016/0010147 A1 | 1/2016 | Heron et al. | |
| 2016/0053300 A1 | 2/2016 | Maglia et al. | |
| 2016/0370358 A1 | 12/2016 | Maglia et al. | |
| 2017/0029475 A1 * | 2/2017 | Niederweis | C12Q 1/6869 |
| 2017/0058337 A1 | 3/2017 | Clarke et al. | |

| | | | |
|---|---|---|---|
| 2017/0058338 A1 | 3/2017 | Jayasinghe et al. | |
| 2017/0107569 A1 | 4/2017 | Heron et al. | |
| 2017/0233803 A1 | 8/2017 | Stoddart et al. | |
| 2017/0306398 A1 | 10/2017 | Jayasinghe et al. | |
| 2018/0030526 A1 | 2/2018 | Brown et al. | |
| 2018/0095066 A1 | 4/2018 | Jayasinghe et al. | |
| 2018/0148481 A2 | 5/2018 | Howorka et al. | |
| 2018/0208632 A1 | 7/2018 | Bruce et al. | |
| 2018/0209952 A1 | 7/2018 | Maglia et al. | |
| 2018/0334707 A1 | 11/2018 | Stoddart et al. | |
| 2018/0335425 A1 | 11/2018 | Maglia et al. | |
| 2018/0364214 A1 | 12/2018 | Maglia et al. | |
| 2019/0071721 A1 | 3/2019 | Jayasinghe et al. | |
| 2019/0202876 A1 | 7/2019 | Jayasinghe et al. | |
| 2019/0300582 A1 | 10/2019 | Jayasinghe et al. | |
| 2019/0330282 A1 | 10/2019 | Jayasinghe et al. | |
| 2019/0346431 A1 | 11/2019 | Maglia et al. | |
| 2020/0017556 A1 | 1/2020 | Howorka et al. | |
| 2020/0072824 A1 | 3/2020 | Maglia et al. | |
| 2020/0087724 A1 | 3/2020 | Heron et al. | |
| 2020/0224262 A1 | 7/2020 | Jayasinghe et al. | |
| 2020/0299336 A9 | 9/2020 | Jayasinghe et al. | |
| 2020/0299337 A9 | 9/2020 | Jayasinghe et al. | |
| 2020/0407785 A1 | 12/2020 | Stoddart et al. | |
| 2021/0139972 A1 | 5/2021 | Jayasinghe et al. | |
| 2021/0147486 A1 | 5/2021 | Remaut et al. | |
| 2021/0269872 A1 | 9/2021 | Jayasinghe et al. | |
| 2021/0284696 A1 | 9/2021 | Remaut et al. | |
| 2021/0292376 A1 | 9/2021 | Howorka et al. | |
| 2021/0317520 A1 | 10/2021 | Jayasinghe et al. | |
| 2021/0324020 A1 | 10/2021 | Bruce et al. | |
| 2021/0395811 A1 | 12/2021 | Garalde et al. | |
| 2021/0405039 A1 | 12/2021 | Maglia et al. | |
| 2022/0024985 A9 | 1/2022 | Remaut et al. | |
| 2022/0056517 A1 | 2/2022 | Remaut et al. | |
| 2022/0064230 A1 | 3/2022 | Jayasinghe et al. | |
| 2022/0091096 A1 | 3/2022 | Maglia et al. | |
| 2022/0119879 A1 | 4/2022 | Jayasinghe et al. | |
| 2024/0026441 A1 | 1/2024 | Heron et al. | |
| 2024/0044881 A1 | 2/2024 | Maglia et al. | |
| 2024/0060126 A1 | 2/2024 | Jayasinghe et al. | |
| 2024/0199711 A1 | 6/2024 | Bruce et al. | |
| 2024/0254172 A1 | 8/2024 | Maglia et al. | |
| 2024/0345073 A9 | 10/2024 | Maglia et al. | |
| 2025/0215490 A1 | 7/2025 | Stoddart et al. | |

FOREIGN PATENT DOCUMENTS

| | | |
|---|---|---|
| CN | 102174554 A | 9/2011 |
| CN | 102317310 A | 1/2012 |
| CN | 103460040 A | 12/2013 |
| EP | 2194123 B1 | 8/2012 |
| EP | 2682460 | 1/2014 |
| GB | 2453377 | 4/2009 |
| GB | 1314695.6 | 8/2013 |
| JP | H10-146190 | 6/1998 |
| JP | 2005-253427 | 9/2005 |
| JP | 2015-514128 A | 5/2015 |
| WO | WO 1999/005167 | 2/1999 |
| WO | WO 2000/028312 A1 | 5/2000 |
| WO | WO 2001/042782 | 6/2001 |
| WO | WO 2001/059453 | 8/2001 |
| WO | WO 2002/042496 | 5/2002 |
| WO | WO 2003/095669 | 11/2003 |
| WO | WO 2005/013666 A2 | 2/2005 |
| WO | WO 2005/076010 A2 | 8/2005 |
| WO | WO 2006/028508 | 3/2006 |
| WO | WO 2006/100484 | 9/2006 |
| WO | WO 2007/057668 | 5/2007 |
| WO | WO 2007/075987 | 7/2007 |
| WO | WO 2007/084103 | 7/2007 |
| WO | WO 2008/102120 | 8/2008 |
| WO | WO 2008/102121 | 8/2008 |
| WO | WO 2008/124107 | 10/2008 |
| WO | WO 2009/020682 A2 | 2/2009 |
| WO | WO 2009/024775 A1 | 2/2009 |
| WO | WO 2009/035647 | 3/2009 |
| WO | WO 2009/044170 A1 | 4/2009 |
| WO | WO 2009/077734 A2 | 6/2009 |

(56) References Cited

FOREIGN PATENT DOCUMENTS

| WO | WO 2009/143425 A1 | 11/2009 |
|----|-------------------|---------|
| WO | WO 2010/004265 A1 | 1/2010 |
| WO | WO 2010/004273 A1 | 1/2010 |
| WO | WO 2010/034018 | 3/2010 |
| WO | WO 2010/055307 A1 | 5/2010 |
| WO | WO 2010/086602 A1 | 8/2010 |
| WO | WO 2010/086603 A1 | 8/2010 |
| WO | WO 2010/086622 A1 | 8/2010 |
| WO | WO 2010/122293 A1 | 10/2010 |
| WO | WO 2011/067559 A1 | 6/2011 |
| WO | WO 2012/005857 A1 | 1/2012 |
| WO | WO 2012/042226 A1 | 4/2012 |
| WO | WO 2012/107778 A2 | 8/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A1 | 4/2013 |
| WO | WO 2013/098561 A1 | 7/2013 |
| WO | WO 2013/098562 A1 | 7/2013 |
| WO | WO 2013/109970 A1 | 7/2013 |
| WO | WO 2013/153359 A1 | 10/2013 |
| WO | WO 2016/166232 A1 | 10/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A1 | 5/2014 |
| WO | WO 2014/064444 A1 | 5/2014 |
| WO | WO 2014/122654 A2 | 8/2014 |
| WO | WO 2014/135838 A1 | 9/2014 |
| WO | WO 2014/142850 A1 | 9/2014 |
| WO | WO 2014/153047 A1 | 9/2014 |
| WO | WO 2014/153625 A1 | 10/2014 |
| WO | WO 2014/187924 A1 | 11/2014 |
| WO | WO 2015/022544 A1 | 2/2015 |
| WO | WO 2015/051378 A1 | 4/2015 |
| WO | WO 2015/055981 A1 | 4/2015 |
| WO | WO 2015/110777 A1 | 7/2015 |
| WO | WO 2015/124935 A1 | 8/2015 |
| WO | WO 2015/150786 A1 | 10/2015 |
| WO | WO 2015/150787 A1 | 10/2015 |
| WO | WO 2015/166275 A1 | 11/2015 |
| WO | WO 2015/166276 A1 | 11/2015 |
| WO | WO 2016/034591 A2 | 3/2016 |
| WO | WO 2016/055778 A1 | 4/2016 |
| WO | WO 2017/149316 A1 | 9/2017 |
| WO | WO 2017/149317 A1 | 9/2017 |
| WO | WO 2017/149318 A1 | 9/2017 |
| WO | WO 2018/211241 A1 | 11/2018 |

OTHER PUBLICATIONS

[No Author Listed] Enterobacteria phage vB_EcoM-ACG-C40, complete genome. Genbank Acc. No. NC 019399.1. 2 pages. [97 pages in 70046US02].

[No Author Listed] Helicos BioSciences Corporation, "Helicos Genetic Analysis System," Specification Sheet retrieved online at: www.helicosbio.com/Portals/O/Documents/Helicos_SalesSpec.pdf, 4 pages (2008).

[No Author Listed] Nextera™ DNA Sample Preparation Kits (Illumina) Oct. 2011. (2 pages).

[No Author Listed] Oxford Nanopore "Product" brochure (2020) https://nanoporetech.com/sites/default/files/s3/literature/product-brochure.Pdf (36 pages).

[No Author Listed] Uniprot Accession No. A0A081NL13. Oct. 29, 2014. 4 pages.

[No Author Listed] Uniprot Accession No. AOAOP7DN88. Jan. 20, 2016. 3 pages.

[No Author Listed] Uniprot Accession No. Q8Z727. Oct. 24, 2003. 4 pages.

[No Author Listed] UniProt, "SubName: Full=Curli production assembly/transport component {ECO:0000313:EMBL:CTR43957.1};", XP002783536, retrieved from EBI accession No. UNIPROT:A0A0K3UZP3, Nov. 11, 2015.

[No Author Listed], *Escherichia coli* HS curli production assembly/transport subunit. Accession No. ABV05494. Sep. 11, 2007. 2 pages.

Afonine et al., Real-space refinement in PHENIX for cryo-EM and crystallography. Acta Crystallogr D Struct Biol. 2018;74(Pt 6):531-544. doi:10.1107/S2059798318006551.

Ahern, Biochemical, reagents kits offer scientists good return on investment. The Scientist. Jul. 24, 1995;9(15):20.

Altschul et al. Basic local alignment search tool. J Mol Biol. Oct. 5, 1990;215(3):403-10. doi: 10.1016/S0022-2836(05)80360-2.

Altschul, A protein alignment scoring system sensitive at all evolutionary distances. J Mol Evol. Mar. 1993;36(3):290-300. doi: 10.1007/BF00160485.

Aoki et al., Single channel properties of lysenin measured in artificial lipid bilayers and their applications to biomolecule detection. Proc Jpn Acad Ser B Phys Biol Sci. 2010;86(9):920-5.

Aravind et al., The DNA-Repair Protein AlkB, EGL-9, and Leprecan Define New Families of 2-oxoglutarate-andIron-Dependent Dioxygenases. Genome Biology. 2001;2:1-8.

Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.

Ashton et al., MinION Nanopore Sequencing Identifies the Position and Structure of a Bacterial antibiotic Resistance Island. Nat Biotechnol. Mar. 2015;33(3):296-302.

Astier et al., Stochastic detection of motor protein-RNA complexes by single-channel current recording. Chemphyschem. Oct. 22, 2007;8(15):2189-94.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Atkins et al., Structure-function relationships of a novel bacterial toxin, hemolysin E. The role of alpha G. J Biol Chem. Dec. 29, 2000;275(52):41150-5.

Ayub et al., Engineered transmembrane pores. Curr Opin Chem Biol. 2016;34:117-126. doi:10.1016/j.cbpa.2016.08.005. Author Manuscript, 16 pages.

Bayley, Membrane-protein structure: Piercing insights. Nature. Jun. 4, 2009;459(7247):651-2. doi: 10.1038/459651a.

Bayley, Nanopore Sequencing: From Imagination to Reality. Clin Chem. 2015;61(1):25-31.

Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.

Bezrukov et al., Counting Polymers Moving Through a Single Ion Channel. Nature. Jul. 28, 1994;370:279-81.

Bleijlevens et al., Changes in Protein Dynamics of the DNA Repair Dioxygenase AlkB Upon Binding of FE2+ and 2-Oxoglutarate. Biochemistry. Mar. 26, 2012;51:3334-41.

Bleijlevens et al., Dynamic States of the DNA Repair Enzyme AlkB regulate Product Release. Eur Mol Biol Org. Jul. 11, 2008;9(9):872-77.

Boersma et al., Continuous stochastic detection of amino acid enantiomers with a protein nanopore. Angew Chem Int Ed Engl. Sep. 17, 2012;51(38):9606-9. doi: 10.1002/anie.201205687. Epub Aug. 29, 2012.

Bourdon et al., Molecular cloning and sequence analysis of a chondroitin sulfate proteoglycan cDNA. Proc Natl Acad Sci U S A. Mar. 1985;82(5):1321-5.

Braha et al., Carriers versus adapters in stochastic sensing. Chemphyschem. May 2005;6(5):889-92.

Brown et al., Tools for macromolecular model building and refinement into electron cryo-microscopy reconstructions. Acta Crystallogr D Biol Crystallogr. 2015;71(Pt 1):136-153. doi:10.1107/S1399004714021683.

Burton et al., ClpX-mediated remodeling of mu transpososomes: selective unfolding of subunits destabilizes the entire complex. Mol Cell. Aug. 2001;8(2):449-54. doi: 10.1016/s1097-2765(01)00307-0.

(56)          References Cited

OTHER PUBLICATIONS

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Cao et al., Structure of the nonameric bacterial amyloid secretion channel. Proc Natl Acad Sci USA. Dec. 16, 2014;111(50):E5439-44. doi: 10.1073/pnas.1411942111. Epub Dec. 1, 2014.

Caruccio, Preparation of next-generation sequencing libraries using Nextera™ technology: simultaneous DNA fragmentation and adaptor tagging by in vitro transposition. Methods Mol Biol. 2011;733:241-55. doi: 10.1007/978-1-61779-089-8_17.

Chapman et al., Role of Escherichia coli curli operons in directing amyloid fiber formation. Science. 2002;295(5556):851-855. doi:10.1126/science.1067484. Author Manuscript, 9 pages.

Cheley et al., A genetically encoded pore for the stochastic detection of a protein kinase. Chembiochem. Dec. 2006;7(12):1923-7.

Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.

Cheng et al., Design and testing of aptamer-based electrochemical biosensors for proteins and small molecules. Bioelectrochemistry. Nov. 2009;77(1):1-12. doi: 10.1016/j.bioelechem.2009.04.007. Epub May 5, 2009.

Chin et al., Addition of a photocrosslinking amino acid to the genetic code of Escherichiacoli. Proc Natl Acad Sci U S A. Aug. 20, 2002;99(17):11020-4. doi: 10.1073/pnas.172226299. Epub Aug. 1, 2002.

Chin et al., The Metabolite alpha-Ketoglutarate Extends Lifespan by Inhibiting ATP Synthase and TOR. Nature. Jul. 19, 2014;510:397-401.

Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.

Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.

Comai et al., Protein engineering modulates the transport properties and ion selectivity of the pores formed by staphylococcal gamma-haemolysins in lipid membranes. Mol Microbiol. Jun. 2002;44(5):1251-67.

De Vlaminck et al., Mechanism of homology recognition in DNA recombination from dual-molecule experiments. Mol Cell. Jun. 8, 2012;46(5):616-24. doi: 10.1016/j.molcel.2012.03.029. Epub May 3, 2012.

Derrington et al., A Novel DNA Sensing Technique Using Nanopore MSPA. 54th Annual Meeting of the Biophysical Society, Poster 2182-Plat, 2 pages (2010).

Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.

Devereux et al., A comprehensive set of sequence analysis programs for the VAX. Nucleic Acids Res. Jan. 11, 1984;12(1 Pt 1):387-95. doi: 10.1093/nar/12.1part1.387.

Eid et al., Real-time DNA sequencing from single polymerase molecules. Science. Jan. 2, 2009;323(5910):133-8. doi:10.1126/science.1162986. Epub Nov. 20, 2008.

Eifier et al., Cytotoxin ClyA from Escherichia coli assembles to a 13-meric pore independent of its redox-state. EMBO J. Jun. 7, 2006;25(11):2652-61. doi: 10.1038/sj.emboj.7601130. Epub May 11, 2006.

Engelhardt et al., A tetrameric porin limits the cell wall permeability of Mycobacterium smegmatis. J Biol Chem. Oct. 4, 2002;277(40):37567-72. Epub Jul. 18, 2002.

Epstein, Assembly, Spatial Distribution, and Secretion Activity of the Curlin Secretion Lipoprotein, CsgG. Dissertation. The University of Michigan. 2008. 167 pages.

Ergel et al., Protein Dynamics Control the Progression and Efficiency of the Catalytic Reaction Cycle of the Escherichia coli DNA-Repair Enzyme AlkB. J Biol Chem. Oct. 24, 2014;289(43):29584-601.

Fahie et al., Resolved Single-Molecule Detection of Individual Species Within a Mixture of Anti-Biotin Antibodies Using an Engineered Monometric Nanopore. Am Chem Soc. Jan. 9, 2015;9(2):1089-98.

Fiume et al., Savant: genome browser for high-throughput sequencing data. Bioinformatics. Aug. 15, 2010;26(16):1938-44. doi: 10.1093/bioinformatics/btq332. Epub Jun. 20, 2010.

Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.

Flusberg et al., Direct detection of DNA methylation during single-molecule, real-time sequencing. Nat Methods. Jun. 2010;7(6):461-5. doi: 10.1038/nmeth.1459. Epub May 9, 2010.

Fologea et al., Potential analytical applications of lysenin channels for detection of multivalent ions. Anal Bioanal Chem. Oct. 2011;401(6):1871-9. doi:10.1007/s00216-011-5277-8. Epub Aug. 5, 2011.

Franceschini et al., A nanopore machine promotes the vectorial transport of DNA across membranes. Sep. 2013; Nat Commun. 2013;4:2415. doi: 10.1038/ncomms3415.

Franceschini et al., DNA Translocation through Nanopores at Physiological Ionic Strengths Requires Precise Nanoscale Engineering. ACS Nano. Sep. 27, 2016;10(9):8394-402. doi: 10.1021/acsnano.6b03159. Epub Aug. 15, 2016.

Freedman et al., Single Molecule Unfolding and Stretching of Protein Domains Inside a Solid-State Nanopore by Electric Field. Scientific Reports. Apr. 10, 2013;3(1638):1-8.

Galenkamp et al., Direct electrical quantification of glucose and asparagine from bodily fluids using nanopores. Nat Commun. 2018;9(1):4085. Published Oct. 5, 2018. doi:10.1038/s41467-018-06534-1.

Genschel et al., Interaction of E. coli single-stranded DNA binding protein (SSB) with exonuclease I. The carboxy-terminus of SSB is the recognition site for the nuclease. Biol Chem. Mar. 2000;381(3):183-92.

Gershow et al., Recapturing and trapping single molecules with a solid-state nanopore. Nat Nanotechnol. Dec. 2007;2(12):775-9. doi:10.1038/nnano.2007.381. Epub Dec. 2, 2007.

Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.

Gibson et al., AgfC and AgfE facilitate extracellular thin aggregative fimbriae synthesis in Salmonella enteritidis. Microbiology. Apr. 2007;153(Pt 4):1131-1140. doi: 10.1099/mic.0.2006/000935-0.

Gilbert et al., Two Structural Transitions in Membrane Pore Formation by Pneumolysin, the Pore-Forming Toxin of Streptococcus pneumoniae. Cell. May 28, 1999;97:647-655.

Goedhart et al., Quantitative co-expression of proteins at the single cell level—application to a multimeric FRET sensor. PLoS One. 2011;6(11):e27321. doi: 10.1371/journal.pone.0027321. Epub Nov. 17, 2011.

Goryshin et al., Tn5 in vitro transposition. J Biol Chem. Mar. 27, 1998;273(13):7367-74. doi: 10.1074/jbc.273.13.7367.

Gouridis et al., Conformational Dynamics in Substrate-Binding Domains Influences Transport in the ABC Importer GinPQ. Nat Stuct Mol Biol. Dec. 8, 2014;22(1):57-66.

Goyal et al., Crystallization and preliminary X-ray crystallographic analysis of the curli transporter CsgG. Acta Crystallographica Section F: Structural Biology and Crystallization Communications. Dec. 1, 2013;69(12):1349-53.

Goyal et al., Structural and mechanistic insights into the bacterial amyloid secretion channel CsgG. Nature. Dec. 11, 2014;516(7530):250-3 with Supplemental Information. doi: 10.1038/nature13768. Epub Sep. 14, 2014.

Goyal et al., Structural and mechanistic insights into the bacterial amyloid secretion channel CsgG. Nature. Dec. 11, 2014;516(7530):250-3. doi: 10.1038/nature13768. Epub Sep. 14, 2014.

(56)  References Cited

OTHER PUBLICATIONS

Gu et al., Interaction of the noncovalent molecular adapter, beta-cyclodextrin, with the staphylococcal alpha-hemolysin pore. Biophys J. Oct. 2000;79(4):1967-75.

Gu et al., Stochastic sensing of organic analytes by a pore-forming protein containing a molecular adapter. Nature. Apr. 22, 1999;398(6729):686-90.

Guasch et al., Detailed architecture of a DNA translocating machine: the high-resolution structure of the bacteriophage phi29 connector particle. J Mol Biol. Jan. 25, 2002;315(4):663-76.

Guo et al., Nanopore sensor for copper ion detection using a polyamine decorated β-cyclodextrin as the recognition element. RSC Adv. 2017;7:15315. doi: 10.1039/c7ra00454k. 6 pages.

Hall et al., Hybrid pore formation by directed insertion of α-haemolysin into solid-state nanopores. Nat Nanotechnol. Dec. 2010;5(12):874-7. doi: 10.1038/nnano.2010.237. Epub Nov. 28, 2010.

Hammar et al., Expression of two csg operons is required for production of fibronectin- and congo red-binding curli polymers in *Escherichia coli* K-12. Mol Microbiol. Nov. 1995;18(4):661-70. doi: 10.1111/j.1365-2958.1995.mmi_18040661.x.

Haque et al., DNA-associated click chemistry. Science China Chemistry. Feb. 2014;57(2):215-231. doi:10.1007/s11426-013-5035-1.

Haque et al., Solid-State and Biological Nanopore for Real-Time Sensing of Single Chemical and Sequencing of DNA. Nano Today. Feb. 2013;8(1):56-74.

Heng et al., Sizing DNA using a nanometer-diameter pore. Biophys J. Oct. 2004;87(4):2905-11. doi: 10.1529/biophysj.104.041814. Epub Aug. 23, 2004.

Henrickson et al., Driven DNA transport into an asymmetric nanometer-scale pore. Phys Rev Lett. Oct. 2, 2000;85(14):3057-60.

Higgins et al., DNA-joining enzymes: a review. Methods Enzymol. 1979;68:50-71. doi: 10.1016/0076-6879(79)68006-0.

Holden et al., Direct introduction of single protein channels and pores into lipid bilayers. J Am Chem Soc. May 11, 2005;127(18):6502-3.

Holden et al., Functional bionetworks from nanoliter water droplets. J Am Chem Soc. Jul. 11, 2007;129(27):8650-5. Epub Jun. 16, 2007.

Hornblower et al., Single-molecule analysis of DNA-protein complexes using nanopores. Nat Methods. Apr. 2007;4(4):315-7. Epub Mar. 4, 2007.

Howorka et al., DNA Duplex Formation of Individual DNA Strands within a Single Protein Pore. Biophysical Journal, vol. 82{1, pt. 2):508a, No. 2482-Plat (2002).

Howorka et al., Kinetics of duplex formation for individual DNA strands within a single protein nanopore. Proc Natl Acad Sci U S A. Nov. 6, 2001;98(23):12996-3001. Epub Oct. 23, 2001.

Howorka et al., Nanopore Analytics: Sensing of Single Molecules. The Royal Society of Chemistry. Jun. 15, 2009;38:2360-84.

Howorka et al., Nanopores as protein sensors. Nat Biotechnol. Jun. 7, 2012;30(6):506-7. doi: 10.1038/nbt.2264.

Howorka et al., Probing distance and electrical potential within a protein pore with tethered DNA. Biophys J. Dec. 2002;83(6):3202-10.

Howorka et al., Sequence-specific detection of individual DNA strands using engineered nanopores. Nat Biotechnol. Jul. 2001; 19(7):636-9.

Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.

Huff et al., Functions of the periplasmic loop of the porin MspA from *Mycobacterium smegmatis*. J Biol Chem. Apr. 10, 2009;284(15):10223-31. doi: 10.1074/jbc.M808599200. Epub Feb. 10, 2009.

Hwang et al., Electrical behavior of droplet interface bilayer networks: experimental analysis and modeling. J Am Chem Soc. Sep. 26, 2007;129(38):11854-64. Epub Sep. 1, 2007.

Iacovache et al., Structure and assembly of pore-forming proteins. Curr Opin Struct Biol. Apr. 2010;20(2):241-6. doi:10.1016/j.sbi.2010.01.013. Epub Feb. 19, 2010.

Ide et al., Lysenin forms a voltage-dependent channel in artificial lipid bilayer membranes. Biochem Biophys Res Commun. Jul. 21, 2006;346(1):288-92. Epub May 26, 2006.

Ivanov et al., DNA tunneling detector embedded in a nanopore. Nano Lett. Jan. 12, 2011;11(1):279-85. doi: 10.1021/nl103873a. Epub Dec. 6, 2010.

Jain et al., The Oxford Nanopore MinION: delivery of nanopore sequencing to the genomics community. Genome Biol. Nov. 25, 2016;17(1):239. doi: 10.1186/s13059-016-1103-0. Erratum in: Genome Biol. Dec. 13, 2016;17 (1):256.

Jayasinghe et al., The leukocidin pore: evidence for an octamer with four LukF subunits and four LukS subunits alternating around a central axis. Protein Sci. Oct. 2005;14(10):2550-61.

Johnston et al., Coexpression of proteins in bacteria using T7-based expression plasmids: expression of heteromeric cell-cycle and transcriptional regulatory complexes. Protein Expr Purif. Dec. 2000;20(3):435-43.

Juncker et al., Prediction of lipoprotein signal peptides in Gram-negative bacteria. Protein Sci. 2003;12(8):1652-1662. doi:10.1110/ps.0303703.

Jung et al., The internal cavity of the staphylococcal alpha-hemolysin pore accommodates approximately 175 exogenous amino acid residues. Biochemistry. Jun. 28, 2005;44(25):8919-29.

Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316.

Kanaan et al., UPF1-like helicase grip on nucleic acids dictates processivity. Nat Commun. Sep. 14, 2018;9(1):3752. doi: 10.1038/s41467-018-06313-y.

Kang et al., Single protein pores containing molecular adapters at high temperatures. Angew Chem Int Ed Engl. Feb. 25, 2005;44(10):1495-9.

Kasianowicz et al., Characterization of individual polynucleotide molecules using a membrane channel. Proc Natl Acad Sci U S A. Nov. 26, 1996;93(24):13770-3.

Khulbe et al., DNA translocation through a-hemolysin nanopores with potential application to macromolecular data storage. Journal Applied Physics, vol. 97(104317):1-7 (2005).

Kimanius et al., Accelerated cryo-EM structure determination with parallelisation using GPUs in RELION-2. Elife. 2016;5:e18722. Published Nov. 15, 2016. doi: 10.7554/eLife.18722. 21 pages.

Klenchin et al., Phosphate coordination and movement of DNA in the Tn5 synaptic complex: role of the (R)YREK motif. Nucleic Acids Res. Oct. 2008;36(18):5855-62. doi: 10.1093/nar/gkn577. Epub Sep. 12, 2008.

Kobayashi et al., Comparative Physiology and Biochemistry, 2005, vol. 22, No. 3-4, pp. 139-148.

Kolinko et al., Single-cell genomics reveals potential for magnetite and greigite biomineralization in an uncultivated multicellular magnetotactic prokaryote. Environ Microbiol Rep. Oct. 2014;6(5):524-31. doi: 10.1111/1758-2229.12198. Epub Aug. 28, 2014. Abstract Only.

Krylova et al., DNA aptamers for as analytical tools for the quantitative analysis of DNA-dealkylating enzymes. Anal Biochem. 2011;414(2):261-265. doi:10.1016/j.ab.2011.03.010.

Kumar et al., PEG-labeled nucleotides and nanopore detection for single molecule DNA sequencing by synthesis. Sci Rep. 2012;2:684. Epub Sep. 21, 2012.

Langecker et al., Synthetic lipid membrane channels formed by designed DNA nanostructures. Science. Nov. 16, 2012;338(6109):932-6. doi: 10.1126/science.1225624.

Le et al., Thermostable DNA ligase-mediated PCR production of circular plasmid (PPCP) and its application in directed evolution via in situ error-prone PCR. DNA Res. Aug. 2013;20(4):375-82. doi: 10.1093/dnares/dst016. Epub Apr. 30, 2013.

Li et al., ChIA-PET tool for comprehensive chromatin interaction analysis with paired-end tag sequencing. Genome Biol. 2010;11(2):R22. doi: 10.1186/GB-2010-11-2-r22. Epub Feb. 25, 2010.

Li et al., Different Anomeric Sugar Bound States of Maltose Binding Protein Resolved by a Cytolysin A Nanopore Tweezer. ACS Nano. 2020;14(2):1727-1737. doi:10.1021/acsnano.9b07385.

(56) References Cited

OTHER PUBLICATIONS

Li et al., DNA molecules and configurations in a solid-state nanopore microscope. Nat Mater. Sep. 2003;2(9):611-5. Epub Aug. 24, 2003.

Li, Minimap2: pairwise alignment for nucleotide sequences. Bioinformatics. 2018;34(18):3094-3100. doi: 10.1093/bioinformatics/bty191.

Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010.

Loferer et al., Availability of the fibre subunit CsgA and the nucleator protein CsgB during assembly of fibronectin-binding curli is limited by the intracellular concentration of the novel lipoprotein CsgG. Mol Microbiol. 1997;26(1):11-23. doi:10.1046/j.1365-2958.1997.5231883.x.

Lovett, The DNA Exonucleases of Escherichia coli. EcoSal Plus. Dec. 2011;4(2):10.1128/ecosalplus.4.4.7. doi: 10.1128/ecosalplus.4.4.7. Author Manuscript, 45 pages.

Lu et al., Expression, purification and structural analysis of csgF gene of curli systems from Escherichia coli CFT073. Microbiol China. 2016, 43(9):2063-2071. doi:10.13344/j.microbiol.china.150752.

Lu et al., Protein Motion and Configurations in a Form-Fitting Nanopore: Avidin in ClyA. Biophys J. Sep. 4, 2018; 115(5):801-808. Epub Aug. 4, 2018. doi: 10.1016/j.bpj.2018.07.024.

Luchian et al., Single-Molecule Covalent Chemistry with Spatially Separated Reactants. Angew. Chem. Int. Ed. 2003;42:3766-771.

Ludtke, Single-Particle Refinement and Variability Analysis in EMAN2.1. Methods Enzymol. 2016;579:159-89. doi: 10.1016/bs.mie.2016.05.001. Epub Jul. 1, 2016.

Ludwig et al., Analysis of the SlyA-Controlled Expression, Subcellular Localization and Pore-Forming Activity of a 34 kDa Haemolysin (ClyA) from Escherichia coli K-12. Mol Microbiol. 1999;31(2):557-67.

Luo et al., Influence of polymer-pore interactions on translocation. Phys Rev Lett. Oct. 5, 2007;99(14):148102. Epub Oct. 1, 2007.

Maglia et al., DNA strands from denatured duplexes are translocated through engineered protein nanopores at alkaline pH. Nano Lett. Nov. 2009;9(11):3831-6. doi: 10.1021/nl9020232.

Maglia et al., Engineering a Biomimetic Biological Nanopore to Selectively Capture Folded Target Proteins. Biophysical J. Feb. 5, 2013;104(2):518a.

Maglia et al., Enhanced translocation of single DNA molecules through alpha-hemolysin nanopores by manipulation of internal charge. Proc Natl Acad Sci U S A. Dec. 16, 2008;105(50):19720-5. doi: 10.1073/pnas.0808296105. Epub Dec. 5, 2008.

Makaram et al., Trends in Nanomaterial-Based Non-Invasive Diabetes Sensing Technologies. Diagnostics. Apr. 21, 2014;4:27-46.

Manrao et al., Nucleotide Discrimination with DNA Immobilized in the MspA Nanopore. PLoS One, vol. 6(10):e25723, 7 pages (2011).

Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.

Manrao et al., Single Nucleotide Discrimination in Single Stranded DNA Immobilized within Biological Nanopre MSPA. 54th Annual Meeting of the Biophysical Society, 3 pages (2010).

Martin et al., Nanoscale protein pores modified with PAMAM dendrimers. J Am Chem Soc. Aug. 8, 2007;129(31):9640-9. Epub Jul. 18, 2007.

Marziali et al., New DNA sequencing methods. Annu Rev Biomed Eng. 2001;3:195-223.

Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.

Merzlyak et al., Conductance and ion selectivity of a mesoscopic protein nanopore probed with cysteine scanning mutagenesis. Biophys J. Nov. 2005;89(5):3059-70. Epub Aug. 5, 2005.

Mikheyev et al., A First Look at the Oxford Nanopore MinION Sequencer. Mol Ecol Res. 2014;14:1097-1102.

Miles et al., The Staphylococcal Leukocidin Bicomponent Toxin Forms Large Ionic Channels. Biochemistry. Jun. 28, 2001;40:8514-522.

Mitchell et al., Chemical tags facilitate the sensing of individual DNA strands with nanopores. Angew Chem Int Ed Engl. 2008;47(30):5565-8. doi: 10.1002/anie.200800183.

Miyazaki et al., MEGAWHOP Cloning: A Method of Creating Random Mutagenesis Libraries via Megaprimer PCR of Whole Plasmids. Methods in Enzymology. 2011;498:399-406.

Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.

Moreau et al., Coupling ion channels to receptors for biomolecule sensing. Nat Nanotechnol. Oct. 2008;3(10):620-5. doi: 10.1038/nnano.2008.242. Epub Sep. 7, 2008.

Moyer et al., Correlation Between Sweat Glucose and Blood Glucose in Subjects with Diabetes. Diabetes Technol Ther. 2012:14(5):398-402.

Mueller et al., RCSB Protein Data Bank No. 2WCD. Mar. 11, 2009. doi: 10.2210/pdb2WCD/pdb. 5 pages.

Mueller et al., The Structure of Cytolytic alpha-Helical Toxin Pore Reveals its Assembly Mechanism. Nature. Jun. 4, 2009;459:726-731.

Mueller et al., The Structure of Cytolytic alpha-Helical Toxin Pore Reveals its Assembly Mechanism. Nature. Jun. 4, 2009;459:Supplemental Information.

Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.

Mund et al., LEGO-NMR spectroscopy: a method to visualize individual subunits in large heteromeric complexes. Angew Chem Int Ed Engl. Oct. 18, 2013;52(43):11401-5. doi: 10.1002/anie.201304914. Epub Aug. 14, 2013.

Nakane et al., A nanosensor for transmembrane capture and identification of single nucleic Acid molecules. Biophys J. Jul. 2004;87(1):615-21. Erratum in: Biophys J. Nov. 2004;87(5):3618.

Nakane et al., Nanopore sensors for nucleic acid analysis. J. Phys.: Condens. Matter, vol. 15: R 1365-R1393 (2003).

Niedzwiecki et al., Inspection of the Engineered FhuA deltaC/delta4L Protein Nanopore by Polymer Exclusion. Biophys J. Nov. 2012;103:2115-124.

Nikolaidou et al., alpha-Ketoglutarate: Biological Effects of a Novel Biomarker of Heart Failure. Heart. Sep. 2010;96(17). 2 pages.

Nivala et al., Unfoldase-mediated protein translocation through an α-hemolysin nanopore. Nat Biotechnol. Mar. 2013;31(3):247-50. doi: 10.1038/nbt.2503. Epub Feb. 3, 2013. Author Manuscript, 10 pages.

Notice of Opposition for European Patent No. EP3097210 dated Aug. 12, 2019.

Ogasawara et al., Determination of Reduced Nicotinamide Adenine Dinucleotid Phosphate Concentration Using High-Performance Liquid Chromatography with Fluorescence Detection: Ratio of the Reduced Form as a Biomarker of Oxidative Stress. Biol Pharm Bull. Nov. 2009;32(11):1819-18223.

Oukhaled et al., Dynamics of Completely Unfolded and Native Proteins through Solid-State Nanopores as a Function of Electric Driving Force. Am Chem Soc. 2011 Arp 8;5(5):3628-38.

Pavlenok et al., Hetero-oligomeric MspA pores in Mycobacterium smegmatis. FEMS Microbiol Lett. Apr. 2016;363(7). pii: fnw046. doi:10.1093/femsle/fnw046. Epub Feb. 23, 2016.

Pavlenok et al., MspA nanopores from subunit dimers. PLoS One. 2012;7(6):e38726. doi: 10.1371/journal.pone.0038726. Epub Jun. 18, 2012.

Peabody et al., Type II protein secretion and its relationship to bacterial type IV pili and archaeal flagella. Microbiology. Nov. 2003;149(Pt 11):3051-3072. doi: 10.1099/mic.0.26364-0.

Plesa et al., Fast Translocation of Proteins through Solid State Nanopores. Nano Lett. Jan. 23, 2013:13:658-663.

Pud et al., Mechanical Trapping of DNA in a Double-Nanopore System. Nano Lett. 2016;16(12):8021-8028. doi:10.1021/acs.nanolett.6b04642. Author Manuscript, 17 pages.

(56) References Cited

OTHER PUBLICATIONS

Purnell et al., Nucleotide identification and orientation discrimination of DNA homopolymers immobilized in a protein nanopore. Nano Lett. Sep. 2008;8(9):3029-34. doi: 10.1021/nl802312f. Epub Aug. 13, 2008.

Quick et al., A reference Bacterial Genome Dataset Generated on the MinION Portable Single-Molecule Nanopore Sequencer. GigaScience. 2014;3(22):1-6.

Rajagopalan et al., Interaction of Dihydrofolate Reductase with Methotrexate: Ensemble and Single-Molecule Kinetics. PNAS. Oct. 15, 2002:99(21):13481-6.

Rasko et al., The pangenome structure of Escherichia coli: comparative genomic analysis of E. coli commensal and pathogenic isolates. J Bacteriol. Oct. 2008;190(20):6881-93. doi:10.1128/JB. 00619-08. Epub Aug. 1, 2008.

Reznikoff, Tn5 as a model for understanding DNA transposition. Mol Microbiol. Mar. 2003;47(5):1199-206. doi: 10.1046/j.1365-2958.2003.03382.x.

Rhee et al., Comprehensive genome-wide protein-DNA interactions detected at single-nucleotide resolution. Cell. Dec. 9, 2011;147(6):1408-19. doi: 10.1016/j.cell.2011.11.013.

Rhee et al., Nanopore sequencing technology: research trends and applications. Trends Biotechnol. Dec. 2006;24(12):580-6. Epub Oct. 19, 2006.

Robinson et al., Secretion of curli fibre subunits is mediated by the outer membrane-localized CsgG protein. Mol Microbiol. Feb. 2006;59(3):870-81. doi: 10.1111/j.1365-2958.2005.04997.x.

Rodriguez-Gallego et al., Mapping of the Circulating Metabolome Reveals alpha-Ketoglutarate as a Predictor of Morbid Obesity-Associated Non-Alcoholic Fatty Liver Disease. Int J of Obesity. 2015;39:279-287.

Rohou et al., CTFFIND4: Fast and accurate defocus estimation from electron micrographs. J Struct Biol. Nov. 2015;192(2):216-21. doi: 10.1016/j.jsb.2015.08.008. Epub Aug. 13, 2015.

Rotem et al., Protein detection by nanopores equipped with aptamers. J Am Chem Soc. Feb. 8, 2012;134(5):2781-7. doi:10.1021/ja2105653. Epub Jan. 26, 2012.

Rucker et al., Recombinant ferritin: modulation of subunit stoichiometry in bacterial expression systems. Protein Eng. 1997;10(8):967-973. doi:10.1093/protein/10.8.967.

Russo et al., Reversible permeabilization of plasma membranes with an engineered switchable pore. Nat Biotechnol. Mar. 1997;15(3):278-82.

Saariaho et al., Characteristics of MuA transposase-catalyzed processing of model transposon end DNA hairpin substrates. Nucleic Acids Res. Jun. 6, 2006;34(10):3139-49.

Sanchez-Quesada et al., Cyclic Peptides as Molecular Adapters for a Pore-Forming Protein. Journal American Chemical Society, vol. 122(48):11757-11766 (2000).

Sanchez-Quesada et al., Single DNA rotaxanes of a transmembrane pore protein. Angew Chem Int Ed Engl. Jun. 7, 2004;43(23):3063-7.

Sanderson, Personal genomes: Standard and pores. Nature. Nov. 6, 2008;456(7218):23-5. doi: 10.1038/456023a.

Sauer-Budge et al., Unzipping kinetics of double-stranded DNA in a nanopore. Phys Rev Lett. Jun. 13, 2003;90(23):238101. Epub Jun. 9, 2003.

Scheres, RELION: implementation of a Bayesian approach to cryo-EM structure determination. J Struct Biol. Dec. 2012;180(3):519-30. doi: 10.1016/j.jsb.2012.09.006. Epub Sep. 19, 2012.

Shelbourne et al., Fast copper-free click DNA ligation by the ring-strain promoted alkyne-azide cycloaddition reaction. Chem Commun (Camb). Jun. 14, 2011;47(22):6257-9. doi: 10.1039/c1cc10743g. Epub May 6, 2011.

Sivanathan et al., Generating extracellular amyloid aggregates using E. coli cells. Genes Dev. Dec. 1, 2012;26(23):2659-67. doi: 10.1101/gad.205310.112. Epub Nov. 19, 2012.

Skocaj et al., The sensing of membrane microdomains based on pore-forming toxins. Curr Med Chem. 2013;20(4):491-501.

Smeets et al., Salt dependence of ion transport and DNA translocation through solid-state nanopores. Nano Lett. Jan. 2006;6(1):89-95.

Soni et al., Synchronous optical and electrical detection of biomolecules traversing through solid-state nanopores. Rev Sci Instrum. Jan. 2010;81(1):014301. doi: 10.1063/1.3277116.

Soskine et al., An engineered ClyA nanopore detects folded target proteins by selective external association and pore entry. Nano Lett. Sep. 12, 2012;12(9):4895-900. doi:10.1021/nl3024438. Epub Aug. 6, 2012. Author Manuscript, 13 pages.

Soskine et al., Single-Molecule Analyte Recognition with ClyA Nanopores Equipped with Internal Protein Adaptors. J Am Chem Soc. 2015;137:5793-97.

Soskine et al., Tuning the size and properties of ClyA nanopores assisted by directed evolution. J Am Chem Soc. Sep. 11, 2013;135(36):13456-63. doi: 10.1021/ja4053398. Epub Aug. 27, 2013.

Sternberg et al., DNA interrogation by the CRISPR RNA-guided endonuclease Cas9. Nature. Mar. 6, 2014;507(7490):62-7. doi: 10.1038/nature13011. Epub Jan. 29, 2014. Author Manuscript, 16 pages.

Stoddart et al., Multiple base-recognition sites in a biological nanopore: two heads are better than one. Angew Chem Int Ed Engl. 2010;49(3):556-9. doi: 10.1002/anie.200905483.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas. 0901054106. Epub Apr. 20, 2009.

Sutherland et al., An analysis of mismatched duplex DNA unzipping through a bacterial nanopore. Biochem Cell Biol. Jun. 2004;82(3):407-12.

Taylor et al., Atomic resolution insights into curli fiber biogenesis. Structure. Sep. 7, 2011;19(9):1307-16. doi: 10.1016/j.str.2011.05. 015.

Taylor et al., New insight into the molecular control of bacterial functional amyloids. Front Cell Infect Microbiol. Apr. 8, 2015;5:33. doi: 10.3389/fcimb.2015.00033.

Third Party Observation for Application No. EP 15759438.3, mailed Sep. 17, 2021. 21 pages.

Third Party Observation for European Application No. EP18734933. 7, mailed Sep. 27, 2021.

Trewick et al., Oxidative Demethylation by Escherichia coli AlkB Directly Reverts DNA Base Damage. Nature. Sep. 12, 2002:419:174-78.

Tuteja et al., Helicases as molecular motors: An insight. Physica A. Dec. 1, 2006;372(1):70-83. doi: 10.1016/j.physa.2006.05.014. Epub Jun. 5, 2006.

Van De Goor, Nanopore Detection: Threading DNA Through a Tiny Hole. PharmaGenomics, vol. 4 (3):28-30 (2004).

Van Gerven et al., Bacterial amyloid formation: structural insights into curli biogenesis. Trends Microbiol. Nov. 2015; 23(11): 693-706. EPub Oct. 1, 2015. doi: 10.1016/j.tim.2015.07.010. Author Manuscript, 24 pages.

Van Gerven et al., Secretion and functional display of fusion proteins through the curlibiogenesis pathway. Mol Microbiol. Mar. 2014;91(5):1022-35. doi:10.1111/mmi.12515. Epub Feb. 12, 2014.

Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f. Author Manuscript, 16 pages.

Van Meervelt et al., Detection of Two Isomeric Binding Configurations in a Protein-Aptamer Complex with a Biological Nanopore. Am Chem Soc. Dec. 10, 2014;8(12):12826-35.

Van Meervelt et al., Real-Time Conformational Changes and Controlled Orientation of Native Proteins Inside a Protein Nanoreactor. J Am Chem Soc. Dec. 27, 2017; 139(51): 18640-18646. EPub Dec. 5, 2017. doi: 10.1021/jacs.7b10106.

Wallace et al., E. coli hemolysin E (HlyE, ClyA, SheA): X-ray crystal structure of the toxin and observation of membrane pores by electron microscopy. Cell. Jan. 21, 2000;100(2):265-76.

(56) References Cited

OTHER PUBLICATIONS

Wang et al., Engineering of protein nanopores for sequencing, chemical or protein sensing and disease diagnosis. Curr Opin Biotechnol. Jun. 2018;51:80-89. doi: 10.1016/j.copbio.2017.11. 006. Epub Dec. 10, 2017.

Wang et al., Measuring and modeling the kinetics of individual DNA-DNA polymerase complexes on a nanopore. ACS Nano. May 28, 2013;7(5):3876-86. doi: 10.1021/nn401180j. Epub Apr. 16, 2013.

Wang et al., Protein engineering with non-natural amino acids. InTechOpen; Feb. 24, 2012. DOI: 10.5772/28719.

Wanunu et al., DNA translocation governed by interactions with solid-state nanopores. Biophys J. Nov. 15, 2008;95(10):4716-25. doi: 10.1529/biophysj.108.140475. Epub Aug. 15, 2008.

Wanunu, Nanopores: A journey towards DNA sequencing. Phys Life Rev. Jun. 2012;9(2):125-58. doi:10.1016/j.plrev.2012.05.010. Epub May 18, 2012.

Welford et al., The Selectivity and Inhibition of AlkB. J. Biol. Chem. Mar. 21, 2003;278(12):10157-161.

Wendell et al., Translocation of double-stranded DNA through membrane-adapted phi29 motor protein nanopores. Nat Nanotechnol. 2009;4(11):765-772. doi: 10.1038/nnano.2009.259.

White et al., Single Ion-Channel Recordings Using Glass Nanopore Membranes. J Am Chem Soc. 2007;129:11766-775.

Wiedmann et al., Ligase chain reaction (LCR)—overview and applications. PCR Methods Appl. Feb. 1994;3(4):S51-64. doi: 10.1101/gr.3.4.s51.

Wilkinson et al., Bacterial DNA ligases. Mol Microbiol. Jun. 2001;40(6):1241-8. doi: 10.1046/j.1365-2958.2001.02479.x.

Wolfe et al., Catalyzing the translocation of polypeptides through attractive interactions. J Am Chem Soc. Nov. 14, 2007;129(45):14034-41. Epub Oct. 19, 2007.

Wong et al., Polymer capture by electro-osmotic flow of oppositely charged nanopores. J Chem Phys. Apr. 28, 2007;126(16):164903.

Wu et al., Protein nanopores with covalently attached molecular adapters. J Am Chem Soc. Dec. 26, 2007;129(51):16142-8. Epub Nov. 30, 2007.

Wu et al., Sequence-specific capture of protein-DNA complexes for mass spectrometric protein identification. PLoS One. 2011;6(10):e26217. doi: 10.1371/journal.pone.0026217. Epub Oct. 20, 2011.

Wu et al., Single-molecule detection of nitrogen mustards by covalent reaction within a protein nanopore. J Am Chem Soc. May 28, 2008;130(21):6813-9. doi: 10.1021/ja8004607. Epub Apr. 30, 2008.

Yen et al., SWR-C and INO80 chromatin remodelers recognize nucleosome-free regions near +1 nucleosomes. Cell. Sep. 12, 2013;154(6):1246-56. doi: 10.1016/j.cell.2013.08.043.

Yoo et al., Glucose Biosensors: An Overview of Use in Clinical Practice. Sensores. May 4, 2010;10:4558-4576.

Zernia et al., Current Blockades of Proteins inside Nanopores for Real-Time Metabolome Analysis. ACS Nano. Feb. 25, 2020; 14(2): 2296-2307. EPub Jan. 31, 2020. doi: 10.1021/acsnano.9b09434.

Zernia et al., Current Blockades of Proteins inside Nanopores for Real-Time Metabolome Analysis. ACS Nano. Feb. 25, 2020; 14(Supplemental Information). EPub Jan. 31, 2020. doi: 10.1021/acsnano. 9b09434. 19 pages.

Zheng et al., MotionCor2: anisotropic correction of beam-induced motion for improved cryo-electron microscopy. Nat Methods. Apr. 2017;14(4):331-332. doi: 10.1038/nmeth.4193. Epub Feb. 27, 2017.

Zhou et al., Ion Channel Probes for Scanning Ion Conductance Microscopy. Langmuir. Nov. 25, 2014;30:15351-355.

Cao et al., Mapping the sensing spots of aerolysin for single oligonucleotides analysis. Nat Commun. Jul. 19, 2018;9(1):2823. doi: 10.1038/s41467-018-05108-5. 9 pages.

Colas et al., Microscopical investigations of nisin-loaded nanoliposomes prepared by Mozafari method and their bacterial targeting. Micron. 2007;38(8):841-7. doi: 10.1016/j.micron.2007.06.013. Epub Jul. 3, 2007.

Dong et al., Oroxylin A inhibits hemolysis via hindering the self-assembly of α-hemolysin heptameric transmembrane pore. PLoS Comput Biol. 2013;9(1):e1002869. doi: 10.1371/journal.pcbi. 1002869. Epub Jan. 17, 2013.

Fiaschi et al., Auto-Assembling Detoxified *Staphylococcus aureus* Alpha-Hemolysin Mimicking the Wild-Type Cytolytic Toxin. Clin Vaccine Immunol. Jun. 6, 2016;23(6):442-50. doi: 10.1128/CVI. 00091-16.

Ghanem et al., Chimeric mutants of staphylococcal hemolysin, which act as both one-component and two-component hemolysin, created by grafting the stem domain. FEBS J. Jun. 2022;289(12):3505-3520. doi: 10.1111/febs.16354. Epub Feb. 16, 2022.

González-Pérez et al., Biomimetic triblock copolymer membrane arrays: a stable template for functional membrane proteins. Langmuir. Sep. 15, 2009;25(18):10447-50. doi: 10.1021/la902417m.

Ho et al., Engineering a nanopore with co-chaperonin function. Sci Adv. Dec. 11, 2015;1(11):e1500905. doi: 10.1126/sciadv.1500905. 9 pages.

Montal et al., Formation of bimolecular membranes from lipid monolayers and a study of their electrical properties. Proc Natl Acad Sci U S A. Dec. 1972;69(12):3561-6. doi: 10.1073/pnas.69.12.3561.

Walker et al., Assembly of the oligomeric membrane pore formed by Staphylococcal alpha-hemolysin examined by truncation mutagenesis. J Biol Chem. Oct. 25, 1992;267(30):21782-6.

Willems et al., Single-molecule nanopore enzymology. Philos Trans R Soc Lond B Biol Sci. Aug. 5, 2017;372(1726):20160230. doi: 10.1098/rstb.2016.0230. 11 pages.

* cited by examiner

METHOD OF NANOPORE SEQUENCING

RELATED APPLICATIONS

This application is a continuation of U.S. application Ser. No. 15/551,884, filed Aug. 17, 2017, which is a national stage application under 35 U.S.C. § 371 of PCT International Application No. PCT/GB2016/050391, filed Feb. 17, 2016, which claims foreign priority benefits under 35 U.S.C. § 119 (a)-(d) or 35 U.S.C. § 365 (b) of British application number 1502810.3, filed Feb. 19, 2015, the contents of each of which are incorporated herein by reference in their entireties.

Incorporated by Reference of Sequence Listing

This application contains a Sequence Listing which has been submitted in ASCII format via EFS-WEB and is hereby incorporated by reference in its entirety. Said ASCII copy, created on Feb. 17, 2022, named 0036670059US01-SEQ-MSB, is 127,290 bytes in size.

FIELD OF THE INVENTION

The invention relates to a novel method of producing hetero-oligomeric pores. The invention also relates to hetero-oligomeric pores produced using the method and polynucleotide characterisation using the hetero-oligomeric pores.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identities of the nucleotides are derived. Strand sequencing can involve the use of a polynucleotide binding protein to control the movement of the polynucleotide through the pore.

The different forms of Msp are porins from *Mycobacterium smegmatis*. MspA is a 157 kDa octameric porin from *Mycobacterium smegmatis*. Wild-type MspA does not interact with DNA in a manner that allows the DNA to be characterised or sequenced. The structure of MspA and the modifications required for it to interact with and characterise DNA have been well documented (Butler, 2007, Nanopore Analysis of Nucleic Acids, Doctor of Philosophy Dissertation, University of Washington; Gundlach, Proc Natl Acad Sci USA. 2010 Sep. 14; 107(37):16060-5. Epub 2010 Aug. 26; and International Application No. PCT/GB2012/050301 (published as WO/2012/107778). Negative charges, such as those at positions 90, 91 and 93, are typically removed from the pore to make it neutral.

SUMMARY OF THE INVENTION

The inventors have surprisingly demonstrated that hetero-oligomeric pores comprising two different monomers in a specific stoichiometric ratio can be produced in a single cell by differentially expressing the two different monomers.

Accordingly, the invention provides a method for producing a hetero-oligomeric pore comprising two different monomers in a specific stoichiometric ratio, comprising: (a) transfecting or transforming a cell with the first different monomer in a first inducible vector; (b) transfecting or transforming the cell with the second different monomer in a second inducible vector; and (c) inducing the first and second inducible vectors such that the cell produces the hetero-oligomeric pore comprising the first and second different monomers in the specific stoichiometric ratio.

The invention also provides:

a hetero-oligomeric pore produced using a method of the invention;

a method of characterising a target polynucleotide, comprising:
a) contacting the polynucleotide with a hetero-oligomeric pore of the invention such that the polynucleotide moves through the pore; and
b) taking one or more measurements as the polynucleotide moves with respect to the pore, wherein the measurements are indicative of one or more characteristics of the polynucleotide, and thereby characterising the target polynucleotide;

a kit for characterising a target polynucleotide comprising (a) a hetero-oligomeric pore of the invention and (b) the components of a membrane;

an apparatus for characterising target polynucleotides in a sample, comprising (a) a plurality of hetero-oligomeric pores of the invention and (b) a plurality of membranes;

a method of characterising a target polynucleotide, comprising:
a) contacting the polynucleotide with a hetero-oligomeric pore of the invention, a polymerase and labelled nucleotides such that phosphate labelled species are sequentially added to the target polynucleotide by the polymerase, wherein the phosphate species contain a label specific for each nucleotide; and
b) detecting the phosphate labelled species using the pore and thereby characterising the polynucleotide;

a method of forming a sensor for characterising a target polynucleotide, comprising forming a complex between a hetero-oligomeric pore of the invention and a polynucleotide binding protein and thereby forming a sensor for characterising the target polynucleotide; and a sensor for characterising a target polynucleotide, comprising a complex between a hetero-oligomeric pore of the invention and a polynucleotide binding protein.

Figure 1:
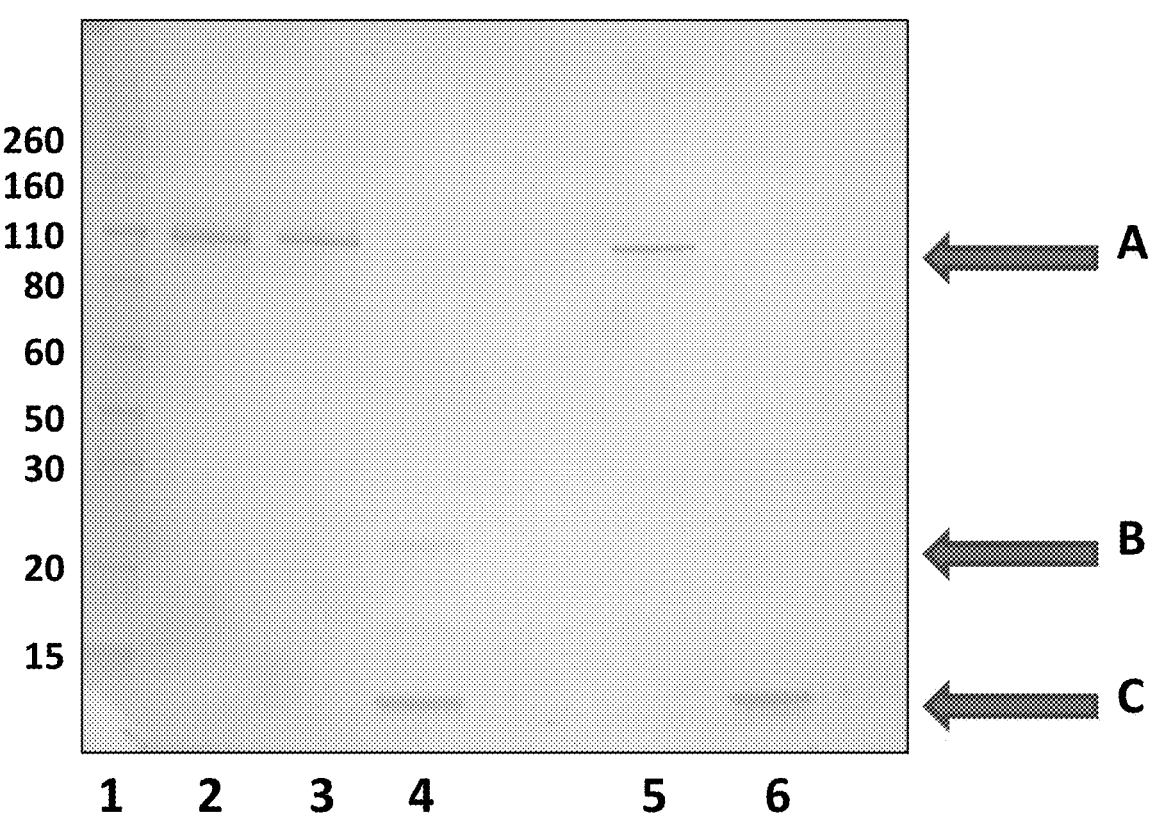
FIG. 1 shows a 10% TGX gel with bands visualised with coomassie stain. Lane 1 corresponds to a protein molecular weight marker. The numbers along the side of the gel correspond to kDa. Lane 2 corresponds to purified MspA 2. Lane 3 corresponds to MspA 2 after heating at 85° C. Lane 4 corresponds to MspA 2 after heating to 100° C. in 50% DMSO. Lane 5 corresponds to purified MspA—((Del-L74/G75/D118/L119)D56N/E59R/L88N/D90N/D91N/Q126R/D134R/E139K)8=MspA 6 (homopolymeric nanopore as a reference). Lane 6 corresponds to MspA 6 after heating to 100° C. in 50% DMSO (under these conditions the oligo-meric pore can be broken down into its constituent monomer subunits). Band A corresponds to oligomerised MspA homo/heteropores comprising 8 monomer units. Band B corresponds to the monomer unit of MspA 2 which contained the BasTL-H6 attached. Band C corresponds to the MspA monomer units which did not contain a BasTL-H6 attached.

D118R/Q126R/D134R/E139K/R8)8 (SEQ ID NO: 2 with the following mutations G75S/G77S/L88N/D90N/D91N/D93N/D118R/Q126R/D134R/E139K where there is a R8 tag attached at the C terminus) which had been heat treated at 85° C. for 15 minutes. Lane G corresponded to the attempt to oligomerise the homo-oligomer MspA—(G75S/G77S/L88N/D90N/D91N/D93N/D118R/Q126R/D134R/E139K/R8H6)8 (SEQ ID NO: 2 with the following mutations G75S/G77S/L88N/D90N/D91N/D93N/D118R/Q126R/D134R/E139K where there is a R8H6 tag attached at the C terminus). Lane H corresponded to the attempt to oligomerise the homo-oligomer MspA—(G75S/G77S/L88N/D90N/D91N/D93N/D118R/Q126R/D134R/E139K/R8H6)8 (SEQ ID NO: 2 with the following mutations G75S/G77S/L88N/D90N/D91N/D93N/D118R/Q126R/D134R/E139K where there is a R8H6 tag attached at the C terminus) which had been heat treated at 85° C. for 15 minutes. White dots indicate the MspA homo-oligomer formed in each lane.

DESCRIPTION OF THE SEQUENCE LISTING

SEQ ID NO: 1 shows the codon optimised polynucleotide sequence encoding the wild-type MspA monomer. This mutant lacks the signal sequence.

SEQ ID NO: 2 shows the amino acid sequence of the mature form of the wild-type MspA monomer. This mutant lacks the signal sequence.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the polynucleotide sequence encoding the Phi29 DNA polymerase.

SEQ ID NO: 9 shows the amino acid sequence of the Phi29 DNA polymerase.

SEQ ID NO: 10 shows the codon optimised polynucleotide sequence derived from the sbcB gene from *E. coli*. It encodes the exonuclease I enzyme (EcoExo I) from *E. coli*.

SEQ ID NO: 11 shows the amino acid sequence of exonuclease I enzyme (EcoExo I) from *E. coli*.

SEQ ID NO: 12 shows the codon optimised polynucleotide sequence derived from the xthA gene from *E. coli*. It encodes the exonuclease III enzyme from *E. coli*.

SEQ ID NO: 13 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.

SEQ ID NO: 14 shows the codon optimised polynucleotide sequence derived from the recJ gene from *T. thermophilus*. It encodes the RecJ enzyme from *T. thermophilus* (TthRecJ-cd).

SEQ ID NO: 15 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides.

SEQ ID NO: 16 shows the codon optimised polynucleotide sequence derived from the bacteriophage lambda exo (redX) gene. It encodes the bacteriophage lambda exonuclease.

SEQ ID NO: 17 shows the amino acid sequence of the bacteriophage lambda exonuclease. The sequence is one of three identical subunits that assemble into a trimer. The enzyme performs highly processive digestion of nucleotides from one strand of dsDNA, in a 5'-3'direction (http://www.neb.com/nebecomm/products/productM0262.asp). Enzyme initiation on a strand preferentially requires a 5' overhang of approximately 4 nucleotides with a 5' phosphate.

SEQ ID NO: 18 shows the amino acid sequence of Hel308 Mbu.

SEQ ID NO: 19 shows the amino acid sequence of Hel308 Csy.

SEQ ID NO: 20 shows the amino acid sequence of Hel308 Tga.

SEQ ID NO: 21 shows the amino acid sequence of Hel308 Mhu.

SEQ ID NO: 22 shows the amino acid sequence of TraI Eco.

SEQ ID NO: 23 shows the amino acid sequence of XPD Mbu.

SEQ ID NO: 24 shows the amino acid sequence of Dda 1993.

SEQ ID NO: 25 shows the amino acid sequence of Trwc Cba.

SEQ ID NO: 26 shows the amino acid sequence of the BasTL. This sequence is attached at the C terminus of the MspA monomers.

SEQ ID NO: 27 shows a polynucleotide encoding sequence used in Example 1 and 2.

SEQ ID NO: 28 shows a polynucleotide encoding sequence used in Example 1 and 2.

SEQ ID NO: 29 shows a polynucleotide encoding sequence used in Example 3.

SEQ ID NO: 30 shows a polynucleotide encoding sequence used in Example 3.

SEQ ID NO: 31 shows the amino acid sequence of the lysenin monomer.

SEQ ID NO: 32 shows the amino acid sequence of the mature form of the wild-type CsgG monomer from *Escherchia coli* Str. K-12 substr. MC4100. This monomer lacks the signal sequence. The abbreviation used for this CsgG=CsgG-Eco.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polynucleotide" includes two or more polynucleotides, reference to "a polynucleotide binding protein includes two or more such proteins, reference to "a helicase" includes two or more helicases, reference to "a monomer" refers to two or more monomers, reference to "a pore" includes two or more pores and the like.

All publications, patents and patent applications cited herein, whether supra or infra, are hereby incorporated by reference in their entirety.

Method of the Invention

Hetero-Oligomeric Pore

The invention provides a method for producing a hetero-oligomeric pore. The hetero-oligomeric pore contains sufficient monomers to form the pore. The monomers may be of any type. The pore typically comprises at least 3, at least 4, at least 5, at least 6, at least 7, at least 8, at least 9, at least 10 monomers, at least 11 monomers, at least 12 monomers, at least 13 monomers or at least 14 monomers, such as 3, 4, 5, 6, 7, 8, 9, 10, 11, 12, 13 or 14 monomers. The pore preferably comprises seven, eight or nine monomers.

The pore is hetero-oligomeric because it comprises two different monomers. The pore may be hetero-oligomeric because it comprises at least two different monomers. The two monomers may be different in any way. The second different monomer is typically different from the first different monomer on the basis of its amino acid sequence. The second different monomer may be different from the first different monomer on the basis of 1, 2, 3, 4, 5, 10, 15, 20, 30, 40 or more amino acid differences. The second different monomer may be modified with a tag as discussed below.

The hetero-oligomeric pore is typically derived from or based on a transmembrane protein pore. The hetero-oligomeric pore is typically a variant of a transmembrane protein pore. The hetero-oligomeric pore is typically a variant of a transmembrane protein pore in which one or more of the monomers in the pore has been modified such that it is different from the others. The hetero-oligomeric pore typically comprises monomers from a transmembrane protein pore, such as MspA, MspB, MspC or MspD, in which one or more of the monomers in the pore has been modified such that it is different from the others.

The hetero-oligomeric pore typically does not comprise two different monomers each from two different transmembrane protein pores. In particular, the hetero-oligomeric pore typically does not comprise a first monomer from MspA and a second monomer from α-hemolysin. The hetero-oligomeric pore may comprise two different monomers each from two different Msp pores, such as two of MspA, MspB, MspC and MspD.

The hetero-oligomeric pore may be derived from or based on any transmembrane protein pore. A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

Any transmembrane protein pore may be used in the invention. The transmembrane protein pore is typically a collection of polypeptides, i.e. an oligomer, that are arranged around a central axis to form a channel. The channel permits hydrated ions, nucleotides or polynucleotides, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analytes such as nucleotides or polynucleotides to flow from one side of the membrane, such as a triblock copolymer membrane, to the other. The transmembrane protein pore typically allows a polynucleotide, such as DNA or RNA, to be moved through the pore.

The transmembrane protein pore is an oligomer. The transmembrane protein pore is preferably made up of several repeating subunits, such as least 3, at least 4, at least 5, at least 6, at least 7, at least 8, at least 9, at least 10 monomers, at least 11 monomers, at least 12 monomers, at least 13 monomers or at least 14 monomers, such as 3, 4, 5, 6, 7, 8, 9, 10, 11, 12, 13 or 14 monomers. The pore is preferably a trimeric, tetrameric, pentameric, hexameric, heptameric, octameric or nonameric pore. The naturally-occurring transmembrane protein pore may be a homo-oligomer or a hetero-oligomer.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β pore forming toxins, such as α-hemolysin, anthrax toxin, NetB, CytK and leukocidins, and outer membrane proteins/porins of bacteria, such as *Mycobacterium smegmatis* porin (Msp), for example MspA, MspB, MspC or MspD, NfpAB pore from *Nocardia farcinica*, outer membrane porin F (OmpF), outer membrane porin G (OmpG), outer membrane phospholipase A and *Neisseria* autotransporter lipoprotein (NalP), and other pores, such as lysenin, CsgG and FRAC. α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from lysenin. Suitable pores derived from lysenin are disclosed in International Application No. PCT/GB2013/050667 (published as WO 2013/153359). The transmembrane pore may be derived from CsgG. Suitable pores derived from CsgG are disclosed in International Application No. PCT/EP2015/069965. The transmembrane pore may be derived from Msp, such as MspA, or from α-hemolysin (α-HL).

The hetero-oligomeric pore may be derived from or based on MspA or a variant thereof, i.e. derived from a transmembrane pore comprising seven or more monomers comprising the sequence shown in SEQ ID NO: 2 or a variant thereof. The hetero-oligomeric pore is more preferably derived from a pore which comprises 8 or 9 monomers comprising the sequence shown in SEQ ID NO: 2 or a variant thereof. The first different monomer preferably comprises the sequence shown in SEQ ID NO: 2 or a variant thereof. The second different monomer preferably comprises the sequence shown in SEQ ID NO: 2 or a variant thereof. Most preferably, the first and second different monomers comprise different variants of the sequence shown in SEQ ID NO: 2. SEQ ID NO: 2 and variants thereof are discussed in more detail below.

The hetero-oligomeric pore may also be derived from or based on α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The hetero-oligomeric pore may be derived from a transmembrane protein pore comprising seven monomers each comprising the sequence shown in SEQ ID NO: 4 or a variant thereof. The hetero-oligomeric pore produced in accordance with the invention may comprise two different monomers each the sequence shown in SEQ ID NO: 4 or a variant thereof. The first different monomer preferably comprises the sequence shown in SEQ ID NO: 4 or a variant thereof. The second different monomer preferably comprises the sequence shown in SEQ ID NO: 4 or a variant thereof. Most preferably, the first and second different monomers comprise different variants of the sequence shown in SEQ ID NO: 4.

Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction within the barrel or channel of α-HL.

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into an amphiphilic layer, such as a triblock copolymer membrane, along with other appropriate subunits and its ability to oligomerise to form a pore may be determined. Methods are known in the art for inserting subunits into amphiphilic layers, such as triblock copolymer membranes.

The variant may include modifications that facilitate covalent attachment. The variant preferably comprises one or more reactive cysteine residues that facilitate attachment, for instance to other monomers. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a *Staphylococcus bacterium*. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4, a variant will preferably be at least 50% homologous to that sequence based on amino acid similarity or identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid similarity or identity to the amino acid sequence of SEQ ID NO:

4 over the entire sequence. There may be at least 80%, for example at least 85%, 90% or 95%, amino acid similarity or identity over a stretch of 200 or more, for example 230, 250, 270 or 280 or more, contiguous amino acids ("hard homology"). Homology can be determined as discussed below.

The hetero-oligomeric pore may also be derived from or based on lysenin. The wild type α-HL pore is formed of at least 7, at least 8, at least 9 or at least 10, preferably nine, identical monomers or subunits (i.e. it is heptameric). The sequence of one monomer or subunit of lysenin is shown in SEQ ID NO: 31. The hetero-oligomeric pore may be derived from a transmembrane protein pore comprising at least 7, at least 8, at least 9 or at least 1, preferably nine, monomers each comprising the sequence shown in SEQ ID NO: 31 or a variant thereof. The hetero-oligomeric pore produced in accordance with the invention may comprise two different monomers each the sequence shown in SEQ ID NO: 31 or a variant thereof. The first different monomer preferably comprises the sequence shown in SEQ ID NO: 31 or a variant thereof. The second different monomer preferably comprises the sequence shown in SEQ ID NO: 31 or a variant thereof. Most preferably, the first and second different monomers comprise different variants of the sequence shown in SEQ ID NO: 31.

The variant preferably comprises one or more modifications from about position 44 to about position 126 of SEQ ID NO: 2 which alter the ability of the monomer to interact with a polynucleotide. Such modifications are disclosed in International Application No. PCT/GB2013/050667 (published as WO2013153359).

The ability of the monomer to interact with a polynucleotide can be determined using methods that are well-known in the art. The monomer may interact with a polynucleotide in any way, e.g. by non-covalent interactions, such as hydrophobic interactions, hydrogen bonding, Van der Waal's forces, pi (π)-cation interactions or electrostatic forces. For instance, the ability of the region to bind to a polynucleotide can be measured using a conventional binding assay. Suitable assays include, but are not limited to, fluorescence-based binding assays, nuclear magnetic resonance (NMR), Isothermal Titration Calorimetry (ITC) or Electron spin resonance (ESR) spectroscopy. Alternatively, the ability of a pore comprising one or more of the mutant monomers to interact with a polynucleotide can be determined using any of the methods discussed above or below.

The one or more modifications are within the region from about position 44 to about position 126 of SEQ ID NO: 2. The one or more modifications are preferably within any one of the following regions: from about position 40 to about position 125, from about position 50 to about position 120, from about position 60 to about position 110 and from about position 70 to about position 100. If the one or more modifications are being made to improve polynucleotide capture, they are more preferably made within any one of the following regions: from about position 44 to about position 103, from about position 68 to about position 103, from about position 84 to about position 103, from about position 44 to about position 97, from about position 68 to about position 97 or from about position 84 to about position 97. If the one or more modifications are being made to improve polynucleotide recognition or discrimination, they are more preferably made within any one of the following regions: from about position 44 to about position 109, from about position 44 to about position 97 or from about position 48 to about position 88. The region is preferably from about position 44 to about position 67 of SEQ ID NO: 2.

If the one or more modifications are intended improve polynucleotide recognition or discrimination, they are preferably made in addition to one or more modifications to improve polynucleotide capture. This allows pores formed from the mutant monomer to effectively capture a polynucleotide and then characterise the polynucleotide, such as estimate its sequence, as discussed below.

Modifications of protein nanopores that alter their ability to interact with a polynucleotide, in particular improve their ability to capture and/or recognise or discriminate polynucleotides, are well documented in the art. For instance, such modifications are disclosed in WO 2010/034018 and WO 2010/055307. Similar modifications can be made to the lysenin monomer in accordance with this invention. Preferred modifications are disclosed International Application No. PCT/GB2013/050667 (published as WO2013153359).

Any number of modifications may be made, such as 1, 2, 5, 10, 15, 20, 30 or more modifications. Any modification(s) can be made as long as the ability of the monomer to interact with a polynucleotide is altered. Suitable modifications include, but are not limited to, amino acid substitutions, amino acid additions and amino acid deletions. The one or more modifications are preferably one or more substitutions. This is discussed in more detail below.

The one or more modifications preferably (a) alter the steric effect of the monomer, or preferably alter the steric effect of the region, (b) alter the net charge of the monomer, or preferably alter the net charge of the region, (c) alter the ability of the monomer, or preferably of the region, to hydrogen bond with the polynucleotide, (d) introduce or remove chemical groups that interact through delocalized electron pi systems and/or (e) alter the structure of the monomer, or preferably alter the structure of the region. The one or more modifications more preferably result in any combination of (a) to (e), such as (a) and (b); (a) and (c); (a) and (d); (a) and (e); (b) and (c); (b) and (d); (b) and (e); (c) and (d); (c) and (e); (d) and (e), (a), (b) and (c); (a), (b) and (d); (a), (b) and (e); (a), (c) and (d); (a), (c) and (e); (a), (d) and (e); (b), (c) and (d); (b), (c) and (e); (b), (d) and (e); (c), (d) and (e); (a), (b), (c) and d); (a), (b), (c) and (e); (a), (b), (d) and (e); (a), (c), (d) and (e); (b), (c), (d) and (e); and (a), (b), (c) and (d).

A variant of SEQ ID NO: 31 is a protein that has an amino acid sequence which varies from that of SEQ ID NO: 31 and which retains its pore forming ability. The ability of a variant to form a pore can be assayed using any method known in the art and described above.

Over the entire length of the amino acid sequence of SEQ ID NO: 31, a variant will preferably be at least 50% homologous to that sequence based on amino acid similarity or identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid similarity or identity to the amino acid sequence of SEQ ID NO: 31 over the entire sequence. There may be at least 80%, for example at least 85%, 90% or 95%, amino acid similarity or identity over a stretch of 200 or more, for example 230, 250, 270 or 280 or more, contiguous amino acids ("hard homology"). Homology can be determined as discussed below.

The hetero-oligomeric pore may also be derived from or based on CsgG. The wild type CsgG pore is formed of at least 7, at least 8, at least 9 or at least 10, preferably nine, identical monomers or subunits (i.e. it is heptameric). The sequence of one monomer or subunit of CsgG is shown in SEQ ID NO: 32. The hetero-oligomeric pore may be derived from a transmembrane protein pore comprising at least 7, at least 8, at least 9 or at least 10, preferably nine, monomers each comprising the sequence shown in SEQ ID NO: 32 or a variant thereof. The hetero-oligomeric pore produced in accordance with the invention may comprise two different monomers each the sequence shown in SEQ ID NO: 32 or a variant thereof. The first different monomer preferably comprises the sequence shown in SEQ ID NO: 32 or a variant thereof. The second different monomer preferably comprises the sequence shown in SEQ ID NO: 32 or a variant thereof. Most preferably, the first and second different monomers comprise different variants of the sequence shown in SEQ ID NO: 32.

In all of the discussion herein, the standard one letter codes for amino acids are used. These are as follows: alanine (A), arginine (R), asparagine (N), aspartic acid (D), cysteine (C), glutamic acid (E), glutamine (Q), glycine (G), histidine (H), isoleucine (I), leucine (L), lysine (K), methionine (M), phenylalanine (F), proline (P), serine (S), threonine (T), tryptophan (W), tyrosine (Y) and valine (V). Standard substitution notation is also used, i.e. Q42R means that Q at position 42 is replaced with R.

The variant of SEQ ID NO: 32 comprises one or more of the following (i) one or more mutations at the following positions (i.e. mutations at one or more of the following positions) N40, D43, E44, S54, S57, Q62, R97, E101, E124, E131, R142, T150 and R192, such as one or more mutations at the following positions (i.e. mutations at one or more of the following positions) N40, D43, E44, S54, S57, Q62, E101, E131 and T150 or N40, D43, E44, E101 and E131; (ii) mutations at Y51/N55, Y51/F56, N55/F56 or Y51/N55/F56; (iii) Q42R or Q42K; (iv) K49R; (v) N102R, N102F, N102Y or N102W; (vi) D149N, D149Q or D149R; (vii) E185N, E185Q or E185R; (viii) D195N, D195Q or D195R; (ix) E201N, E201Q or E201R; (x) E203N, E203Q or E203R; and (xi) deletion of one or more of the following positions F48, K49, P50, Y51, P52, A53, S54, N55, F56 and S57. The variant may comprise any combination of (i) to (xi).

If the variant comprises any one of (i) and (iii) to (xi), it may further comprise a mutation at one or more of Y51, N55 and F56, such as at Y51, N55, F56, Y51/N55, Y51/F56, N55/F56 or Y51/N55/F56.

In (i), the variant may comprises mutations at any number and combination of N40, D43, E44, S54, S57, Q62, R97, E101, E124, E131, R142, T150 and R192. In (i), the variant preferably comprises one or more mutations at the following positions (i.e. mutations at one or more of the following positions) N40, D43, E44, S54, S57, Q62, E101, E131 and T150. In (i), the variant preferably comprises one or more mutations at the following positions (i.e. mutations at one or more of the following positions) N40, D43, E44, E101 and E131. In (i), the variant preferably comprises a mutation at S54 and/or S57. In (i), the variant more preferably comprises a mutation at (a) S54 and/or S57 and (b) one or more of Y51, N55 and F56, such as at Y51, N55, F56, Y51/N55, Y51/F56, N55/F56 or Y51/N55/F56. If S54 and/or S57 are deleted in (xi), it/they cannot be mutated in (i) and vice versa. In (i), the variant preferably comprises a mutation at T150, such as T150I. Alternatively the variant preferably comprises a mutation at (a) T150 and (b) one or more of Y51, N55 and F56, such as at Y51, N55, F56, Y51/N55, Y51/F56, N55/F56 or Y51/N55/F56. In (i), the variant preferably comprises a mutation at Q62, such as Q62R or Q62K. Alternatively the variant preferably comprises a mutation at (a) Q62 and (b) one or more of Y51, N55 and F56, such as at Y51, N55, F56, Y51/N55, Y51/F56, N55/F56 or Y51/N55/F56. The variant may comprise a mutation at D43, E44, Q62 or any combination thereof, such as D43, E44, Q62, D43/E44, D43/Q62, E44/Q62 or D43/E44/Q62. Alternatively the variant preferably comprises a mutation at (a) D43, E44, Q62, D43/E44, D43/Q62, E44/Q62 or D43/E44/Q62 and (b) one or more of Y51, N55 and F56, such as at Y51, N55, F56, Y51/N55, Y51/F56, N55/F56 or Y51/N55/F56.

In (ii) and elsewhere in this application, the / symbol means "and" such that Y51/N55 is Y51 and N55. In (ii), the variant preferably comprises mutations at Y51/N55. It has been proposed that the constriction in CsgG is composed of three stacked concentric rings formed by the side chains of residues Y51, N55 and F56 (Goyal et al, 2014, Nature, 516, 250-253). Mutation of these residues in (ii) may therefore decrease the number of nucleotides contributing to the current as the polynucleotide moves through the pore and thereby make it easier to identify a direct relationship between the observed current (as the polynucleotide moves through the pore) and the polynucleotide. Y56 may be mutated in any of the ways discussed below with reference to variants and pores useful in the method of the invention.

In (v), the variant may comprise N102R, N102F, N102Y or N102W. The variant preferably comprises (a) N102R, N102F, N102Y or N102W and (b) a mutation at one or more of Y51, N55 and F56, such as at Y51, N55, F56, Y51/N55, Y51/F56, N55/F56 or Y51/N55/F56.

In (xi), any number and combination of K49, P50, Y51, P52, A53, S54, N55, F56 and S57 may be deleted. Preferably one or more of K49, P50, Y51, P52, A53, S54, N55 and S57 may be deleted. If any of Y51, N55 and F56 are deleted in (xi), it/they cannot be mutated in (ii) and vice versa.

In (i), the variant preferably comprises one of more of the following substitutions N40R, N40K, D43N, D43Q, D43R, D43K, E44N, E44Q, E44R, E44K, S54P, S57P, Q62R, Q62K, R97N, R97G, R97L, E101N, E101Q, E101R, E101K, E101F, E101Y, E101W, E124N, E124Q, E124R, E124K, E124F, E124Y, E124W, E131D, R142E, R142N, T150I, R192E and R192N, such as one or more of N40R, N40K, D43N, D43Q, D43R, D43K, E44N, E44Q, E44R, E44K, S54P, S57P, Q62R, Q62K, E101N, E101Q, E101R, E101K, E101F, E101Y, E101W, E131D and T150I, or one or more of N40R, N40K, D43N, D43Q, D43R, D43K, E44N, E44Q, E44R, E44K, E101N, E101Q, E101R, E101K, E101F, E101Y, E101W and E131D. The variant may comprise any number and combination of these substitutions. In (i), the variant preferably comprises S54P and/or S57P. In (i), the variant preferably comprises (a) S54P and/or S57P and (b) a mutation at one or more of Y51, N55 and F56, such as at Y51, N55, F56, Y51/N55, Y51/F56, N55/F56 or Y51/N55/F56. The mutations at one or more of Y51, N55 and F56 may be any of those discussed below. In (i), the variant preferably comprises F56A/S57P or S54P/F56A. The variant preferably comprises T150I. Alternatively the variant preferably comprises a mutation at (a) T150I and (b) one or more of Y51, N55 and F56, such as at Y51, N55, F56, Y51/N55, Y51/F56, N55/F56 or Y51/N55/F56.

In (i), the variant preferably comprises Q62R or Q62K. Alternatively the variant preferably comprises (a) Q62R or Q62K and (b) a mutation at one or more of Y51, N55 and F56, such as at Y51, N55, F56, Y51/N55, Y51/F56, N55/F56 or Y51/N55/F56. The variant may comprise D43N, E44N, Q62R or Q62K or any combination thereof, such as D43N, E44N, Q62R, Q62K, D43N/E44N, D43N/Q62R, D43N/Q62K, E44N/Q62R, E44N/Q62K, D43N/E44N/Q62R or D43N/E44N/Q62K. Alternatively the variant preferably comprises (a) D43N, E44N, Q62R, Q62K, D43N/E44N, D43N/Q62R, D43N/Q62K, E44N/Q62R, E44N/Q62K, D43N/E44N/Q62R or D43N/E44N/Q62K and (b) a mutation at one or more of Y51, N55 and F56, such as at Y51, N55, F56, Y51/N55, Y51/F56, N55/F56 or Y51/N55/F56.

In (i), the variant preferably comprises D43N.

In (i), the variant preferably comprises E101R, E101S, E101F or E101N.

In (i), the variant preferably comprises E124N, E124Q, E124R, E124K, E124F, E124Y, E124W or E124D, such as E124N.

In (i), the variant preferably comprises R142E and R142N.

In (i), the variant preferably comprises R97N, R97G or R97L.

In (i), the variant preferably comprises R192E and R192N.

In (ii), the variant preferably comprises F56N/N55Q, F56N/N55R, F56N/N55K, F56N/N55S, F56N/N55G, F56N/N55A, F56N/N55T, F56Q/N55Q, F56Q/N55R, F56Q/N55K, F56Q/N55S, F56Q/N55G, F56Q/N55A, F56Q/N55T, F56R/N55Q, F56R/N55R, F56R/N55K, F56R/N55S, F56R/N55G, F56R/N55A, F56R/N55T, F56S/N55Q, F56S/N55R, F56S/N55K, F56S/N55S, F56S/N55G, F56S/N55A, F56S/N55T, F56G/N55Q, F56G/N55R, F56G/N55K, F56G/N55S, F56G/N55G, F56G/N55A, F56G/N55T, F56A/N55Q, F56A/N55R, F56A/N55K, F56A/N55S, F56A/N55G, F56A/N55A, F56A/N55T, F56K/N55Q, F56K/N55R, F56K/N55K, F56K/N55S, F56K/N55G, F56K/N55A, F56K/N55T, F56N/Y51L, F56N/Y51V, F56N/Y51A, F56N/Y51N, F56N/Y51Q, F56N/Y51S, F56N/Y51G, F56Q/Y51L, F56Q/Y51V, F56Q/Y51A, F56Q/Y51N, F56Q/Y51Q, F56Q/Y51S, F56Q/Y51G, F56R/Y51L, F56R/Y51V, F56R/Y51A, F56R/Y51N, F56R/Y51Q, F56R/Y51S, F56R/Y51G, F56S/Y51L, F56S/Y51V, F56S/Y51A, F56S/Y51N, F56S/Y51Q, F56S/Y51G, F56G/Y51L, F56G/Y51V, F56G/Y51A, F56G/Y51N, F56G/Y51Q, F56G/Y51S, F56G/Y51G, F56A/Y51L, F56A/Y51V, F56A/Y51A, F56A/Y51N, F56A/Y51Q, F56A/Y51S, F56A/Y51G, F56K/Y51L, F56K/Y51V, F56K/Y51A, F56K/Y51N, F56K/Y51Q, F56K/Y51S, F56K/Y51G, N55Q/Y51L, N55Q/Y51V, N55Q/Y51A, N55Q/Y51N, N55Q/Y51Q, N55Q/Y51S, N55Q/Y51G, N55R/Y51L, N55R/Y51V, N55R/Y51A, N55R/Y51N, N55R/Y51Q, N55R/Y51S, N55R/Y51G, N55K/Y51L, N55K/Y51V, N55K/Y51A, N55K/Y51N, N55K/Y51Q, N55K/Y51S, N55K/Y51G, N55S/Y51L, N55S/Y51V, N55S/Y51A, N55S/Y51N, N55S/Y51Q, N55S/Y51S, N55S/Y51G, N55G/Y51L, N55G/Y51V, N55G/Y51A, N55G/Y51N, N55G/Y51Q, N55G/Y51S, N55G/Y51G, N55A/Y51L, N55A/Y51V, N55A/Y51A, N55A/Y51N, N55A/Y51Q, N55A/Y51S, N55A/Y51G, N55T/Y51L, N55T/Y51V, N55T/Y51A, N55T/Y51N, N55T/Y51Q, N55T/Y51S, N55T/Y51G, F56N/N55Q/Y51L, F56N/N55Q/Y51V, F56N/N55Q/Y51A, F56N/N55Q/Y51N, F56N/N55Q/Y51Q, F56N/N55Q/Y51S, F56N/N55Q/Y51G, F56N/N55R/Y51L, F56N/N55R/Y51V, F56N/N55R/Y51A, F56N/N55R/Y51N, F56N/N55R/Y51Q, F56N/N55R/Y51S, F56N/N55R/Y51G, F56N/N55K/Y51L, F56N/N55K/Y51V, F56N/N55K/Y51A, F56N/N55K/Y51N, F56N/N55K/Y51Q, F56N/N55K/Y51S, F56N/N55K/Y51G, F56N/N55S/Y51L, F56N/N55S/Y51V, F56N/N55S/Y51A, F56N/N55S/Y51N, F56N/N55S/Y51Q, F56N/N55S/Y51S, F56N/N55G/Y51L, F56N/N55G/Y51V, F56N/N55G/Y51A, F56N/N55G/Y51N, F56N/N55G/Y51Q, F56N/N55G/Y51S, F56N/N55G/Y51G, F56N/N55A/Y51L, F56N/N55A/Y51V, F56N/N55A/Y51A, F56N/N55A/Y51N, F56N/N55A/Y51Q, F56N/N55A/Y51S, F56N/N55A/

Y51G, F56N/N55T/Y51L, F56N/N55T/Y51V, F56N/N55T/Y51A, F56N/N55T/Y51N, F56N/N55T/Y51Q, F56N/N55T/Y51S, F56N/N55T/Y51G, F56Q/N55Q/Y51L, F56Q/N55Q/Y51V, F56Q/N55Q/Y51A, F56Q/N55Q/Y51N, F56Q/N55Q/Y51Q, F56Q/N55Q/Y51S, F56Q/N55Q/Y51G, F56Q/N55R/Y51L, F56Q/N55R/Y51V, F56Q/N55R/Y51A, F56Q/N55R/Y51N, F56Q/N55R/Y51Q, F56Q/N55R/Y51S, F56Q/N55R/Y51G, F56Q/N55K/Y51L, F56Q/N55K/Y51V, F56Q/N55K/Y51A, F56Q/N55K/Y51N, F56Q/N55K/Y51Q, F56Q/N55K/Y51S, F56Q/N55K/Y51G, F56Q/N55S/Y51L, F56Q/N55S/Y51V, F56Q/N55S/Y51A, F56Q/N55S/Y51N, F56Q/N55S/Y51Q, F56Q/N55S/Y51S, F56Q/N55S/Y51G, F56Q/N55G/Y51L, F56Q/N55G/Y51V, F56Q/N55G/Y51A, F56Q/N55G/Y51N, F56Q/N55G/Y51Q, F56Q/N55G/Y51S, F56Q/N55G/Y51G, F56Q/N55A/Y51L, F56Q/N55A/Y51V, F56Q/N55A/Y51A, F56Q/N55A/Y51N, F56Q/N55A/Y51Q, F56Q/N55A/Y51S, F56Q/N55A/Y51G, F56Q/N55T/Y51L, F56Q/N55T/Y51V, F56Q/N55T/Y51A, F56Q/N55T/Y51N, F56Q/N55T/Y51Q, F56Q/N55T/Y51S, F56Q/N55T/Y51G, F56R/N55Q/Y51L, F56R/N55Q/Y51V, F56R/N55Q/Y51A, F56R/N55Q/Y51N, F56R/N55Q/Y51Q, F56R/N55Q/Y51S, F56R/N55Q/Y51G, F56R/N55R/Y51L, F56R/N55R/Y51V, F56R/N55R/Y51A, F56R/N55R/Y51N, F56R/N55R/Y51Q, F56R/N55R/Y51S, F56R/N55R/Y51G, F56R/N55K/Y51L, F56R/N55K/Y51V, F56R/N55K/Y51A, F56R/N55K/Y51N, F56R/N55K/Y51Q, F56R/N55K/Y51S, F56R/N55K/Y51G, F56R/N55S/Y51L, F56R/N55S/Y51V, F56R/N55S/Y51A, F56R/N55S/Y51N, F56R/N55S/Y51Q, F56R/N55S/Y51S, F56R/N55S/Y51G, F56R/N55G/Y51L, F56R/N55G/Y51V, F56R/N55G/Y51A, F56R/N55G/Y51N, F56R/N55G/Y51Q, F56R/N55G/Y51S, F56R/N55G/Y51G, F56R/N55A/Y51L, F56R/N55A/Y51V, F56R/N55A/Y51A, F56R/N55A/Y51N, F56R/N55A/Y51Q, F56R/N55A/Y51S, F56R/N55A/Y51G, F56R/N55T/Y51L, F56R/N55T/Y51V, F56R/N55T/Y51A, F56R/N55T/Y51N, F56R/N55T/Y51Q, F56R/N55T/Y51S, F56R/N55T/Y51G, F56S/N55Q/Y51L, F56S/N55Q/Y51V, F56S/N55Q/Y51A, F56S/N55Q/Y51N, F56S/N55Q/Y51Q, F56S/N55Q/Y51S, F56S/N55Q/Y51G, F56S/N55R/Y51L, F56S/N55R/Y51V, F56S/N55R/Y51A, F56S/N55R/Y51N, F56S/N55R/Y51Q, F56S/N55R/Y51S, F56S/N55R/Y51G, F56S/N55K/Y51L, F56S/N55K/Y51V, F56S/N55K/Y51A, F56S/N55K/Y51N, F56S/N55K/Y51Q, F56S/N55K/Y51S, F56S/N55K/Y51G, F56S/N55S/Y51L, F56S/N55S/Y51V, F56S/N55S/Y51A, F56S/N55S/Y51N, F56S/N55S/Y51Q, F56S/N55S/Y51S, F56S/N55S/Y51G, F56S/N55G/Y51L, F56S/N55G/Y51V, F56S/N55G/Y51A, F56S/N55G/Y51N, F56S/N55G/Y51Q, F56S/N55G/Y51S, F56S/N55G/Y51G, F56S/N55A/Y51L, F56S/N55A/Y51V, F56S/N55A/Y51A, F56S/N55A/Y51N, F56S/N55A/Y51Q, F56S/N55A/Y51S, F56S/N55A/Y51G, F56S/N55T/Y51L, F56S/N55T/Y51V, F56S/N55T/Y51A, F56S/N55T/Y51N, F56S/N55T/Y51Q, F56S/N55T/Y51S, F56S/N55T/Y51G, F56G/N55Q/Y51L, F56G/N55Q/Y51V, F56G/N55Q/Y51A, F56G/N55Q/Y51N, F56G/N55Q/Y51Q, F56G/N55Q/Y51S, F56G/N55Q/Y51G, F56G/N55R/Y51L, F56G/N55R/Y51V, F56G/N55R/Y51A, F56G/N55R/Y51N, F56G/N55R/Y51Q, F56G/N55R/Y51S, F56G/N55R/Y51G, F56G/N55K/Y51L, F56G/N55K/Y51V, F56G/N55K/Y51A, F56G/N55K/Y51N, F56G/N55K/Y51Q, F56G/N55K/Y51S, F56G/N55K/Y51G, F56G/N55S/Y51L, F56G/N55S/Y51V, F56G/N55S/Y51A, F56G/N55S/Y51N, F56G/N55S/Y51Q, F56G/N55S/Y51S, F56G/N55S/Y51G, F56G/N55G/Y51L, F56G/N55G/Y51V, F56G/N55G/Y51A, F56G/N55G/Y51N, F56G/N55G/Y51Q, F56G/N55G/Y51S, F56G/N55G/Y51G, F56G/

N55A/Y51L, F56G/N55A/Y51V, F56G/N55A/Y51A, F56G/N55A/Y51N, F56G/N55A/Y51Q, F56G/N55A/Y51S, F56G/N55A/Y51G, F56G/N55T/Y51L, F56G/N55T/Y51V, F56G/N55T/Y51A, F56G/N55T/Y51N, F56G/N55T/Y51Q, F56G/N55T/Y51S, F56G/N55T/Y51G, F56A/N55Q/Y51L, F56A/N55Q/Y51V, F56A/N55Q/Y51A, F56A/N55Q/Y51N, F56A/N55Q/Y51Q, F56A/N55Q/Y51S, F56A/N55Q/Y51G, F56A/N55R/Y51L, F56A/N55R/Y51V, F56A/N55R/Y51A, F56A/N55R/Y51N, F56A/N55R/Y51Q, F56A/N55R/Y51S, F56A/N55R/Y51G, F56A/N55K/Y51L, F56A/N55K/Y51V, F56A/N55K/Y51A, F56A/N55K/Y51N, F56A/N55K/Y51Q, F56A/N55K/Y51S, F56A/N55K/Y51G, F56A/N55S/Y51L, F56A/N55S/Y51V, F56A/N55S/Y51A, F56A/N55S/Y51N, F56A/N55S/Y51Q, F56A/N55S/Y51S, F56A/N55S/Y51G, F56A/N55G/Y51L, F56A/N55G/Y51V, F56A/N55G/Y51A, F56A/N55G/Y51N, F56A/N55G/Y51Q, F56A/N55G/Y51S, F56A/N55G/Y51G, F56A/N55A/Y51L, F56A/N55A/Y51V, F56A/N55A/Y51A, F56A/N55A/Y51N, F56A/N55A/Y51Q, F56A/N55A/Y51S, F56A/N55A/Y51G, F56A/N55T/Y51L, F56A/N55T/Y51V, F56A/N55T/Y51A, F56A/N55T/Y51N, F56A/N55T/Y51Q, F56A/N55T/Y51S, F56A/N55T/Y51G, F56K/N55Q/Y51L, F56K/N55Q/Y51V, F56K/N55Q/Y51A, F56K/N55Q/Y51N, F56K/N55Q/Y51Q, F56K/N55Q/Y51S, F56K/N55Q/Y51G, F56K/N55R/Y51L, F56K/N55R/Y51V, F56K/N55R/Y51A, F56K/N55R/Y51N, F56K/N55R/Y51Q, F56K/N55R/Y51S, F56K/N55R/Y51G, F56K/N55K/Y51L, F56K/N55K/Y51V, F56K/N55K/Y51A, F56K/N55K/Y51N, F56K/N55K/Y51Q, F56K/N55K/Y51S, F56K/N55K/Y51G, F56K/N55S/Y51L, F56K/N55S/Y51V, F56K/N55S/Y51A, F56K/N55S/Y51N, F56K/N55S/Y51Q, F56K/N55S/Y51S, F56K/N55S/Y51G, F56K/N55G/Y51L, F56K/N55G/Y51V, F56K/N55G/Y51A, F56K/N55G/Y51N, F56K/N55G/Y51Q, F56K/N55G/Y51S, F56K/N55G/Y51G, F56K/N55A/Y51L, F56K/N55A/Y51V, F56K/N55A/Y51A, F56K/N55A/Y51N, F56K/N55A/Y51Q, F56K/N55A/Y51S, F56K/N55A/Y51G, F56K/N55T/Y51L, F56K/N55T/Y51V, F56K/N55T/Y51A, F56K/N55T/Y51N, F56K/N55T/Y51Q,F56K/N55T/Y51S, F56K/N55T/Y51G, F56E/N55R, F56E/N55K, F56D/N55R, F56D/N55K, F56R/N55E, F56R/N55D, F56K/N55E or F56K/N55D.

In (ii), the variant preferably comprises Y51R/F56Q, Y51N/F56N, Y51M/F56Q, Y51L/F56Q, Y51I/F56Q, Y51V/F56Q, Y51A/F56Q, Y51P/F56Q, Y51G/F56Q, Y51C/F56Q, Y51Q/F56Q, Y51N/F56Q, Y51S/F56Q, Y51E/F56Q, Y51D/F56Q, Y51K/F56Q or Y51H/F56Q.

In (ii), the variant preferably comprises Y51T/F56Q, Y51Q/F56Q or Y51A/F56Q.

In (ii), the variant preferably comprises Y51T/F56F, Y51T/F56M, Y51T/F56L, Y51T/F56I, Y51T/F56V, Y51T/F56A, Y51T/F56P, Y51T/F56G, Y51T/F56C, Y51T/F56Q, Y51T/F56N, Y51T/F56T, Y51T/F56S, Y51T/F56E, Y51T/F56D, Y51T/F56K, Y51T/F56H or Y51T/F56R.

In (ii), the variant preferably comprises Y51T/N55Q, Y51T/N55S or Y51T/N55A.

In (ii), the variant preferably comprises Y51A/F56F, Y51A/F56L, Y51A/F56I, Y51A/F56V, Y51A/F56A, Y51A/F56P, Y51A/F56G, Y51A/F56C, Y51A/F56Q, Y51A/F56N, Y51A/F56T, Y51A/F56S, Y51A/F56E, Y51A/F56D, Y51A/F56K, Y51A/F56H or Y51A/F56R.

In (ii), the variant preferably comprises Y51C/F56A, Y51E/F56A, Y51D/F56A, Y51K/F56A, Y51H/F56A, Y51Q/F56A, Y51N/F56A, Y51S/F56A, Y51P/F56A or Y51V/F56A.

In (xi), the variant preferably comprises deletion of Y51/P52, Y51/P52/A53, P50 to P52, P50 to A53, K49 to Y51, K49 to A53 and replacement with a single proline (P), K49 to S54, Y51 to A53, Y51 to S54, N55/F56, N55 to S57, N55/F56 and replacement with a single P, N55/F56 and replacement with a single glycine (G), N55/F56 and replacement with a single alanine (A), N55/F56 and replacement with a single P and Y51N, N55/F56 and replacement with a single P and Y51Q, N55/F56 and replacement with a single P and Y51S, N55/F56 and replacement with a single G and Y51N, N55/F56 and replacement with a single G and Y51Q, N55/F56 and replacement with a single G and Y51S, N55/F56 and replacement with a single A and Y51N, N55/F56 and replacement with a single A/Y51Q or N55/F56 and replacement with a single A and Y51S.

Preferred variants of SEQ ID NO: 32 are disclosed in International Application No. PCT/EP2015/069965.

A variant of SEQ ID NO: 32 is a protein that has an amino acid sequence which varies from that of SEQ ID NO: 32 and which retains its pore forming ability. The ability of a variant to form a pore can be assayed using any method known in the art and described above.

Over the entire length of the amino acid sequence of SEQ ID NO: 32, a variant will preferably be at least 50% homologous to that sequence based on amino acid similarity or identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid similarity or identity to the amino acid sequence of SEQ ID NO: 32 over the entire sequence. There may be at least 80%, for example at least 85%, 90% or 95%, amino acid similarity or identity over a stretch of 200 or more, for example 230, 250, 270 or 280 or more, contiguous amino acids ("hard homology"). Homology can be determined as discussed below.

Amino acid substitutions may be made to the amino acid sequence of SEQ ID NO: 4, 31 or 32 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4, 31 or 32 may additionally be deleted from the polypeptides described above. Up to 1, 2, 3, 4, 5, 10, 20 or 30 residues may be deleted, or more.

Variants may be fragments of SEQ ID NO: 4, 31 or 32. Such fragments retain pore-forming activity. Fragments may be at least 50, 100, 200 or 250 amino acids in length. A fragment preferably comprises the pore-forming domain of SEQ ID NO: 4, 31 or 32. Fragments typically include residues 119, 121, 135. 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4, 31 or 32 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4, 31 or 32 is a subunit that has an amino acid sequence which varies from that of SEQ ID NO: 4, 31 or 32 and which retains its ability to form a pore. A variant typically contains the regions of SEQ ID NO: 4, 31 or 32 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4, 31 or 32 preferably includes one or more modifications, such as substitutions, additions or deletions, within its α-helices and/or loop regions. Amino acids that form α-helices and loops are discussed above.

The variant of SEQ ID NO: 4, 31 or 32 may be modified to affects its oligomerisation and/or to assist its identification or purification as discussed below.

In some embodiments, the hetero-oligomeric pore is chemically modified. The pore can be chemically modified in any way and at any site. Suitable modifications are discussed below. Such modifications can be applied to any of the pores produced in the invention.

Constructs

The hetero-oligomeric pore of the invention may comprise a construct comprising two or more covalently attached monomers. The first different monomer may form part of a first different construct comprising two or more genetically fused monomers. The second different monomer may form part of a second different construct comprising two or more genetically fused monomers. The first and second different constructs may differ from one another in any of the ways discussed above and below.

The first different construct and second different construct retain their ability to form a pore. This may be determined as discussed above. Each construct may comprise at least 2, at least 3, at least 4, at least 5, at least 6, at least 7, at least 8, at least 9 or at least 10 monomers. Each construct preferably comprises two monomers. The two or more monomers may be the same or different.

The monomers in the construct are preferably approximately the same length or are the same length. The barrels of the monomers in the construct are preferably approximately the same length or are the same length. Length may be measured in number of amino acids and/or units of length. The monomers in the construct preferably have the same number of amino acids deleted from the barrel, such as from positions 72 to 82 and/or positions 111 to 121 in MspA (SEQ ID NO: 2). As discussed below, one or more of the different constructs may be attached to a tag or BasTL sequence or fragment thereof which makes it longer than the other constructs in the pore.

The monomers in the construct are genetically fused. Monomers are genetically fused if the whole construct is expressed from a single polynucleotide sequence. The coding sequences of the monomers may be combined in any way to form a single polynucleotide sequence encoding the construct.

The monomers may be genetically fused in any configuration. The monomers may be fused via their terminal amino acids. For instance, the amino terminus of the one monomer may be fused to the carboxy terminus of another monomer. The second and subsequent monomers in the construct (in the amino to carboxy direction) may comprise a methionine at their amino terminal ends (each of which is fused to the carboxy terminus of the previous monomer). For instance, if M is a monomer (without an amino terminal methionine) and mM is a monomer with an amino terminal methionine, the construct may comprise the sequence mM-mM, mMmM-mM or mM-mM-mM-mM. The presences of these methionines typically results from the expression of the start codons (i.e. ATGs) at the 5' end of the polynucleotides encoding the monomers within the polynucleotide encoding the entire construct. The second and subsequent monomer in the construct (in the amino to carboxy direction) may lack a methionine (e.g. mM-M, mM-M-M or mM-M-M-M).

The two or more monomers may be genetically fused directly together. The monomers are preferably genetically fused using a linker. The linker may be designed to constrain the mobility of the monomers. Preferred linkers are amino acid sequences (i.e. peptide linkers). Any of the peptide linkers discussed below may be used.

The pore contains sufficient constructs and, if necessary, monomers to form the pore. For instance, an octameric pore may comprise (a) four constructs each comprising two monomers, (b) two constructs each comprising four monomers or (b) one construct comprising two monomers and six monomers that do not form part of a construct. For instance, a nonameric pore may comprise (a) four constructs each comprising two monomers and one monomer that does not form part of a construct, (b) two constructs each comprising four monomers and a monomer that does not form part of a construct or (b) one construct comprising two monomers and seven monomers that do not form part of a construct. Other combinations of constructs and monomers can be envisaged by the skilled person.

A pore of the invention typically contains (a) one construct comprising two monomers and (b) 5, 6, 7 or 8 monomers. The construct may be any of those discussed above.

Another typical pore comprises more than one construct of the invention, such as two, three or four constructs of the invention. If necessary, such pores further comprise sufficient additional monomers or constructs to form the pore. The additional monomer(s) may be any of those discussed above.

A further pore of the invention comprises only constructs comprising 2 monomers, for example a pore may comprise 4, 5, 6, 7 or 8 constructs comprising 2 monomers.

One or more of the constructs may be chemically-modified as discussed above. In all of the discussion below, embodiments which relate to first different monomer and/or the second different monomer, especially the specific stoichiometric ratios, equally apply to the first different construct and/or and second different construct. The term monomer and construct are interchangeable in all of the discussion below.

Specific Stoichiometric Ratio

The hetero-oligomeric pore produced by the method of the invention comprises two different monomers in a specific stoichiometric ratio. The specific stoichiometric ratio is typically pre-determined. It may also be called the desired stoichiometric ratio.

The specific stoichiometric ratio is the ratio of the first different monomer to the second different monomer in the hetero-oligomeric pore. If the hetero-oligomeric pore comprises 3 monomers, the specific stoichiometric ratio of the first different monomer to the second different monomer may be 1:2 or 2:1. If the hetero-oligomeric pore comprises 4 monomers, the specific stoichiometric ratio of the first different monomer to the second different monomer may be 1:3, 2:2 or 3:1. If the hetero-oligomeric pore comprises 5 monomers, the specific stoichiometric ratio of the first different monomer to the second different monomer may be 1:4, 2:3, 3:2 or 4:1. If the hetero-oligomeric pore comprises 6 monomers, the specific stoichiometric ratio of the first different monomer to the second different monomer may be 1:5, 2:4, 3:3, 4:2 or 5:1. If the hetero-oligomeric pore comprises 7 monomers, the specific stoichiometric ratio of the first different monomer to the second different monomer may be 1:6, 2:5, 3:4, 4:3, 5:2 or 6:1. If the hetero-oligomeric pore comprises 8 monomers, the specific stoichiometric ratio of the first different monomer to the second different monomer may be 1:7, 2:6, 3:5, 4:4, 5:3, 6:2 or 7:1. If the hetero-oligomeric pore comprises 9 monomers, the specific stoichiometric ratio of the first different monomer to the second different monomer may be 1:8, 2:7, 3:6, 4:5, 5:4, 6:3, 7:2 or 8:1. If the hetero-oligomeric pore comprises 10 monomers, the specific stoichiometric ratio of the first different monomer to the second different monomer may be 1:9, 2:8, 3:7, 4:6, 5:5, 6:4, 7:3, 8:2 or 9:1.

The specific stoichiometric ratio of the first different monomer to the second different monomer is at least 5:1, such as at least 6:1, at least 7:1, at least 8:1 or at least 9:1. The specific stoichiometric ratio of the first different monomer to the second different monomer is most preferably 6:1 or 7:1.

The method of the invention produces a hetero-oligomeric pore comprising two different monomers in a specific stoichiometric ratio. This means that the majority of the pores produced in the cell comprise the two different monomers in the specific stoichiometric ratio. For instance, at least 55% of the hetero-oligomeric pores produced by the cell comprise the two different monomers in the specific stoichiometric ratio. At least 60%, such at least 65%, at least 70%, at least 75%, at least 80%, at least 85%, at least 90%, at least 95%, at least 97%, at least 98% or at least 99%, of the hetero-oligomeric pores produced by the cell comprise the two different monomers in the specific stoichiometric ratio. In some instances, all, i.e. 100%, of the hetero-oligomeric pores produced by the cell comprise the two different monomers in the specific stoichiometric ratio. The % of hetero-oligomeric pores produced by the cell which comprise the two different monomers in the specific stoichiometric ratio can be measured using methods in the art. For instance, if one of the different monomers is tagged as discussed below, hetero-oligomeric pores comprising different ratios of the different monomers will have different sizes. The different sized hetero-oligomeric pores can be identified and quantified using gel electrophoresis.

Vectors

The method of the invention comprises transfecting or transforming a cell with the two different monomers. Transfection or transformation involves the introduction of a polynucleotide, such as a nucleic acid, into the cell. Transfection or transformation typically concerns non-viral methods.

The cell is transfected or transformed with the first different monomer in a first inducible vector or first inducible expression vector. The cell is also transfected or transformed with the second different monomer in a second inducible vector or second inducible expression vector. The method may comprise transfecting or transforming the cell with the first and second inducible vectors or inducible expression vectors in any order. The method may comprise transfecting or transforming the cell with the first inducible vector or first inducible expression vector before the second inducible vector or the second inducible expression vector. The method may comprise transfecting or transforming the cell with the second inducible vector or second inducible expression vector before the first inducible vector or the first inducible expression vector. The method may comprise transfecting or transforming the cell with the first and second inducible vectors or inducible expression vectors at the same time. Before the first and second inducible vectors are induced such that the cell produces the hetero-oligomeric pore comprising the first and second different monomers in the specific stoichiometric ratio, the cell is transfected or transformed with both the first and second inducible vectors or inducible expression vectors.

The cell is typically transfected or transformed with a polynucleotide sequence encoding the first different monomer in a first inducible vector or first inducible expression vector. The cell is also typically transfected or transformed with a polynucleotide sequence encoding the second different monomer in a second inducible vector or second inducible expression vector.

Polynucleotide sequences conceding the monomers may be derived and replicated using standard methods in the art. Chromosomal DNA encoding wild-type pores may be extracted from a pore producing organism, such as *Staphyloccoccus aureus, Mycobacterium smegmatis* or *Escherichia coli*. The gene encoding the pore subunit may be amplified using PCR involving specific primers. The amplified sequence may then undergo site-directed mutagenesis. Suitable methods of site-directed mutagenesis are known in the art and include, for example, combined chain reaction. Polynucleotides can be made using well-known techniques, such as those described in Sambrook, J. and Russell, D. (2001). Molecular Cloning: A Laboratory Manual, 3rd Edition. Cold Spring Harbor Laboratory Press, Cold Spring Harbor, N.Y. They can also be obtained commercially.

The resulting polynucleotide sequence may then be incorporated into a recombinant replicable vector such as a cloning vector. The vector may be used to replicate the polynucleotide in a compatible host cell. Thus polynucleotide sequences may be made by introducing a polynucleotide into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into suitable expression vector. In an expression vector, the polynucleotide sequence is typically operably linked to a control sequence which is capable of providing for the expression of the coding sequence by the host cell. Such expression vectors can be used to express a monomer. The polynucleotide sequence encoding the first different monomer is preferably operably linked to a first inducible control sequence, such as a first inducible promoter, in the first inducible vector or first inducible expression vector. The polynucleotide sequence encoding the second different monomer is preferably operably linked to a second inducible control sequence, such as a second inducible promoter, in the second inducible vector or second inducible expression vector.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide sequences may be introduced into the vector.

The first inducible vector and the second inducible vector are typically inducible because they each comprise an inducible promoter. The first inducible vector typically comprises a first inducible promoter and the second inducible vector typically comprises a second inducible promoter. The first and/or second inducible promoter may be an arabinose promoter, a proprionate promoter, a rhamnose-inducible promoter, a xylose promoter or a lactose promoter. The polynucleotide sequence encoding the first different monomer is preferably operably linked to an arabinose promoter, a proprionate promoter, a rhamnose-inducible promoter, a xylose promoter or a lactose promoter. The polynucleotide sequence encoding the second different monomer is preferably operably linked to an arabinose promoter, a proprionate promoter, a rhamnose-inducible promoter, a xylose promoter or a lactose promoter.

The promoters in the first inducible vector and the second inducible vector are preferably different. The first inducible vector preferably comprises a rhamnose-inducible promoter and the second inducible vector comprises a lactose promoter. The polynucleotide sequence encoding the first different monomer is preferably operably linked to a rhamnose-inducible promoter and the polynucleotide sequence encoding the second different monomer is preferably operably linked to a lactose promoter. The first inducible vector or first inducible promoter is preferably induced by rhamnose. The second inducible vector or the second inducible promoter is preferably induced by Isopropyl β-D-thiogalactopyranoside (IPTG).

The first and second inducible vectors are preferably differentially inducible. Differential inducibility is discussed in more detail below.

The first inducible vector and/or the second inducible vector may be for example, plasmid, virus or phage vectors. The first inducible vector and/or the second inducible vector may comprise an origin of replication.

The first inducible vector and/or the second inducible vector may contain one or more selection marker genes, for example a tetracycline resistance gene, triclosan resistance gene, ampicillin resistance gene or kanamycin resistance gene. The first inducible vector preferably comprises a first selection marker and the second inducible vector preferably comprises a second selection marker. The first and second selection markers are preferably different from one another. If the selection markers are different, it is straightforward to confirm that the cell has been transfected or transformed with both vectors. The first selection marker is preferably a gene providing resistance to kanamycin. The second selection marker is preferably a gene providing resistance to ampicillin.

The cell transfected or transformed in accordance with the invention may be referred to as the host cell. The method may comprise contacting the cell with the first and second inducible vectors under conditions which will transfect or transform the cell. Suitable conditions are known in the art (see, for instance, Sambrook, J. and Russell, D. supra).

The cell typically expresses the first and/or second different monomers at a high level. Cells will typically be chosen to be compatible with the expression vectors used to transfect or transform the cell. Suitable cells for use in the invention include prokaryotic cells and eukaryotic cells. The prokaryotic cell is preferably a bacterial cell. Suitable bacterial cells include, but are not limited to, *Escherichia coli, Corynebacterium* and *Pseudomonas fluorescens*. Any *E. coli* cell with a DE3 lysogen, for example C41 (DE3), BL21 (DE3), JM109 (DE3), B834 (DE3), TUNER, Origami and Origami B, can express a vector comprising the T7 promoter.

Suitable eukaryotic cells include, but are not limited to, *Saccharomyces cerevisiae, Pichia pastoris*, filamentous fungi, such as *Aspergillus, Trichoderma* and *Myceliophthora*

*thermophila* C1, baculovirus-infected insect cells, such as Sf9, Sf21 and High Five strains, non-lytic insect cells, *Leishmania* cells, plant cells, such as tobacco plant cells, and mammalian cells, such as *Bos primigenius* cells (Bovine), *Mus musculus* cells (Mouse), Chinese Hamster Ovary (CHO) cells, Human Embryonic Kidney (HEK) cells, Baby Hamster Kidney (BHK) cells and HeLa cells. Other preferred mammalian cells include, but are not limited to, PC12, HEK293, HEK293A, HEK293T, CHO, BHK-21, HeLa, ARPE-19, RAW264.7 and COS cells.

The host cell is preferably *Escherichia coli.*

The recombinantly-expressed first and second different monomers typically self-assemble into a hetero-oligomeric pore in the cell membrane. In step (c), the first and second monomers are preferably expressed in the cell in the specific stoichiometric ratio and the hetero-oligomeric pore forms in cell membrane.

Differential Induction

The method preferably comprises differentially inducing the first and second inducible vectors. This typically involves inducing the first and second inducible vectors in different ways. For instance, the first inducible vector may be induced by rhamnose and the second inducible vector may be induced by isopropyl β-D-thiogalactopyranoside (IPTG). A skilled person can perform control experiments to determine the effect of differential induction on the stoichiometric ratio of the first and second different monomers in the hetero-oligomeric pore.

The method preferably comprises inducing the first and second inducible vectors to differing extents. This typically involves inducing the first and second inducible vectors to differing degrees. The first and second inducible vectors are typically induced to differing extents or degrees using different concentrations of the inducing chemicals or molecules. A skilled person can perform control experiments to determine the effect of inducing the vectors to differing degrees or extents on the stoichiometric ratio of the first and second different monomers in the hetero-oligomeric pore.

The first and second inducible vectors may be differentially induced to differing extents.

Ratio of Expression

The hetero-pore produced using the invention may comprise the first and second different monomers in the specific stoichiometric ratio because the cell expresses the first and second different monomers in a specific ratio. In step (c), the first and second different monomers are preferably expressed by the cell in a ratio that allows the formation of the hetero-oligomeric pore comprising the first and second different monomers in the specific stoichiometric ratio. However, the first and second different monomers do not need to be expressed in the specific stoichiometric ratio. The ratio in which the first and second different monomers are expressed may allow the formation of different hetero-oligomeric pores comprising different ratios of the first and second different monomers including the specific stoichiometric ratio. For instance, if the hetero-oligomeric pore comprises 8 monomers and the specific stoichiometric ratio of the first different monomer to the second different monomer is 7:1, the different monomers may be expressed in a ratio that allows the formation of the hetero-oligomeric pores comprising the first and second different monomers in ratio 6:2, 7:1 and 8:0. The hetero-oligomeric pore having the specific stoichiometric ratio may be purified as discussed in more detail below.

The ratio of expression of the first different monomer to the second different monomer can be measured using routine methods, such as SDS-PAGE, western blotting or mass spectroscopy. The ratio of expression can be affected by differentially inducing the first and second inducible vectors and/or inducing them to different extents as discussed above.

The ratio of expression of the first and second different monomers may also be affected by modifying one or both of them. At least one of, such as both of, the first and second different monomers is preferably modified to affect its expression compared with its expression in the absence of the modification. The first different monomer may be modified to increase or decrease its expression compared with its expression in the absence of the modification. The second different monomer may be modified to increase or decrease its expression compared with its expression in the absence of the modification. Preferred combinations of modification or lack thereof are shown in Table 1 below.

TABLE 1

| First different monomer | Second different monomer |
| --- | --- |
| Modification which increases its expression | No modification |
| No modification | Modification which increases its expression |
| Modification which decreases its expression | No modification |
| No modification | Modification which decreases its expression |
| Modification which increases its expression | Modification which decreases its expression |
| Modification which decreases its expression | Modification which increases its expression |
| Modification which increases its expression | Modification which increases its expression |
| Modification which decreases its expression | Modification which decreases its expression |

The expression of the first different monomer and/or second different monomer can be affected to any degree. For instance, the expression of the first different monomer and/or second different monomer can be increased or decreased by at least 5%, such as by at least 10%, at least 20%, at least 30%, at least 40%, at least 50%, at least 60%, at least 70%, at least 80%, at least 90%, at least 100%, at least 150%, at least 200%, at least 300%, at least 400%, at least 500%. The level of expression of a monomer can be determined using routine methods, such as SDS-PAGE, western blotting, UV280 concentration measurement or mass spectroscopy. The ability of a modification to affect the expression of a monomer can be determined by comparing the expression of the modified monomer with the expression of the unmodified monomer in the same cell under the same conditions.

Increasing or decreasing the expression of the two monomers to different extents can help to ensure that the monomers are expressed in approximately the specific stoichiometric ratio.

A skilled person will be able to design modifications which affect the expression of the monomer(s). The modification is preferably the genetic fusion of a peptide, polypeptide or protein sequence to the monomer such that the peptide, polypeptide or protein sequence is expressed with the monomer. The monomer and the peptide, polypeptide or protein sequence are genetically fused if they are expressed from a single polynucleotide sequence. Preferred methods of decreasing the expression of a monomer are discussed in more detail below with reference to tags.

Modification which Affects Oligomerisation

The hetero-pore produced using the invention may comprise the first and second different monomers in the specific stoichiometric ratio because one or both of the first and second different monomers are modified to affect their ability to oligomerise. At least one of, such as both of, the first and second different monomers is preferably modified to affect its ability to oligomerise with itself or the other different monomer. The first different monomer may be modified to increase or decrease its ability to oligomerise with the second different monomer. The second different monomer may be modified to increase or decrease its ability to oligomerise with the first different monomer. Increasing the ability of a monomer to oligomerise will increase its incidence in the hetero-oligomeric pores produced using the method and can therefore influence the specific stoichiometric ratio. Conversely, decreasing the ability of a monomer to oligomerise will decrease its incidence in the hetero-oligomeric pores produced using the method.

Preferred combinations of modifications or a lack thereof are shown in the Table 2 below.

TABLE 2

| First different monomer | Second different monomer |
| --- | --- |
| Modification which increases its ability to oligomerise | No modification |
| No modification | Modification which increases its ability to oligomerise |
| Modification which decreases its ability to oligomerise | No modification |
| No modification | Modification which decreases its ability to oligomerise |
| Modification which increases its ability to oligomerise | Modification which decreases its ability to oligomerise |
| Modification which decreases its ability to oligomerise | Modification which increases its ability to oligomerise |
| Modification which increases its ability to oligomerise | Modification which increases its ability to oligomerise |
| Modification which decreases its ability to oligomerise | Modification which decreases its ability to oligomerise |

The ability of the first different monomer and/or second different monomer to oligomerise with the other monomer can be affected to any degree. For instance, the ability of the first different monomer and/or second different monomer to oligomerise with the other monomer can be increased or decreased by at least 5%, such as by at least 10%, at least 20%, at least 30%, at least 40%, at least 50%, at least 60%, at least 70%, at least 80%, at least 90%, at least 100%, at least 150%, at least 200%, at least 300%, at least 400%, at least 500%. The ability of a monomer to oligomerise can be determined using routine methods such as SDS-PAGE, western blotting, UV280 concentration measurement, size exclusion chromatography or mass spectroscopy. The ability of a modification to affect the oligomerisation of a monomer can be determined by comparing the oligomerisation of the modified monomer with the oligomerisation of the unmodified monomer with the same monomer under the same conditions.

Increasing or decreasing the ability of the two monomers to oligomerise to different extents can help to ensure that the hetero-oligomeric pore comprises the two different monomers in the specific stoichiometric ratio.

A skilled person will be able to design modifications which affect the ability of the monomer(s) to oligomerise. The modification is preferably the genetic fusion of a peptide, polypeptide or protein sequence to the monomer such that the peptide, polypeptide or protein sequence is expressed with the monomer. Genetic fusion is defined above. Genetic fusion may be at the amino (N) and/or carboxy (C) terminus of the monomer(s). Preferred methods of decreasing the ability of a monomer to oligomerise are discussed in more detail below with reference to tags. The modification is preferably a truncation of the monomer(s). The truncation may be at the amino (N) and/or carboxy (C) terminus of the monomer(s). The modification is preferably one or more mutations of the amino acids/regions of the monomer(s) responsible for oligomerisation.

The amino acids and regions of Staphylococcal alpha-hemolysin responsible for oligomerisation are known in the art. Walker and Bayley, Journal of Biological Chemistry, Vol. 270, No. 39, Issue of September 29, pp. 23065-23071, 1995 discloses key Residues for membrane binding, oligomerisation, and pore forming activity of Staphylococcal alpha-hemolysin identified by cysteine scanning mutagenesis and targeted chemical modification. Panchal and Bayley, Journal of Biological Chemistry, Vol. 270, No. 39, Issue of September 29, pp. 23072-23076, 1995 discloses interactions between residues in Staphylococcal alpha-hemolysin revealed by reversion mutagenesis. Cheley et al., Protein Engineering vol. 10 no. 12 pp. 1433-1443, 1997 discloses spontaneous oligomerisation of a staphylococcal a-hemolysin conformationally constrained by removal of residues that form the transmembrane beta-barrel. Jayasinghe et al., The Journal Of Biological Chemistry Vol. 281, No. 4, pp. 2195-2204, Jan. 27, 2006 discloses the role of the amino latch of Staphylococcal alpha-hemolysin in pore formation and reveals a co-operative interaction between the n terminus and position 217.

Tags

Tags may also be used to allow the first and second different monomers to be expressed in the cell in the specific stoichiometric ratio and/or to affect the ability of the monomer to oligomerise. The tag is preferably a peptide or a polypeptide. One or more peptide or polypeptide tags may be genetically fused to the first and/or second different monomer. The monomer and the tag(s) are genetically fused if they are expressed from a single polynucleotide sequence. The presence of the one or more tags may increase or decrease the ability of a different monomer to be expressed. The presence of the one or more tags may increase or decrease the ability of a different monomer to oligomerise with itself or the other monomers in the hetero-oligomeric pore.

The second different monomer is preferably genetically fused to a peptide or polypeptide tag which reduces its ability to oligomerise with itself or reduces its expression compared with its expression in the absence of the tag. The peptide or polypeptide tag is preferably genetically fused at the carboxy (C) terminus of the second different monomer and reduces its ability to oligomerise with itself. The ability of the second different monomer to oligomerise in the presence and absence of the tag can be measured as discussed above.

The peptide or polypeptide tag is preferably genetically fused at the amino (N) terminus of the second different monomer and reduces its expression compared with its expression in the absence of the tag. The expression of the second different monomer in the presence and absence of the tag can be measured as discussed above.

The peptide or polypeptide tag may be any length. The peptide is preferably 1, 2, 3, 4 or 5 amino acids in length. The polypeptide is preferably greater than 5 amino acids in length, such as 8, 10, 12, 20, 30, 40, 50 or 100 amino acids in length or more. The peptide or polypeptide may comprise any naturally-occurring or non-naturally occurring amino acids.

The tag preferably comprises two or more consecutive arginine (R) residues or aspartic acid (D) residues. The tag more preferably comprises (a) 1, 2, 3, 4, 5, 6, 7, 8, 9, 10, 11, 12, 13, 14, 15, 16, 17, 18, 19 or 20 consecutive arginine (R) residues or aspartic acid (D) residues and/or (b) 1, 2, 3, 4, 5, 6, 7, 8, 9, 10, 11, 12, 13, 14, 15, 16, 17, 18, 19 or 20 consecutive histidine (H) residues. The tag most preferably comprises (a) 4, 6, 8, or 10 consecutive arginine (R) residues or aspartic acid (D) residues and/or (b) 6 or 9 consecutive histidine (H) residues.

The tag preferably further comprises serine-glycine (SG), asparagine-glycine-aspartic acid-serine (NGDS) or glycine-aspartic acid-serine-glycine (GDSG).

Preferred tags include, but are not limited to, R8SG, D6SG, R6SG, R8, NGDSD6SG, D4SG, R4SG, D4, D6, GDSGD4SG, R4H6, D4H6, D8, R6, D10, R4, D4, D8H6, R8H9, D10H6, R6H6 and D6.

The second different monomer preferably has one of the following tags genetically fused at its amino (N) terminus: R8SG, D6SG, R6SG, R8, NGDSD6SG, D4SG, R4SG, D4, D6 and GDSGD4SG. The second different monomer preferably has one of the following tags genetically fused at its carboxy (C) terminus: R4H6, D4H6, D8, R6, D10, R4, D4, D8H6, R8, R8H9, D10H6, R6H6 and D6. The second different monomer preferably has one of the following tags genetically fused at its carboxy (C) terminus: D4H6, D8, D10, D4, D8H6, R8, R8H9, D10H6, R6H6 and D6.

The method of the invention preferably further comprises (d) purifying the hetero-oligomeric pore comprising the two different monomers in the specific stoichiometric ratio using the tag. For instance, consecutive histidine (H) residues (a hist-tag) may be used to purify the two different monomers in the specific stoichiometric ratio. For instance, if the hetero-oligomeric pore comprises 8 monomers, the specific stoichiometric ratio of the first different monomer to the second different monomer is 7:1 and the second different monomer is genetically fused to a his-tag, the his-tag may be used to purify pores containing the first and second different monomers in the ratio of 7:1. Pores containing the first and second different monomers in the ratio 8:0 if the his-tag is used and the elution concentration of the his-tag can be designed such that the different monomers are not purified in the ratio of 6:2.

The second different monomer is preferably genetically fused to the BasTL sequence (SEQ ID NO: 26) or a fragment thereof. This may increase or decrease the ability of the second different monomer to oligomerise with itself compared with the absence of the BasTL sequence (SEQ ID NO: 26) or a fragment thereof. The fragment may be any length, such as 40 or more, 50 or more, 60 or more, 70 or more, 80 or more or 90 or more amino acids in length. The fragment preferably comprises consecutive amino acids in the BasTL sequence (SEQ ID NO: 26). The fragment is preferably formed by deletion of 20 amino acids or 40 amino acids from the carboxy (C) terminus end. The BasTL sequence or fragment thereof is preferably genetically fused at the carboxy (C) terminus of the second different monomer. The BasTL sequence or fragment thereof is preferably genetically fused at the carboxy (C) terminus of the second different monomer and separates a tag as defined above from the second different monomer. For instance, the second different monomer may have the following structure from N to C: Monomer-SEQ ID NO: 26-H6.

Hetero-Oligomeric Pores

The invention provides hetero-oligomeric pores produced using the method of the invention. Any of the embodiments discussed above apply to the pores of the invention.

The pores have improved polynucleotide reading properties i.e. display improved polynucleotide capture and nucleotide discrimination. In particular, the pores of the invention capture nucleotides and polynucleotides more easily than the wild type. In addition, the pores of the invention display an increased current range, which makes it easier to discriminate between different nucleotides, and a reduced variance of states, which increases the signal-to-noise ratio. In addition, the number of nucleotides contributing to the current as the polynucleotide moves through pores constructed from the mutants is decreased. This makes it easier to identify a direct relationship between the observed current as the polynucleotide moves through the pore and the polynucleotide sequence. The pores of the invention may also display improved movement of the polynucleotide as discussed in more detail below.

The pores of the invention can also discriminate between different nucleotides under a range of conditions. In particular, the pores will discriminate between nucleotides under conditions that are favourable to the characterising, such as sequencing, of nucleic acids. The extent to which the pores of the invention can discriminate between different nucleotides can be controlled by altering the applied potential, the salt concentration, the buffer, the temperature and the presence of additives, such as urea, betaine and DTT. This allows the function of the pores to be fine-tuned, particularly when sequencing. This is discussed in more detail below. The pores of the invention may also be used to identify polynucleotide polymers from the interaction with one or more monomers rather than on a nucleotide by nucleotide basis.

In general, the main advantage of hetero-oligomeric pores over homo-oligomeric pores is the ability to change, alter or mutate one or more of the monomers of the pore relative to (or differently from) the other monomers. Any part of the one or more monomers may be altered or mutated, for instance the part of the one or more monomers which forms the part of the pore which interacts with the polynucleotide or the part of the one or more monomers which forms the top of the pore and which interacts with a polynucleotide binding protein. By mutating the pore asymmetrically (i.e. differently in one or more of the monomers), the range, shape and level of the current signal obtained from the pore, as well as the signal to noise ratio, can be altered in a way that cannot be achieved by mutating all of the monomers.

A pore of the invention may be isolated, substantially isolated, purified or substantially purified. A pore of the invention is isolated or purified if it is completely free of any other components, such as lipids or other pores. A pore is substantially isolated if it is mixed with carriers or diluents which will not interfere with its intended use. For instance, a pore is substantially isolated or substantially purified if it is present in a form that comprises less than 10%, less than 5%, less than 2% or less than 1% of other components, such as triblock copolymers, lipids or other pores. Alternatively, a pore of the invention may be present in a membrane. Suitable membranes are discussed below.

A pore of the invention may be present as an individual or single pore. Alternatively, a pore of the invention may be present in a homologous or heterologous population of two or more pores.

The pores of the invention are hetero-oligomeric. The hetero-oligomeric pore contains sufficient monomers to form the pore. The monomers may be of any type. The pore typically comprises at least 3, at least 4, at least 5, at least 6, at least 7, at least 8, at least 9, at least 10 monomers, at least 11 monomers, at least 12 monomers, at least 13 monomers or at least 14 monomers, such as 3, 4, 5, 6, 7, 8, 9, 10, 11, 12, 13 or 14 monomers. The pore preferably comprises seven, eight or nine monomers.

A pore is hetero-oligomeric if at least one of the monomers differs from the rest of the monomers in the pore. The at least one monomer may be different in any way. The at least one monomer is typically different from the others on the basis of its amino acid sequence. The at least one monomer may be different from the rest of the monomers on the basis of 1, 2, 3, 4, 5, 10, 15, 20 or more amino acid differences. Two, three or four of the monomers may be the same and different from the rest of the monomers in the pore. All of the monomers in the pore may be different from one another. Preferably, only one monomer is different from the rest of the monomers in the pore, i.e. the rest of the monomers are the same.

The hetero-oligomeric pore is preferably derived from Msp and comprises a narrowing having a net negative charge. Such pores are disclosed in the UK Application 1502809.5 being co-filed with this application. Preferably, only one monomer is different from the rest of the monomers in the pore and the only one monomer differs from the rest of the monomers on the basis of one or more negatively charged amino acids in its region which forms part of the narrowing.

The narrowing has a net negative charge. The narrowing is typically the narrowest part of the channel of the pore. The narrowing of the pore is typically not part of the cap region or the barrel region. The internal diameter of the narrowing (i.e. the diameter of the channel through the narrowing) is typically about 25 angstroms (Å) or less, such as about 22 Å or less, about 20 Å or less, about 18 Å or less, about 16 Å or less, about 14 Å or less or about 12 Å or less.

The narrowing has a net negative charge. The narrowing has a net negative charge at physiological pH. The narrowing typically has a net negative charge when the pH is in the range of 2 to 12, 2.5 to 11, 3 to 10, more preferably in the range of 4 to 9, 5 to 8.5 or even more preferably in the range of 6 to 8 or 6.5 to 7.5.

The net charge of the narrowing can be measured using methods known in the art. For instance, the net charge of the narrowing can be calculated at a specific pH using routine methods.

The narrowing typically comprises one or more negatively charged amino acids. The narrowing may comprise any number of negatively charged amino acids, such as 1, 2, 3, 4, 5, 6, 7, 8, 9, 10, 11, 12 or more negatively charged amino acids. The narrowing preferably comprises one, two, three or four negatively charged amino acids. A negatively charged amino acid is an amino acid with a net negative charge. Negatively charged amino acids include, but are not limited to, aspartic acid (D) and glutamic acid (E). The skilled person can also design other negatively charged amino acids. For instance, a cysteine (C) can be modified with a negatively charged molecule.

If the narrowing contains more than one negatively charged amino acid, such as two, three or four negatively charged amino acids, they are preferably in different monomers, i.e. are not all in the same monomer. For instance, if there are two negatively charged amino acids, each may be in a different monomer. If there are three negatively charged amino acids, they may be in two or three different monomers. If the narrowing contains more than one negatively charged amino acid, such as two, three or four negatively charged amino acids, they may be in the same monomer.

The remaining amino acids in the narrowing are preferably not charged. Amino acids which are not charged are typically uncharged, non-polar and/or aromatic amino acids. The uncharged amino acids, non-polar amino acids and/or aromatic amino acids can be naturally occurring or nonnaturally-occurring. They may be synthetic or modified. Uncharged amino acids have no net charge. Suitable uncharged amino acids include, but are not limited to, cysteine (C), serine (S), threonine (T), methionine (M), asparagines (N) and glutamine (Q). Non-polar amino acids have non-polar side chains. Suitable non-polar amino acids include, but are not limited to, glycine (G), alanine (A), proline (P), isoleucine (I), leucine (L) and valine (V). Aromatic amino acids have an aromatic side chain. Suitable aromatic amino acids include, but are not limited to, histidine (H), phenylalanine (F), tryptophan (W) and tyrosine (Y). Any number and combination of these amino acids may be present in the narrowing in addition to one or more negatively charged amino acids.

If the narrowing comprises one or more positively charged amino acids, there are preferably fewer positively charged amino acids than negatively charged amino acids in the narrowing. The narrowing preferably does not comprise any positively charged amino acids. Positively charged amino acids include, but are not limited to, histidine (H), lysine (K) and arginine (R).

The monomers in the pore are preferably approximately the same length or are the same length. The barrels of the monomers in the pore are preferably approximately the same length or are the same length. Length may be measured in number of amino acids and/or units of length. Barrel deletions are discussed in more detail below. The monomers in the pore preferably have the same number of amino acids deleted from positions 72 to 82 and/or positions 111 to 121 of SEQ ID NO: 2. As discussed above, one or more of the monomers may be attached to a tag or BasTL sequence or fragment thereof which makes it longer than the other monomers in the pore.

In all the embodiments discussed above, one or more, such as 2, 3, 4, 5, 6, 7, 8, 9 or 10, of the mutant monomers may be chemically modified as discussed below.

The pore preferably comprises eight monomers each comprising the sequence shown in SEQ ID NO: 2 or a variant thereof. SEQ ID NO: 2 is the wild-type MspA monomer. The pore preferably comprises two different monomers each comprising the sequence shown in SEQ ID NO: 2 or a variant thereof and wherein the specific stoichiometric ratio of the first different monomer to the second different monomer is 7:1 or 8:1, most preferably 7:1.

A variant of SEQ ID NO: 2 is a polypeptide that has an amino acid sequence which varies from that of SEQ ID NO: 2 and which retains its ability to form a pore. A variant or each variant may comprise only amino acid substitutions compared with SEQ ID NO: 2 or may comprise amino acid deletions. Variants are discussed in more detail below.

The hetero-oligomeric pore may comprise any number of monomers comprising SEQ ID NO: 2, such as 1, 2, 3 or 4 monomers comprising SEQ ID NO: 2. The pore may comprise any number of monomers comprising a variant of SEQ ID NO: 2, such as 1, 2, 3, 4, 5, 6, 7 or 8 monomers comprising a variant of SEQ ID NO: 2. All of the monomers in the pore preferably comprise a variant of SEQ ID NO: 2, i.e. all of the monomers in the pore have been modified in some way compared with the wild type sequence shown in SEQ ID NO: 2. Suitable modifications are discussed below.

The pore may comprise seven first different monomers each comprising a variant of SEQ ID NO: 2 comprising D90N, D91N and D93N and one second different monomer comprising SEQ ID NO: 2.

Amino acids 83 to 111 in SEQ ID NO: 2 contribute to the narrowing of a pore comprising monomers comprising SEQ ID NO: 2. The narrowing in a pore of the invention preferably comprises the amino acids in each monomer which correspond to positions 83 to 111 of SEQ ID NO: 2. Amino acids in a monomer comprising a variant of SEQ ID NO: 2 correspond to positions in SEQ ID NO: 2 with which they align. Any method of alignment may be used, including any of those discussed below. If only amino acids substitutions are made to SEQ ID NO: 2 to produce a variant, the amino acids in the variant which correspond to positions 83 to 111 in SEQ ID NO: 2 will be numbered 83 to 111, i.e. position 90 in the variant corresponds with position 90 in SEQ ID NO: 2. If parts of SEQ ID NO: 2 are deleted to produce the variant or amino acids are added to SEQ ID NO: 2 to form the variant, the amino acids in the variant which correspond to positions 83 to 111 in SEQ ID NO: 2 will not be numbered 83 to 111. By way of illustration, positions 71 to 111 of SEQ ID NO: 2 (i.e. SEQ ID NO: 3) are shown below. The corresponding part of a variant of SEQ ID NO: 2, which only differs from SEQ ID NO: 2 by the deletion of positions 72 and 73 (from the barrel) and the substitutions D91N and D93N (in bold), is shown in SEQ ID NO: 4.

```
                                        (SEQ ID NO: 3)
. . . PWSLGVGINFSYTTPNILIDDGDITAPPFGLNSVITPNLFPGVS

ISADLGN . . .

(SEQ ID NO: 4)
. . . P--LGVGINFSYTTPNILIDNGNITAPPFGLNSVITPNLFPGVS

ISADLGN . . .
```

Positions D90, N91 and N93 in the variant (underlined in SEQ ID NO: 4) correspond to positions D88, D89 and D91 in SEQ ID NO: 2 respectively (because amino acids 72 and 73 in SEQ ID NO: 2 are deleted from the variant). Based on this, a skilled person can determine which amino acids in a variant correspond with positions 83 to 111 in SEQ ID NO: 2.

The narrowing more preferably comprises the amino acids in each monomer which correspond to positions 88, 90, 91, 92, 93, 102, 103 and 105 of SEQ ID NO: 2. If a monomer or each monomer comprises a variant of SEQ ID NO: 2 in which only amino acid substitutions are made, the narrowing preferably comprises the amino acids at positions 88, 90, 91, 92, 93, 102, 103 and 105 in the variant.

The narrowing more preferably comprises the amino acids in each monomer which correspond to positions 90, 91, 93 and 105 of SEQ ID NO: 2. If a monomer or each monomer comprises a variant of SEQ ID NO: 2 in which only amino acids substitutions are made, the narrowing more preferably comprises the amino acids at positions 90, 91, 93 and 105 in the variant.

The second different monomer preferably differs from the first different monomer by comprising a negatively charged amino acid at one or more of the positions which correspond to positions 88, 90, 91, 92, 93, 102, 103 and 105 of SEQ ID NO: 2. A negatively charged amino acid may be present at any number and combination of the positions which correspond to positions 88, 90, 91, 92, 93, 102, 103 and 105 of SEQ ID NO: 2. Preferred combinations are discussed in more detail below. Negatively charge amino acids are discussed above. If each monomer in the pore comprises a variant of SEQ ID NO: 2 in which only amino acids substitutions are made, the second different monomer preferably differs from the first different monomer by comprising a negatively charged amino acid at one or more of the positions 88, 90, 91, 92, 93, 102, 103 and 105.

The second different monomer preferably differs from the first different monomer by comprising a negatively charged amino acid at one or more of the positions which correspond to positions 90, 91, 93 and 105 of SEQ ID NO: 2. A negatively charged amino acid may be present at any number and combination of positions which correspond to positions 90, 91, 93 and 105 of SEQ ID NO: 2, namely (i) 90; (ii) 91; (iii) 93; (iv) 105; (v) 90 and 91; (vi) 90 and 93; (vii) 90 and 105; (viii) 91 and 93; (ix) 91 and 105; (x) 93 and 105; (xi) 90, 91 and 93; (xii) 90, 91 and 105; (xiii) 90, 93 and 105; (xiv) 91, 93 and 105; or (xv) 90, 91, 93 and 105. The second different monomer preferably differs from the first different monomer by comprising a negatively charged amino acid at the position(s) which correspond(s) to position(s) (x) 90; (xi) 91; (xii) 93; (xiii) 90 and 91; (xiv) 90 and 93; (xv) 91 and 93; (xvi) 105; (xvii) 90 and 105; or (xviii) 90, 91 and 105 of SEQ ID NO: 2. Negatively charged amino acids are discussed above. If each monomer in the pore comprises a variant of SEQ ID NO: 2 in which only amino acid substitutions are made, the second different monomer preferably differs from the first different monomer by comprising a negatively charged amino acid at one or more of the positions 90, 91, 93 and 105. The one or more monomers may differ by comprising a negatively charged amino acid at any combination of positions 90, 91, 93 and 105 discussed in (i) to (xv) or (x) to (xviii) above.

Preferably, the second different monomer differs from the first different monomer by comprising one or more negatively charged amino acids, such as 1, 2, 3 or 4 negatively charged amino acids, in its narrowing forming region. For instance, the second different monomer preferably differs from the first different monomer by comprising a negatively charged amino acid at one or more of the positions which correspond to positions 90, 91, 93 and 105 of SEQ ID NO: 2. The second different monomer may comprise a negatively charged amino acid at any number and combination of the positions which correspond to positions 90, 91, 93 and 105 of SEQ ID NO: 2 discussed above in (i) to (xv) or (x) to (xviii).

In any of the embodiments discussed above, the first different monomer preferably comprises an amino acid which is not charged at the position(s) which correspond(s) to position(s) 90 and/or 91 of SEQ ID NO: 2. The first different monomer preferably comprises an amino acid which is not charged at the position(s) which correspond(s) to position(s) 90, 91 and/or 93 of SEQ ID NO: 2. If each monomer in the pore comprises a variant of SEQ ID NO: 2 in which only amino acids substitutions are made, the first different monomer preferably comprises an amino acid which is not charged at position(s) 90 and/or 91 or positions 90, 91 and/or 93. Any of the amino acids which are not charged and which are discussed above may be present. The amino acid is preferably asparagine (N) or glutamine (Q).

A preferred pore of the invention is one in which:

(a) the second different monomer comprises an aspartic acid (D) at the position which corresponds to position 90 of SEQ ID NO: 2 and the first different monomer comprises an asparagine (N) at the position which corresponds to position 90 of SEQ ID NO: 2;

(b) the second different monomer comprises an aspartic acid (D) at the position which corresponds to position 91 of SEQ ID NO: 2 and the first different monomer comprises an asparagine (N) at the position which corresponds to position 91 of SEQ ID NO: 2;

(c) the second different monomer comprises an aspartic acid (D) at the positions which correspond to positions 90 and 91 of SEQ ID NO: 2 and the first different monomer comprises an asparagine (N) at the positions which correspond to positions 90 and 91 of SEQ ID NO: 2;

(d) the second different monomer comprises a glutamic acid (E) at the position which corresponds to position 90 of SEQ ID NO: 2 and the first different monomer comprises an asparagine (N) at the position which corresponds to position 90 of SEQ ID NO: 2;

(e) the second different monomer comprises a glutamic acid (E) at the position which corresponds to position 91 of SEQ ID NO: 2 and the first different monomer comprises an asparagine (N) at the position which corresponds to position 91 of SEQ ID NO: 2;

(f) the second different monomer comprises an glutamic acid (E) at the positions which correspond to positions 90 and 91 of SEQ ID NO: 2 and the first different monomer comprises an asparagine (N) at the positions which correspond to positions 90 and 91 of SEQ ID NO: 2;

(g) the second different monomer comprises an aspartic acid (D) at the position which corresponds to position 90 of SEQ ID NO: 2 and the first different monomer comprises a glutamine (Q) at the position which corresponds to position 90 of SEQ ID NO: 2;

(h) the second different monomer comprises an aspartic acid (D) at the position which corresponds to position 91 of SEQ ID NO: 2 and the first different monomer comprises an glutamine (Q) at the position which corresponds to position 91 of SEQ ID NO: 2;

(i) the second different monomer comprises an aspartic acid (D) at the positions which correspond to positions 90 and 91 of SEQ ID NO: 2 and the first different monomer comprises an glutamine (Q) at the positions which correspond to positions 90 and 91 of SEQ ID NO: 2;

(j) the second different monomer comprises a glutamic acid (E) at the position which corresponds to position 90 of SEQ ID NO: 2 and the first different monomer comprises an glutamine (Q) at the position which corresponds to position 90 of SEQ ID NO: 2;

(k) the second different monomer comprises a glutamic acid (E) at the position which corresponds to position 91 of SEQ ID NO: 2 and the first different monomer comprises an glutamine (Q) at the position which corresponds to position 91 of SEQ ID NO: 2;

(l) the second different monomer comprises an glutamic acid (E) at the positions which correspond to positions 90 and 91 of SEQ ID NO: 2 and the first different monomer comprises an glutamine (Q) at the positions which correspond to positions 90 and 91 of SEQ ID NO: 2;

(m) the second different monomer comprises an aspartic acid (D) at the position which corresponds to position 88 of SEQ ID NO: 2 and the first different monomer comprises an asparagine (N) at the position which corresponds to position 88 of SEQ ID NO: 2;

(n) the second different monomer comprises an aspartic acid (D) at the position which corresponds to position 88 of SEQ ID NO: 2 and the first different monomer comprises a glutamine (Q) at the position which corresponds to position 88 of SEQ ID NO: 2;

(o) the second different monomer comprises an aspartic acid (D) at the position which corresponds to position 103 of SEQ ID NO: 2 and the first different monomer comprises a serine (S) at the position which corresponds to position 103 of SEQ ID NO: 2;

(p) the second different monomer comprises an aspartic acid (D) at the position which corresponds to position 105 of SEQ ID NO: 2 and the first different monomer comprises an isoleucine (I) at the position which corresponds to position 105 of SEQ ID NO: 2;

(q) the second different monomer comprises an aspartic acid (D) at the positions which correspond to positions 88 and 90 of SEQ ID NO: 2 and the first different monomer comprises an asparagine (N) at the positions which correspond to positions 88 and 90 of SEQ ID NO: 2;

(r) the second different monomer comprises an aspartic acid (D) at the positions which correspond to positions 88 and 90 of SEQ ID NO: 2 and the first different monomer comprises a glutamine (Q) at the positions which correspond to positions 88 and 90 of SEQ ID NO: 2; (s) the second different monomer comprises an aspartic acid (D) at the positions which correspond to positions 90 and 103 of SEQ ID NO: 2 and the first different monomer comprises an asparagine (N) and serine (S) at the positions which correspond to positions 90 and 103 of SEQ ID NO: 2 respectively;

(t) the second different monomer comprises an aspartic acid (D) at the positions which correspond to positions 90 and 103 of SEQ ID NO: 2 and the first different monomer comprises a glutamine (Q) and serine (S) at the positions which correspond to positions 90 and 103 of SEQ ID NO: 2 respectively;

(u) the second different monomer comprises an aspartic acid (D) at the positions which correspond to positions 90 and 105 of SEQ ID NO: 2 and the first different monomer comprises an asparagine (N) and isoleucine (I) at the positions which correspond to positions 90 and 105 of SEQ ID NO: 2 respectively;

(v) the second different monomer comprises an aspartic acid (D) at the positions which correspond to positions 90 and 105 of SEQ ID NO: 2 and the first different monomer comprises a glutamine (Q) and isoleucine (I) at the positions which correspond to positions 90 and 105 of SEQ ID NO: 2 respectively;

(w) the second different monomer comprises an aspartic acid (D) at the positions which correspond to positions 90 and 93 of SEQ ID NO: 2 and the first different monomer comprises an asparagine (N) at the positions which correspond to positions 90 and 93 of SEQ ID NO: 2;

(x) the second different monomer comprises an aspartic acid (D) at the positions which correspond to positions 90 and 93 of SEQ ID NO: 2 and the first different monomer comprises a glutamine (Q) at the positions which correspond to positions 90 and 93 of SEQ ID NO: 2;

(y) the second different monomer comprises an aspartic acid (D) at the positions which correspond to positions 91 and 93 of SEQ ID NO: 2 and the first different monomer comprises an asparagine (N) at the positions which correspond to positions 91 and 93 of SEQ ID NO: 2;

(z) the second different monomer comprises an aspartic acid (D) at the positions which correspond to positions 91 and 93 of SEQ ID NO: 2 and the first different monomer comprises a glutamine (Q) at the positions which correspond to positions 91 and 93 of SEQ ID NO: 2;

(aa) the second different monomer comprises an aspartic acid (D) at the position which corresponds to position 93 of SEQ ID NO: 2 and the first different monomer comprises an asparagine (N) at the position which corresponds to position 93 of SEQ ID NO: 2;

(ab) the second different monomer comprises an aspartic acid (D) at the position which corresponds to position 93 of SEQ ID NO: 2 and the first different monomer comprises a glutamine (Q) at the position which corresponds to position 93 of SEQ ID NO: 2;

(ac) the second different monomer comprises an aspartic acid (D) at the position which corresponds to position 90 of SEQ ID NO: 2 and the first different monomer comprises an aspartic acid (D) at the position which corresponds to position 93 of SEQ ID NO: 2;

(ad) the second different monomer comprises an aspartic acid (D) at the positions which correspond to positions 90 and 93 of SEQ ID NO: 2 and the first different monomer comprises an aspartic acid (D) at the position which corresponds to position 93 of SEQ ID NO: 2;

(ae) the second different monomer comprises an aspartic acid (D) at the positions which correspond to positions 91 and 93 of SEQ ID NO: 2 and the first different monomer comprises an aspartic acid (D) at the position which corresponds to position 93 of SEQ ID NO: 2;

(af) the second different monomer comprises an aspartic acid (D) at the position which corresponds to position 90 of SEQ ID NO: 2 and the first different monomer comprises an aspartic acid (D) at the position which corresponds to position 93 of SEQ ID NO: 2;

(ag) the second different monomer comprises an aspartic acid (D) at the positions which correspond to positions 88 and 105 of SEQ ID NO: 2 and the first different monomer comprises an asparagine (N) and isoleucine (I) at the positions which correspond to positions 88 and 105 of SEQ ID NO: 2 respectively; or (ah) the second different monomer comprises an aspartic acid (D) at the positions which correspond to positions 88 and 105 of SEQ ID NO: 2 and the first different monomer comprises a glutamine (Q) and isoleucine (I) at the positions which correspond to positions 88 and 105 of SEQ ID NO: 2 respectively.

In any of (a) to (ah) above, if each monomer in the pore comprises a variant of SEQ ID NO: 2 in which only amino acids substitutions are made, the positions which correspond to positions in SEQ ID NO: 2 have the same number as the positions in SEQ ID NO: 2. For instance, if in (a) each monomer in the pore comprises a variant of SEQ ID NO: 2 in which only amino acids substitutions are made, the second different monomer comprises an aspartic acid (D) at position 90 and the first different monomer comprises an asparagine (N) at position 90.

A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a triblock copolymer membrane such that it diffuses to the membrane and is inserted by binding to the membrane and assembling into a functional state. A variant may be modified in various ways.

A pore of the invention may comprise any number of monomers each comprising a variant of SEQ ID NO: 2, such as 1, 2, 3, 4, 5, 6, 7 or 8 monomers each comprising a variant of SEQ ID NO: 2. In a preferred embodiment, all of the monomers in the pore comprise a variant of SEQ ID NO: 2.

The or each variant of SEQ ID NO: 2 preferably comprises a mutation or substitution at one or more of the positions which correspond to positions G75, G77, L88, D118, Q126, D134 and E139 of SEQ ID NO: 2. If the or each monomer in the pore comprises a variant of SEQ ID NO: 2 in which only amino acids substitutions are made, the or each variant preferably comprises a mutation or substitution at one or more of positions G75, G77, L88, D118, Q126, D134 and E139. The or each variant more preferably comprises one or more of G75S, G77S, L88N, D118R, Q126R, D134R and E139K. The purpose of these mutations is discussed in more detail below.

Rigidity

The or each variant of SEQ ID NO: 2 preferably comprises proline (P) at the position which corresponds to position 108 in SEQ ID NO: 2. If the or each monomer in the pore comprises a variant of SEQ ID NO: 2 in which only amino acids substitutions are made, the or each variant preferably comprises P at position 108.

Barrel Deletions

In the or each variant of SEQ ID NO: 2, (a) 2, 4, 6, 8 or 10 of the amino acids which correspond to positions 72 to 82 of SEQ ID NO: 2 have preferably been deleted and (b) 2, 4, 6, 8 or 10 of the amino acids which correspond to positions 111 to 121 of SEQ ID NO: 2 have preferably been deleted. In other words, 2, 4, 6, 8 or 10 amino acids are preferably deleted from the downward strand (positions 72 to 82) and the upward strand (positions 111 to 121) of the barrel region of SEQ ID NO: 2 when forming the variant. Deletion of amino acids from positions 72 to 82 and 11 to 121 alters the numbering of the subsequent amino acids in the variant as discussed above.

The number of amino acids deleted from positions 72 to 82 may be different from the number of amino acids deleted from positions 111 to 121. The number of amino acids deleted from positions 72 to 82 is preferably the same as the number of amino acids deleted from positions 111 to 121.

Any combination of amino acids from positions 72 to 82 and amino acids from positions 111 to 121 may be deleted. The majority of the amino acids in the downward and upwards strands of the barrel in SEQ ID NO: 2 alternate between hydrophobic and hydrophilic. The hydrophobic amino acids are selected from tryptophan (W), leucine (L), valine (V), isoleucine (I), phenylalanine (F) and tyrosine (Y). The hydrophilic amino acids are selected from serine (S), glycine (G), asparagine (N), proline (P) and aspartic acid (D). The alternation between hydrophobic and hydrophilic amino acids results in the beta-sheet which forms part of the barrel of the pore.

The amino acids from positions 72 to 82 remaining after deletion (i.e. after 2, 4, 6, 8 or 10 amino acids have been deleted from positions 72 to 82) preferably comprise 3, 5, 7 or 9 consecutive amino acids which alternate between hydrophobic and hydrophilic.

The amino acids from positions 111 to 121 remaining after deletion (i.e. after 2, 4, 6, 8 or 10 amino acids have been deleted from positions 111 to 121) preferably comprise 3, 5, 7 or 9 consecutive amino acids which alternate between hydrophobic and hydrophilic.

The amino acids deleted from positions 72 to 82 may correspond to the amino acids deleted from positions 111 to 121 as shown in Table 3 below. For instance, if L74 and G75 are deleted from positions 72 to 82, D118 and L119 may be deleted from positions 111 to 121.

TABLE 3

| Corresponding amino acids in the barrel of SEQ ID NO: 2 | |
| --- | --- |
| Position in (a) | Corresponding position in (b) |
| W72 | N121 |
| S73 | G120 |
| L74 | L119 |
| G75 | D118 |
| V76 | A117 |
| G77 | S116 |
| I78 | I115 |
| N79 | S114 |
| F80 | V113 |
| S81 | G112 |
| Y82 | P111 |

One or more positions of the amino acids that have been deleted from positions 72 to 82 may not correspond to the one or more positions of the amino acids that have been deleted from positions 111 to 121 as shown in Table 3. For instance, if L74 and G75 are deleted from positions 72 to 82, A117 and D118 may be deleted from positions 111 to 121.

The positions of (all of) the amino acids that have been deleted from positions 72 to 82 may not correspond to the positions of (all of) the amino acids that have been deleted from positions 111 to 121 as shown in Table 3. For instance, if L74 and G75 are deleted from positions 72 to 82, 1115 and S116 may be deleted from positions 111 to 121.

The amino acids deleted from positions 72 to 82 are preferably consecutive. The amino acids deleted from positions 111 to 121 are preferably consecutive. The amino acids deleted from positions 72 to 82 and the amino acids deleted from positions 111 to 121 are preferably consecutive.

The or each variant of the sequence shown in SEQ ID NO: 2 is preferably one in which (i) L74, G75, D118 and L119 have been deleted, (ii) G75, V76, A117 and D118 have been deleted, (iii) V76, G77, S116 and A117 have been deleted, (iv) G77, I78, I115 and S116 have been deleted, (v) I78, N79, S114 and I115 have been deleted, (vi) N79, F80, V113 and S114 have been deleted or (vii) F80, S81, G112 and V113 have been deleted. The or each variant of the sequence shown in SEQ ID NO: 2 is preferably one in which L74, G75, V76, G77, S116, A117, D118 and L119 have been deleted. The or each variant of the sequence shown in SEQ ID NO: 2 is preferably one in which L74, G75, N79, F80, V113, S114, D 118 and L119 have been deleted or L74, G75, F80, S81, G112, V113, D118 and L119 have been deleted.

The skilled person can identify other combinations of amino acids that may be deleted in accordance with the invention.

Positions 90 and 91

In SEQ ID NO: 2, amino acids 90 and 91 are both aspartic acid (D). A variant may comprise a negatively charged amino acid, such as aspartic acid (D) or glutamic acid (E), at the position(s) which correspond(s) to position(s) 90 and/or 91 of SEQ ID NO: 2 if the monomer comprising the variant is contributing to the negative charge in the narrowing. If the variant comprises glutamic acid (E) or a nonnatural negatively charged amino acid at the position(s) which correspond(s) to position(s) 90 and/or 91 of SEQ ID NO: 2, it or they may be introduced by substitution. If a monomer comprises a variant of SEQ ID NO: 2 in which only amino acids substitutions are made, the variant may comprise a negatively charged amino acid, such as aspartic acid (D) or glutamic acid (E), at the position(s) 90 and/or 91.

A variant may not comprise a negatively charged amino acid at the position(s) which corresponds to position(s) 90 and/or 91 of SEQ ID NO: 2 if the monomer comprising the variant is not contributing to the negative charge in the narrowing. A variant may comprise any of the amino acids which are not charged and which are discussed above at the position(s) which corresponds to position(s) 90 and/or 91 of SEQ ID NO: 2. If a monomer comprises a variant of SEQ ID NO: 2 in which only amino acids substitutions are made, the variant may not comprise a negatively charged amino acid at the position(s) which corresponds to position(s) 90 and/or 91. The variant preferably may comprise serine (S), glutamine (Q), leucine (L), methionine (M), isoleucine (I), alanine (A), valine (V), glycine (G), phenylalanine (F), tryptophan (W), tyrosine (Y), histidine (H), threonine (T), arginine (R), lysine (K), asparagine (N) or cysteine (C) at the position(s) which corresponds to position(s) 90 and/or 91 of SEQ ID NO: 2 or at position(s) 90 and/or 91. Any combinations of these amino acids at positions 90 and 91 are envisaged by the invention. The variant preferably comprises asparagine (N) or glutamine (Q) at the position(s) which corresponds to position(s) 90 and/or 91 of SEQ ID NO: 2 or at position(s) 90 and/or 91. These amino acids are preferably inserted at position 90 and/or 91 by substitution.

Position 93

In wild-type MspA, amino acid 93 is aspartic acid (D). A variant may comprise a negatively charged amino acid, such as aspartic acid (D) or glutamic acid (E), at the position which corresponds to position 93 of SEQ ID NO: 2 if the monomer comprising the variant is contributing to the negative charge in the narrowing. If the variant comprises glutamic acid (E) or a non-natural negatively charged amino acid at the position which corresponds to position 93 of SEQ ID NO: 2, it may be introduced by substitution. If a monomer in the pore comprises a variant of SEQ ID NO: 2 in which only amino acid substitutions are made, the variant may comprise a negatively charged amino acid, such as aspartic acid (D) or glutamic acid (E), at the position 93.

A variant may not comprise a negatively charged amino acid at the position which corresponds to position 93 of SEQ ID NO: 2 if the monomer comprising the variant is not contributing to the negative charge in the narrowing. If a monomer in the pore comprises a variant of SEQ ID NO: 2 in which only amino acids substitutions are made, the variant may not comprise a negatively charged amino acid, such as aspartic acid (D) or glutamic acid (E), at the position 93. A variant may comprise any of the amino acids which are not charged and which are discussed above at the position which corresponds to position 93 of SEQ ID NO: 2 or at position 93. The variant preferably may comprise serine (S), glutamine (Q), leucine (L), methionine (M), isoleucine (I), alanine (A), valine (V), glycine (G), phenylalanine (F), tryptophan (W), tyrosine (Y), histidine (H), threonine (T), arginine (R), lysine (K), asparagine (N) or cysteine (C) at the position which corresponds to position 93 of SEQ ID NO: 2 or at position 93. The variant preferably comprises asparagine (N) at the position which corresponds to position 93 of SEQ ID NO: 2 or at position 93. These amino acids are preferably inserted at position 93 by substitution.

Cap Forming Region

In SEQ ID NO: 2, amino acids 1 to 72 and 122 to 184 form the cap of the pore. Of these amino acids, V9, Q12, D13, R14, T15, W40, I49, P53, G54, D56, E57, E59, T61, E63, Y66, Q67, I68, F70, P123, I125, Q126, E127, V128, A129, T130, F131, S132, V133, D134, S136, G137, E139, V144, H148, T150, V151, T152, F163, R165, I167, S169, T170 and S173 face inwards into the channel of the pore.

Barrel Forming Region

In SEQ ID NO: 2, amino acids 72 to 82 and 112 to 121 form the barrel of the pore. Of these amino acids, S73, G75, G77, N79, S81, G112, S114, S116, D118 and G120 face inwards into the channel of the pore. S73, G75, G77, N79, S81 face inwards in the downwards strand and G112, S114, S116, D118 and G120 face inwards in the upwards strand.

Decreased Net Negative Charge

The or each variant preferably comprises one or more modifications which decrease the net negative charge of the inward facing amino acids in the cap forming region and/or the barrel forming region of the monomer. The variant preferably comprises two or more modifications which decrease the net negative charge of the inward facing amino acids in the cap forming region and/or the barrel forming region of the monomer. Any such modifications to the barrel forming region are in addition to the deletions of the invention discussed above.

The variant may comprise any number of modifications, such as 1 or more, 2 or more, 3 or more, 4 or more, 5 or more, 6 or more, 7 or more, 8 or more, 9 or more, 10 or more, 15 or more, 20 or more, 30 or more, or 40 or more modifications.

The net negative charge may be decreased by any means known in the art. The net negative charge is decreased in a manner that does not interfere with the ability of the mutant monomer to form a pore. This can be measured as discussed above.

The net negative charge of the inward facing amino acids in the cap forming region and/or the barrel forming region may be decreased. This means that the inward facing amino acids in the cap forming region and/or the barrel forming region comprise fewer negatively charged amino acids than in SEQ ID NO: 2 and/or comprises more positively charged amino acids than in SEQ ID NO: 2. The one or more modifications may lead to a net positive charge in the inward facing amino acids in the cap forming region and/or the barrel forming region The net charge can be measured using methods known in the art. For instance, the net charge of the inward facing amino acids in the cap forming region and/or the barrel forming region may be calculated using routine methods.

The one or more modifications are preferably one or more deletions of negatively charged amino acids. Removal of one or more negatively charged amino acids reduces the net negative charge of the inward facing amino acids in the cap forming region and/or barrel forming region. A negatively charged amino acid is an amino acid with a net negative charge. Negatively charged amino acids include, but are not limited to, aspartic acid (D) and glutamic acid (E). Methods for deleting amino acids from proteins, such as MspA monomers, are well known in the art.

The one or more modifications are preferably one or more substitutions of negatively charged amino acids with one or more positively charged, uncharged, non-polar and/or aromatic amino acids. A positively charged amino acid is an amino acid with a net positive charge. The positively charged amino acid(s) can be naturally-occurring or non-naturally-occurring. The positively charged amino acid(s) may be synthetic or modified. For instance, modified amino acids with a net positive charge may be specifically designed for use in the invention. A number of different types of modification to amino acids are well known in the art.

Preferred naturally-occurring positively charged amino acids include, but are not limited to, histidine (H), lysine (K) and arginine (R). Any number and combination of H, K and/or R may be substituted for the inward facing amino acids in the cap forming region and/or barrel forming region.

The uncharged amino acids, non-polar amino acids and/or aromatic amino acids can be naturally occurring or non-naturally-occurring. They may be synthetic or modified. Uncharged amino acids have no net charge. Suitable uncharged amino acids include, but are not limited to, cysteine (C), serine (S), threonine (T), methionine (M), asparagines (N) and glutamine (Q). Non-polar amino acids have non-polar side chains. Suitable non-polar amino acids include, but are not limited to, glycine (G), alanine (A), proline (P), isoleucine (I), leucine (L) and valine (V). Aromatic amino acids have an aromatic side chain. Suitable aromatic amino acids include, but are not limited to, histidine (H), phenylalanine (F), tryptophan (W) and tyrosine (Y). Any number and combination of these amino acids may be substituted into the inward facing amino acids in the cap forming region and/or the barrel forming region.

The one or more negatively charged amino acids are preferably substituted with alanine (A), valine (V), asparagine (N), glutamine (Q) or glycine (G). Preferred substitutions include, but are not limited to, substitution of D with A, substitution of D with V, substitution of D with N, substitution of D with Q and substitution of D with G.

The one or more modifications are preferably one or more introductions of positively charged amino acids. The introduction of positive charge decreases the net negative charge. The one or more positively charged amino acids may be introduced by addition or substitution. Any amino acid may be substituted with a positively charged amino acid. One or more uncharged amino acids, non-polar amino acids and/or aromatic amino acids may be substituted with one or more positively charged amino acids. Any number of positively charged amino acids may be introduced.

Wild-type MspA comprises a polar glutamine (Q) at position 126. The one or more modifications preferably reduce the net negative charge at the position in a variant which corresponds to position 126 in SEQ ID NO: 2. If the monomer comprises a variant of SEQ ID NO: 2 in which only amino acids substitutions are made, one or more modifications preferably reduce the net negative charge at the position in a variant which corresponds to position 126. The one or more modifications preferably increase the net positive charge at the position which corresponds to position 126 or at position 126. This can be achieved by replacing the polar amino acid at position 126 or an adjacent or a nearby inward facing amino acid with a positively charged amino acid. The or each variant preferably comprises a positively charged amino acid at the position which corresponds to position 126 or at position 126. The or each variant preferably comprises a positively charged amino acid at one or more of the positions which correspond to positions 123, 125, 127 and 128 in SEQ ID NO: 2 or at one or more of positions 123, 125, 127 and 128. The or each variant may comprise any number and combination of positively charged amino acids at the positions which correspond to positions 123, 125, 127 and 128 or at one or more of positions 123, 125, 127 and 128. The positively charged amino acid(s) may be introduced by addition or substitution.

The one or more modifications are preferably one or more introductions of positively charged amino acids which neutralise one or more negatively charged amino acids. The neutralisation of negative charge decreases the net negative charge. The one or more positively charged amino acids may be introduced by addition or substitution. Any amino acid may be substituted with a positively charged amino acid. One or more uncharged amino acids, non-polar amino acids and/or aromatic amino acids may be substituted with one or more positively charged amino acids. Any number of positively charged amino acids may be introduced. The number is typically the same as the number of negatively charged amino acids being neutralised.

The one or more positively charged amino acids may be introduced at any position in the cap forming region and/or the barrel forming region as long as they neutralise the negative charge of the one or more inward facing negatively charged amino acids. To effectively neutralise the negative charge in the cap forming region, there is typically 5 or fewer amino acids in the variant between each positively charged amino acid that is introduced and the negatively charged amino acid it is neutralising. There are preferably 4 or fewer, 3 or fewer or 2 or fewer amino acids in the cap forming region of the variant between each positively charged amino acid that is introduced and the negatively charged amino acid it is neutralising. There is more preferably two amino acids in the cap forming region of the variant between each positively charged amino acid that is introduced and the negatively charged amino acid it is neutralising. Each positively charged amino acid is most preferably introduced adjacent in the cap forming region of the variant to the negatively charged amino acid it is neutralising.

To effectively neutralise the negative charge in the barrel forming region, there is typically 5 or fewer inward facing amino acids between each positively charged amino acid that is introduced and the negatively charged amino acid it is neutralising. There is preferably 4 or fewer, 3 or fewer or 2 or fewer inward facing amino acids in the barrel forming region of the variant between each positively charged amino acid that is introduced and the negatively charged amino acid it is neutralising. There is more preferably one inward facing amino acid in the barrel forming region of the variant between each positively charged amino acid that is introduced and the negatively charged amino acid it is neutralising. Each positively charged amino acid is most preferably introduced at the inward facing position adjacent in the barrel forming region of the variant to the negatively charged amino acid it is neutralising.

SEQ ID NO: 2 comprises aspartic acid (D) at positions 118 and 134 and glutamic acid (E) at position 139. Amino acid 118 in each monomer is present within the barrel of the pore. The or each variant preferably comprises a positively charged amino acid at one or more of the positions which correspond to positions 114, 116, 120, 123, 70, 73, 75, 77 and 79 of SEQ ID NO: 2. If the or each monomer in the pore comprises a variant of SEQ ID NO: 2 in which only amino acids substitutions are made, the variant preferably comprises a positively charged amino acid at one or more of positions 114, 116, 120, 123, 70, 73, 75, 77 and 79. Positive charges at one or more of these positions neutralise the negative charge at position 118. Positively charged amino acids may be present at any number and combination of the positions which correspond to positions 114, 116, 120, 123, 70, 73, 75, 77 and 79 or at positions 114, 116, 120, 123, 70, 73, 75, 77 and 79. The amino acids may be introduced by addition or substitution.

Amino acids 134 and 139 in each monomer are part of the cap. The or each variant preferably comprises a positively charged amino acid at one or more of positions which correspond to positions 129, 132, 136, 137, 59, 61 and 63 in SEQ ID NO: 2. If the or each monomer in the pore comprises a variant of SEQ ID NO: 2 in which only amino acids substitutions are made, the or each variant preferably comprises a positively charged amino acid at one or more of positions 129, 132, 136, 137, 59, 61 and 63. Positive charges at one or more of these positions neutralise the negative charge at position 134. Positively charged amino acids may be present at any number and combination of the positions which correspond to positions 129, 132, 136, 137, 59, 61 and 63 in SEQ ID NO: 2 or at positions 129, 132, 136, 137, 59, 61 and 63. The amino acids may be introduced by addition or substitution.

The variant preferably comprises a positively charged amino acid at one or more of positions which correspond to positions 137, 138, 141, 143, 45, 47, 49 and 51 of SEQ ID NO: 2 or at positions 137, 138, 141, 143, 45, 47, 49 and 51. Positive charges at one or more of these positions neutralise the negative charge at position 139. Positively charged amino acids may be present at any number and combination of the positions which correspond to positions 137, 138, 141, 143, 45, 47, 49 and 51 of SEQ ID NO: 2 or at positions 137, 138, 141, 143, 45, 47, 49 and 51. The amino acids may be introduced by addition or substitution.

Positions 118, 126, 134 and 139

The one or more modifications preferably reduce the net negative charge at one or more of the positions which correspond to positions 118, 126, 134 and 139 in SEQ ID NO: 2 or at positions 118, 126, 134 and 139. The one or more modifications preferably reduce the net negative charge at the position(s) which corresponds to position(s) or at position(s) 118; 126; 134; 139; 118 and 126; 118 and 134; 118 and 139; 126 and 134; 126 and 139; 134 and 139; 118, 126 and 134; 118, 126 and 139; 118, 134 and 139; 126, 134 and 139; or 118, 126, 134 and 139 in SEQ ID NO: 2.

The variant preferably does not comprise aspartic acid (D) or glutamic acid (E) at one or more of the positions which correspond to positions 118, 126, 134 and 139 of SEQ ID NO: 2 or at positions 118, 126, 134 and 139. The variant preferably does not comprise aspartic acid (D) or glutamic acid (E) at any of the combination of positions which correspond to positions 118, 126, 134 and 139 or at positions 118, 126, 134 and 139 disclosed above. The variant more preferably comprises arginine (R), glycine (G) or asparagine (N) at one or more of the positions which correspond to positions 118, 126, 134 and 139 of SEQ ID NO: 2 or at positions 118, 126, 134 and 139, such as any of the combinations of positions 118, 126, 134 and 139 disclosed above. The variant most preferably comprises D118R, Q126R, D134R and E139K.

Methods for introducing or substituting naturally-occurring amino acids are well known in the art. For instance, methionine (M) may be substituted with arginine (R) by replacing the codon for methionine (ATG) with a codon for arginine (CGT) at the relevant position in a polynucleotide encoding the mutant monomer. The polynucleotide can then be expressed as discussed above.

The one or more modifications are preferably one or more chemical modifications of one or more negatively charged amino acids which neutralise their negative charge. For instance, the one or more negatively charged amino acids may be reacted with a carbodiimide.

Other Modifications

The variant preferably comprises one or more of:
(e) serine (S) at the position which corresponds to position 75 of SEQ ID NO: 2 or at position 75;
(f) serine (S) at the position which corresponds to position 77 of SEQ ID NO: 2 or at position 77; and
(g) asparagine (N) or lysine (K) at the position which corresponds to position 88 in SEQ ID NO: 2 or at position 88.

The variant may comprise any number and combination of (e) to (g), including (e), (f), (g), (e) and (f), (f) and (g), (e) and (g) and (e), (f) and (g). The variant preferably comprises G75S, G77S and L88N.

The variant most preferably comprises (a) D90N, D91N, D93N, D118R, D134R and E139K, (b) L88N, D90N, D91N, D93N, D118R, D134R and E139K, (c) G75S, G77S, L88N, D90N, D91N, D93N, D118R, Q126R, D134R and E139K or (d) G75S, G77S, L88N, D90N, D91N, D118R, Q126R, D134R and E139K. Where the positions in (a) to (d) correspond to those in SEQ ID NO: 2 or are the positions in the variant.

The variant preferably further comprises one or more of:
(i) phenylalanine (F) at the position which corresponds to position 89 of SEQ ID NO: 2 or at position 89;
(j) glutamic acid (E) at the position which corresponds to position 95 of SEQ ID NO: 2 or at position 95 and lysine (K) at the position which corresponds to position 98 of SEQ ID NO: 2 or at position 98;
(l) aspartic acid (D) at the position which corresponds to position 96 of SEQ ID NO: 2 or at position 96;
(m) glycine (G) at the position which corresponds to position 102 of SEQ ID NO: 2 or at position 102;
(n) alanine (A) at the position which corresponds to position 103 of SEQ ID NO: 2 or at position 103; and
(o) alanine (A), serine (S) or proline (P) at the position which corresponds to position 108 or at position 108.

The variant may comprise any number and combination of (i) to (o).

Improved Movement

The or each variant preferably comprises one or more modifications in a part of the variant which interacts with a polynucleotide binding protein. This improves the movement of a target polynucleotide with respect to a pore comprising the variant when the movement is controlled by a polynucleotide binding protein. These modifications and their advantages are discussed in International Application No. PCT/GB2015/051291 (published as WO 2015/166276). The one or more modifications preferably provide more consistent movement of the target polynucleotide with respect to, such as through, a transmembrane pore comprising the variant. The one or more modifications preferably reduce the noise associated with the movement of the target polynucleotide with respect to, such as through, a transmembrane pore comprising the variant. If the target polynucleotide is double stranded, the one or more modifications preferably reduce the noise associated with movement of the complement strand relative to the template strand and/or provide more consistent movement of the complement strand relative to the template strand. This is advantageous for strand sequencing of double stranded target polynucleotides. The two stands of the double stranded polynucleotide are preferably linked by a bridging moiety, such as a hairpin loop or hairpin loop adaptor. This is discussed in more detail below.

Any number of modifications can be made, such as 2 or more, 3 or more, 5 or more, 10 or more, 15 or more, 20 or more, 25 or more, 30 or more, 50 or more or 100 or more modifications.

The part of the variant which interacts with the polynucleotide binding protein typically comprises the amino acids which correspond to positions 12, 14, 48, 52, 53, 54, 55, 56, 57, 58, 59, 60, 134, 135, 136, 137, 138, 139, 169 and 170 of SEQ ID NO: 2 or at positions 12, 14, 48, 52, 53, 54, 55, 56, 57, 58, 59, 60, 134, 135, 136, 137, 138, 139, 169 and 170.

The part of the variant which interacts with the polynucleotide binding protein preferably comprises the amino acids
(a) which correspond to positions 12, 14, 52, 54, 56, 57, 59, 134, 136, 138, 139 and 169 in SEQ ID NO: 2 or at positions 12, 14, 52, 54, 56, 57, 59, 134, 136, 138, 139 and 169;

(b) 12, 14, 56, 57, 59, 134, 136, 139 and 169 in SEQ ID NO: 2 or at positions 12, 14, 56, 57, 59, 134, 136, 139 and 169;

(c) 56, 57, 59, 134, 136, 139 and 169 in SEQ ID NO: 2 or at positions 56, 57, 59, 134, 136, 139 and 169; or (d) 56, 57, 59, 134 and 139 in SEQ ID NO: 2 or at positions 56, 57, 59, 134 and 139.

Any modifications may be made in accordance with the invention. The variant may comprise one or more modifications which (a) alter the charge, (b) alter the sterics, (c) alter the hydrogen bonding, (d) alter the π stacking or (e) alter the structure of the part of the variant which interacts with the polynucleotide binding protein. Any number and combination of these may be altered. For instance, the method may involve making one of more modifications which {a}; {b}; {c}; {d}; {e}; {a,b}; {a,c}; {a,d}; {a,e}; {b,c}; {b,d}; {b,e}; {c,d}; {c,e}; {d,e}; {a,b,c}; {a,b,d}; {a,b,e}; {a,c,d}; {a,c,e}; {a,d,e}; {b,c,d}; {b,c,e}; {b,d,e}; {c,d,e}; {a,b,c,d}; {a,b,c,e}; {a,b,d,e}; {a,c,d,e}; {b,c,d,e}; or {a,b,c,d,e}.

When modifying the variant, the one or more modifications typically involve introducing or replacing one or more amino acids. The invention typically involves making one or more amino acid substitutions.

Modifications which alter the charge may involve increasing the net negative charge or decreasing the net negative charge. The method preferably comprises making one or more modifications which decrease the net negative charge of the part of the variant which interacts with the polynucleotide binding protein. Modifications which decrease net negative charge are discussed in more detail above. In a preferred embodiment, the variant does not comprise aspartic acid (D) or glutamic acid (E) at one or more of the positions which correspond to positions 56, 57, 59, 134 and 139 of SEQ ID NO: 2 or at positions 56, 57, 59, 134 and 139. The variant preferably comprises one or more of (a) D56N or D56R, (b) E57N or E57R, (c) E59N or E59R, (d) D134N or D134R and (e) E139N, E139R or E139K. The variant may comprise any number and combination of these modifications. For instance, one or more of the monomers may comprise {a}; {b}; {c}; {d}; {e}; {a,b}; {a,c}; {a,d}; {a,e}; {b,c}; {b,d}; {b,e}; {c,d}; {c,e}; {d,e}; {a,b,c}; {a,b,d}; {a,b,e}; {a,c,d}; {a,c,e}; {a,d,e}; {b,c,d}; {b,c,e}; {b,d,e}; {c,d,e}; {a,b,c,d}; {a,b,c,e}; {a,b,d,e}; {a,c,d,e}; {b,c,d,e}; or {a,b,c,d,e}.

Modifications which alter the sterics may involve increasing or decreasing the size of amino acid residues, for instance by substitution. For instance, sterics can be increased by the introduction of one or more bulky amino acids, such as phenylalanine (F), tryptophan (W), tyrosine (Y) and histidine (H).

Modifications which alter the hydrogen bonding may involve the introduction or replacement of one or more amino acids which can hydrogen bond.

Modifications which alter the π stacking may involve the introduction or replacement of amino acids that interact through delocalised electron π systems. For instance, π stacking can be increased by the introduction of one or more aromatic amino acids, such as phenylalanine (F), tryptophan (W), tyrosine (Y) and histidine (H).

Variants

In addition to the specific mutations discussed above, the variant may include other mutations. Over the entire length of the amino acid sequence of SEQ ID NO: 2, a variant will preferably be at least 50% homologous to that sequence based on amino acid similarity or identity. More preferably, the variant may be at least 55%, at least 60%, at least 65%, at least 70%, at least 75%, at least 80%, at least 85%, at least 90% and more preferably at least 95%, 97% or 99% homologous based on amino acid similarity or identity to the amino acid sequence of SEQ ID NO: 2 over the entire sequence. There may be at least 80%, for example at least 85%, 90% or 95%, amino acid similarity or identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/).

Similarity can be measured using pairwise identity or by applying a scoring matrix such as BLOSUM62 and converting to an equivalent identity. Since they represent functional rather than evolved changes, deliberately mutated positions would be masked when determining homology. Similarity may be determined more sensitively by the application of position-specific scoring matrices using, for example, PSIBLAST on a comprehensive database of protein sequences. A different scoring matrix could be used that reflect amino acid chemico-physical properties rather than frequency of substitution over evolutionary time scales (e.g. charge).

SEQ ID NO: 2 is the mature form of the wild-type MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 4 below. Where amino acids have similar polarity, this can also be determined by reference to the hydropathy scale for amino acid side chains in Table 5.

TABLE 4

| Chemical properties of amino acids | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 5

| Hydropathy scale | |
|---|---|
| Side Chain | Hydropathy |
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues which correspond to positions 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers may be modified to assist their identification or purification, for example by the addition of a streptavidin tag or by the addition of a signal sequence to promote their secretion from a cell where the monomer does not naturally contain such a sequence. Other suitable tags are discussed in more detail below. The monomers may be labelled with a revealing label. The revealing label may be any suitable label which allows the monomers to be detected. Suitable labels are described below.

The monomers may also be produced using D-amino acids. For instance, the monomers may comprise a mixture of L-amino acids and D-amino acids. This is conventional in the art for producing such proteins or peptides.

The monomers typically contain one or more specific modifications to facilitate nucleotide discrimination. The monomers may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with NaBH$_4$, amidination with methylacetimidate or acylation with acetic anhydride.

The monomers can be produced using standard methods known in the art. The monomer may be made synthetically or by recombinant means. For example, the monomers may be synthesized by in vitro translation and transcription (IVTT). Suitable methods for producing pores and monomers are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are known in the art.

Chemical Modification

In some embodiments, a monomer is chemically modified. The monomer is typically chemically modified once it has formed a hetero-oligomeric pore in accordance with the invention. The monomer can be chemically modified in any way and at any site. The monomer is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The monomer may be chemically modified by the attachment of any molecule. For instance, the monomer may be chemically modified by attachment of a dye or a fluorophore.

In other embodiment, the monomer may be attached to a polynucleotide binding protein. This forms a modular sequencing system that may be used in the methods of sequencing of the invention. Polynucleotide binding proteins are discussed below.

The polynucleotide binding protein is preferably covalently attached to the monomer. The protein can be covalently attached to the monomer using any method known in the art. The monomer and protein may be chemically fused or genetically fused. The monomer and protein are genetically fused if the whole construct is expressed from a single polynucleotide sequence. Genetic fusion of a monomer to a polynucleotide binding protein is discussed in International Application No. PCT/GB09/001679 (published as WO 2010/004265).

If the polynucleotide binding protein is attached via cysteine linkage, the one or more cysteines have preferably been introduced to the monomer by substitution. The monomer may comprise cysteine residues at one or more of the positions which correspond to positions 10 to 15, 51 to 60, 136 to 139 and 168 to 172 of SEQ ID NO: 2 or at positions 10 to 15, 51 to 60, 136 to 139 and 168 to 172. These positions are present in loop regions which have low conservation amongst homologues indicating that mutations or insertions may be tolerated. They are therefore suitable for attaching a polynucleotide binding protein. The reactivity of cysteine residues may be enhanced by modification as described above.

The polynucleotide binding protein may be attached directly to the monomer or via one or more linkers. The molecule may be attached to the monomer using the hybridization linkers described in International Application No. PCT/GB10/000132 (published as WO 2010/086602). Alternatively, peptide linkers may be used. Peptide linkers are amino acid sequences. The length, flexibility and hydrophilicity of the peptide linker are typically designed such that it does not to disturb the functions of the monomer and molecule. Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$ and $(SG)_8$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline.

The monomer may be chemically modified with a molecular adaptor and a polynucleotide binding protein.

The reactivity of cysteine residues may be enhanced by modification of the adjacent residues. For instance, the basic groups of flanking arginine, histidine or lysine residues will change the pKa of the cysteines thiol group to that of the more reactive $S^-$ group. The reactivity of cysteine residues may be protected by thiol protective groups such as dTNB. These may be reacted with one or more cysteine residues of the monomer before a linker is attached.

The molecule (with which the monomer is chemically modified) may be attached directly to the monomer or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

Any of the proteins described herein, such as the monomers and pores of the invention, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the protein. An example of this would be to react a gel-shift reagent to a cysteine engineered on the outside of the protein. This has been demonstrated as a method for separating hemolysin hetero-oligomers (Chem Biol. 1997 July; 4(7):497-505).

Any of the proteins described herein, such as the monomers and pores of the invention, may be labelled with a revealing label. The revealing label may be any suitable label which allows the protein to be detected. Suitable labels include, but are not limited to, fluorescent molecules, radio-isotopes, e.g. $^{125}$I, $^{35}$S, enzymes, antibodies, antigens, polynucleotides and ligands such as biotin.

Any of the proteins described herein, such as the monomers or pores of the invention, may be made synthetically or by recombinant means. For example, the protein may be synthesized by in vitro translation and transcription (IVTT). The amino acid sequence of the protein may be modified to include non-naturally occurring amino acids or to increase the stability of the protein. When a protein is produced by synthetic means, such amino acids may be introduced during production. The protein may also be altered following either synthetic or recombinant production.

Proteins may also be produced using D-amino acids. For instance, the protein may comprise a mixture of L-amino acids and D-amino acids. This is conventional in the art for producing such proteins or peptides.

The protein may also contain other non-specific modifications as long as they do not interfere with the function of the protein. A number of non-specific side chain modifications are known in the art and may be made to the side chains of the protein(s). Such modifications include, for example, reductive alkylation of amino acids by reaction with an aldehyde followed by reduction with $NaBH_4$, amidination with methylacetimidate or acylation with acetic anhydride.

Any of the proteins described herein, including the monomers and pores of the invention, can be produced using the method of the invention or standard methods known in the art. Polynucleotide sequences encoding a protein may be derived and replicated using standard methods in the art. Polynucleotide sequences encoding a protein may be expressed in a bacterial host cell using standard techniques in the art. The protein may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

Proteins may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Constructs

The hetero-oligomeric pore of the invention may comprise a first different construct comprising two or more covalently attached monomers and a second different construct comprising two or more covalently attached monomers. Any of the construct embodiments discussed above apply to the pore of the invention.

Polynucleotide Characterisation

The invention provides a method of characterising a target polynucleotide. The method involves measuring one or more characteristics of the target polynucleotide. The target polynucleotide may also be called the template polynucleotide or the polynucleotide of interest.

Polynucleotide

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag. Suitable labels are described below. The polynucleotide may comprise one or more spacers.

A nucleotide typically contains a nucleobase, a sugar and at least one phosphate group. The nucleobase and sugar form a nucleoside.

The nucleobase is typically heterocyclic. Nucleobases include, but are not limited to, purines and pyrimidines and more specifically adenine (A), guanine (G), thymine (T), uracil (U) and cytosine (C).

The sugar is typically a pentose sugar. Nucleotide sugars include, but are not limited to, ribose and deoxyribose. The sugar is preferably a deoxyribose.

The polynucleotide preferably comprises the following nucleosides: deoxyadenosine (dA), deoxyuridine (dU) and/or thymidine (dT), deoxyguanosine (dG) and deoxycytidine (dC).

The nucleotide is typically a ribonucleotide or deoxyribonucleotide. The nucleotide typically contains a monophosphate, diphosphate or triphosphate. The nucleotide may comprise more than three phosphates, such as 4 or 5 phosphates. Phosphates may be attached on the 5' or 3' side of a nucleotide. Nucleotides include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP), deoxycytidine monophosphate (dCMP) and deoxymethylcytidine monophosphate. The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA). The polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety.

The polynucleotide is most preferably ribonucleic nucleic acid (RNA) or deoxyribonucleic acid (DNA).

The polynucleotide can be any length. For example, the polynucleotide can be at least 10, at least 50, at least 100, at least 150, at least 200, at least 250, at least 300, at least 400 or at least 500 nucleotides or nucleotide pairs in length. The polynucleotide can be 1000 or more nucleotides or nucleotide pairs, 5000 or more nucleotides or nucleotide pairs in length or 100000 or more nucleotides or nucleotide pairs in length.

Any number of polynucleotides can be investigated. For instance, the method of the invention may concern characterising 2, 3, 4, 5, 6, 7, 8, 9, 10, 20, 30, 50, 100 or more polynucleotides. If two or more polynucleotides are characterized, they may be different polynucleotides or two instances of the same polynucleotide.

The polynucleotide can be naturally occurring or artificial. For instance, the method may be used to verify the sequence of a manufactured oligonucleotide. The method is typically carried out in vitro.

Sample

Each analyte is typically present in any suitable sample. The invention is typically carried out on two or more samples that are known to contain or suspected to contain the analytes. Alternatively, the invention may be carried out on two or more samples to confirm the identity of two or more analytes whose presence in the samples is known or expected.

The sample may be a biological sample. The invention may be carried out in vitro using at least one sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep, fish, chickens or pigs or may alternatively be pets such as cats or dogs. Alternatively, the first sample and/or second sample may be of plant origin, such as a sample obtained from a commercial crop, such as a cereal, legume, fruit or vegetable, for example wheat, barley, oats, canola, maize, soya, rice, rhubarb, bananas, apples, tomatoes, potatoes, grapes, tobacco, beans, lentils, sugar cane, cocoa, cotton.

The sample may be a non-biological sample. The non-biological sample is preferably a fluid sample. Examples of non-biological samples include surgical fluids, water such as drinking water, sea water or river water, and reagents for laboratory tests.

The sample is typically processed prior to being used in the invention, for example by centrifugation or by passage through a membrane that filters out unwanted molecules or cells, such as red blood cells. The sample may be measured immediately upon being taken. The sample may also be typically stored prior to assay, preferably below −70° C.

Characterisation

The method may involve measuring two, three, four or five or more characteristics of the polynucleotide. The one or more characteristics are preferably selected from (i) the length of the polynucleotide, (ii) the identity of the poly- nucleotide, (iii) the sequence of the polynucleotide, (iv) the secondary structure of the polynucleotide and (v) whether or not the polynucleotide is modified. Any combination of (i) to (v) may be measured in accordance with the invention, such as {i}, {ii}, {iii}, {iv}, {v}, {i,ii}, {i,iii}, {i,iv}, {i,v}, {ii,iii}, {ii,iv}, {ii,v}, {iii,iv}, {iii,v}, {iv,v}, {i,ii,iii}, {i,ii, iv}, {i,ii,v}, {i,iii,iv}, {i,iii,v}, {i,iv,v}, {ii,iii,iv}, {ii,iii,v}, {ii,iv,v}, {iii,iv,v}, {i,ii,iii,iv}, {i,ii,iii,v}, {i,ii,iv,v}, {i,iii, iv,v}, {ii,iii,iv,v} or {i,ii,iii,iv,v}. Different combinations of (i) to (v) may be measured for the first polynucleotide compared with the second polynucleotide, including any of those combinations listed above.

For (i), the length of the polynucleotide may be measured for example by determining the number of interactions between the polynucleotide and the pore or the duration of interaction between the polynucleotide and the pore.

For (ii), the identity of the polynucleotide may be mea- sured in a number of ways. The identity of the polynucle- otide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single- stranded and double-stranded polynucleotide to be distin- guished.

For (v), the presence or absence of any modification may be measured. The method preferably comprises determining whether or not the polynucleotide is modified by methyl- ation, by oxidation, by damage, with one or more proteins or with one or more labels, tags or spacers. Specific modifica- tions will result in specific interactions with the pore which can be measured using the methods described below. For instance, methylcytosine may be distinguished from cyto- sine on the basis of the current flowing through the pore during its interaction with each nucleotide.

The target polynucleotide is contacted with a hetero- oligomeric pore of the invention. The pore is typically present in a membrane. Suitable membranes are discussed below. The method may be carried out using any apparatus that is suitable for investigating a membrane/pore system in which a pore is present in a membrane. The method may be carried out using any apparatus that is suitable for trans- membrane pore sensing. For example, the apparatus com- prises a chamber comprising an aqueous solution and a barrier that separates the chamber into two sections. The barrier typically has an aperture in which the membrane containing the pore is formed. Alternatively the barrier forms the membrane in which the pore is present.

The method may be carried out using the apparatus described in International Application No. PCT/GB08/ 000562 (WO 2008/102120).

A variety of different types of measurements may be made. This includes without limitation: electrical measure- ments and optical measurements. Possible electrical mea- surements include: current measurements, impedance mea- surements, tunnelling measurements (Ivanov AP et al., Nano Lett. 2011 Jan. 12; 11(1):279-85), and FET measurements (International Application WO 2005/124888). Optical mea- surements may be combined with electrical measurements (Soni G V et al., Rev Sci Instrum. 2010 January; 81(1): 014301). The measurement may be a transmembrane current measurement such as measurement of ionic current flowing through the pore.

Electrical measurements may be made using standard single channel recording equipment as described in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Applica- tion WO 2009/077734 and International Application WO 2011/067559.

The method is preferably carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129(27):8650-5. In some instances, the current passing through the pore as a polynucleotide moves with respect to the pore is used to estimate or determine the sequence of the polynucleotide. This is strand sequencing.

The method may involve measuring the current passing through the pore as the polynucleotide moves with respect to the pore. Therefore the apparatus used in the method may also comprise an electrical circuit capable of applying a potential and measuring an electrical signal across the membrane and pore. The methods may be carried out using a patch clamp or a voltage clamp. The methods preferably involve the use of a voltage clamp.

The method of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The method is typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The method is typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The method may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Polynucleotide Binding Protein

Step (a) preferably comprises contacting the polynucleotide with a polynucleotide binding protein such that the protein controls the movement of the polynucleotide through the pore.

More preferably, the method comprises (a) contacting the polynucleotide with the pore of the invention and a polynucleotide binding protein such that the protein controls the movement of the polynucleotide through the pore and (b) taking one or more measurements as the polynucleotide moves with respect to the pore, wherein the measurements are indicative of one or more characteristics of the polynucleotide, and thereby characterising the polynucleotide.

The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The protein may modify the polynucleotide by orienting it or moving it to a specific position, i.e. controlling its movement.

The polynucleotide binding protein is preferably derived from a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases. Suitable enzymes include, but are not limited to, exonuclease I from *E. coli* (SEQ ID NO: 11), exonuclease III enzyme from *E. coli* (SEQ ID NO: 13), RecJ from *T. thermophilus* (SEQ ID NO: 15) and bacteriophage lambda exonuclease (SEQ ID NO: 17), TatD exonuclease and variants thereof. Three subunits comprising the sequence shown in SEQ ID NO: 15 or a variant thereof interact to form a trimer exonuclease. The polymerase may be PyroPhage® 3173 DNA Polymerase (which is commercially available from Lucigen® Corporation), SD Polymerase (commercially available from Bioron®) or variants thereof. The enzyme is preferably Phi29 DNA polymerase (SEQ ID NO: 9) or a variant thereof. The topoisomerase is preferably a member of any of the Moiety Classification (EC) groups 5.99.1.2 and 5.99.1.3.

The enzyme is most preferably derived from a helicase, such as Hel308 Mbu (SEQ ID NO: 18), Hel308 Csy (SEQ ID NO: 19), Hel308 (Tga), Hel308 Mhu (SEQ ID NO: 21), TraI Eco (SEQ ID NO: 22), XPD Mbu (SEQ ID NO: 23) or a variant thereof. Any helicase may be used in the invention. The helicase may be or be derived from a Hel308 helicase, a RecD helicase, such as TraI helicase or a TrwC helicase, a XPD helicase or a Dda helicase. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925 (published as WO 2014/013260); PCT/GB2013/051924 (published as WO 2014/013259); PCT/GB2013/051928 (published as WO 2014/013262); PCT/GB2014/052736 (published as WO 2015/055981) and PCT/GB2015/052916.

The helicase preferably comprises the sequence shown in SEQ ID NO: 25 (Trwc Cba) or a variant thereof, the sequence shown in SEQ ID NO: 18 (Hel308 Mbu) or a variant thereof or the sequence shown in SEQ ID NO: 24 (Dda) or a variant thereof. Variants may differ from the native sequences in any of the ways discussed below for transmembrane pores. A preferred variant of SEQ ID NO: 24 comprises (a) E94C and A360C or (b) E94C, A360C, C109A and C136A and then optionally (ΔM1)G1G2 (i.e. deletion of M1 and then addition G1 and G2).

Any number of helicases may be used in accordance with the invention. For instance, 1, 2, 3, 4, 5, 6, 7, 8, 9, 10 or more helicases may be used. In some embodiments, different numbers of helicases may be used.

The method of the invention preferably comprises contacting the polynucleotide with two or more helicases. The two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs for use in the invention are described in International Application Nos. PCT/GB2013/051925 (published as WO 2014/013260); PCT/GB2013/051924 (published as WO 2014/013259); PCT/GB2013/051928 (published as WO 2014/013262); PCT/GB2014/052736 (published as WO 2015/055981) and PCT/GB2015/052916.

A variant of SEQ ID NOs: 9, 11, 13, 15, 17, 18, 19, 20, 21, 22, 23, 24 or 25 is an enzyme that has an amino acid sequence which varies from that of SEQ ID NO: 9, 11, 13, 15, 17, 18, 19, 20, 21, 22, 23, 24 or 25 and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature. Variants may be modified such that they bind polynucleotides (i.e. retain polynucleotide binding ability) but do not function as a helicase (i.e. do not move along polynucleotides when provided with all the necessary components to facilitate movement, e.g. ATP and $Mg^{2+}$). Such modifications are known in the art. For instance, modification of the $Mg^{2+}$ binding domain in helicases typically results in variants which do not function as helicases. These types of variants may act as molecular brakes (see below).

Over the entire length of the amino acid sequence of SEQ ID NO: 9, 11, 13, 15, 17, 18, 19, 20, 21, 22, 23, 24 or 25, a variant will preferably be at least 50% homologous to that sequence based on amino acid similarity or identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid similarity or identity to the amino acid sequence of SEQ ID NO: 9, 11, 13, 15, 17, 18, 19, 20, 21, 22, 23, 24 or 25 over the entire sequence. There may be at least 80%, for example at least 85%, 90% or 95%, amino acid similarity or identity over a stretch of 200 or more, for example 230, 250, 270, 280, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NO: 2 and 4 above. The enzyme may be covalently attached to the pore. Any method may be used to covalently attach the enzyme to the pore.

A preferred molecular brake is TrwC Cba-Q594A (SEQ ID NO: 25 with the mutation Q594A). This variant does not function as a helicase (i.e. binds polynucleotides but does not move along them when provided with all the necessary components to facilitate movement, e.g. ATP and $Mg^{2+}$).

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Any helicase may be used in the method. Helicases may work in two modes with respect to the pore. First, the method is preferably carried out using a helicase such that it moves the polynucleotide through the pore with the field resulting from the applied voltage. In this mode the 5' end of the polynucleotide is first captured in the pore, and the helicase moves the polynucleotide into the pore such that it is passed through the pore with the field until it finally translocates through to the trans side of the membrane. Alternatively, the method is preferably carried out such that a helicase moves the polynucleotide through the pore against the field resulting from the applied voltage. In this mode the 3' end of the polynucleotide is first captured in the pore, and the helicase moves the polynucleotide through the pore such that it is pulled out of the pore against the applied field until finally ejected back to the cis side of the membrane.

The method may also be carried out in the opposite direction. The 3' end of the polynucleotide may be first captured in the pore and the helicase may move the polynucleotide into the pore such that it is passed through the pore with the field until it finally translocates through to the trans side of the membrane.

When the helicase is not provided with the necessary components to facilitate movement or is modified to hinder or prevent its movement, it can bind to the polynucleotide and act as a brake slowing the movement of the polynucleotide when it is pulled into the pore by the applied field. In the inactive mode, it does not matter whether the polynucleotide is captured either 3' or 5' down, it is the applied field which pulls the polynucleotide into the pore towards the trans side with the enzyme acting as a brake. When in the inactive mode, the movement control of the polynucleotide by the helicase can be described in a number of ways including ratcheting, sliding and braking. Helicase variants which lack helicase activity can also be used in this way.

The polynucleotide may be contacted with the polynucleotide binding protein and the pore in any order. It is preferred that, when the polynucleotide is contacted with the polynucleotide binding protein, such as a helicase, and the pore, the polynucleotide firstly forms a complex with the protein. When the voltage is applied across the pore, the polynucleotide/protein complex then forms a complex with the pore and controls the movement of the polynucleotide through the pore.

Any steps in the method using a polynucleotide binding protein are typically carried out in the presence of free nucleotides or free nucleotide analogues and an enzyme cofactor that facilitates the action of the polynucleotide binding protein. The free nucleotides may be one or more of any of the individual nucleotides discussed above. The free nucleotides include, but are not limited to, adenosine mono-phosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cyti-dine diphosphate (CDP), cytidine triphosphate (CTP), cyclic adenosine monophosphate (cAMP), cyclic guanosine mono-phosphate (cGMP), deoxyadenosine monophosphate (dAMP), deoxyadenosine diphosphate (dADP), deoxyade-nosine triphosphate (dATP), deoxyguanosine monophos-phate (dGMP), deoxyguanosine diphosphate (dGDP), deox-yguanosine triphosphate (dGTP), deoxythymidine monophosphate (dTMP), deoxythymidine diphosphate (dTDP), deoxythymidine triphosphate (dTTP), deoxyuri-dine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

Helicase(s) and Molecular Brake(s)

In a preferred embodiment, the method comprises:

(a) providing the polynucleotide with one or more heli-cases and one or more molecular brakes attached to the polynucleotide;

(b) contacting the polynucleotide with a pore of the invention and applying a potential across the pore such that the one or more helicases and the one or more molecular brakes are brought together and both control the movement of the polynucleotide through the pore;

(c) taking one or more measurements as the polynucle-otide moves with respect to the pore wherein the measurements are indicative of one or more character-istics of the polynucleotide and thereby characterising the polynucleotide.

This type of method is discussed in detail in the Interna-tional Application PCT/GB2014/052737 (published as WO2015/110777).

The one or more helicases may be any of those discussed above. The one or more molecular brakes may be any compound or molecule which binds to the polynucleotide and slows the movement of the polynucleotide through the pore. The one or more molecular brakes preferably comprise one or more compounds which bind to the polynucleotide. The one or more compounds are preferably one or more macrocycles. Suitable macrocycles include, but are not limited to, cyclodextrins, calixarenes, cyclic peptides, crown ethers, cucurbiturils, pillararenes, derivatives thereof or a combination thereof. The cyclodextrin or derivative thereof may be any of those disclosed in Eliseev, A. V., and Schneider, H-J. (1994) *J. Am. Chem. Soc.* 116, 6081-6088. The agent is more preferably heptakis-6-amino-β-cyclodex-trin (am$_7$-βCD), 6-monodeoxy-6-monoamino-β-cyclodex-trin (am$_1$-βCD) or heptakis-(6-deoxy-6-guanidino)-cyclo-dextrin (gu$_7$-βCD).

The one or more molecular brakes are preferably one or more single stranded binding proteins (SSB). The one or more molecular brakes are more preferably a single-stranded binding protein (SSB) comprising a carboxy-terminal (C-terminal) region which does not have a net negative charge or (ii) a modified SSB comprising one or more modifications in its C-terminal region which decreases the net negative charge of the C-terminal region. The one or more molecular brakes are most preferably any of the SSBs disclosed in International Application No. PCT/GB2013/051924 (published as WO 2014/013259).

The one or more molecular brakes are preferably one or more polynucleotide binding proteins. The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucle-otide by cleaving it to form individual nucleotides or shorter chains of nucleotides, such as di- or trinucleotides. The moiety may modify the polynucleotide by orienting it or moving it to a specific position, i.e. controlling its move-ment.

The polynucleotide binding protein is preferably derived from a polynucleotide handling enzyme. The one or more molecular brakes may be derived from any of the polynucle-otide handling enzymes discussed above. Modified versions of Phi29 polymerase (SEQ ID NO: 8) which act as molecu-lar brakes are disclosed in U.S. Pat. No. 5,576,204. The one or more molecular brakes are preferably derived from a helicase.

Any number of molecular brakes derived from a helicase may be used. For instance, 1, 2, 3, 4, 5, 6, 7, 8, 9, 10 or more helicases may be used as molecular brakes. If two or more helicases are used as molecular brakes, the two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. The one or more molecular brakes derived from helicases are preferably modified to reduce the size of an opening in the polynucle-otide binding domain through which in at least one confor-mational state the polynucleotide can unbind from the helicase. This is disclosed in WO 2014/013260.

Preferred helicase constructs for use in the invention are described in International Application Nos. PCT/GB2013/051925 (published as WO 2014/013260); PCT/GB2013/051924 (published as WO 2014/013259); PCT/GB2013/051928 (published as WO 2014/013262) and PCT/GB2014/052736 (published as WO 2015/055981).

Spacers

The one or more helicases may be stalled at one or more spacers as discussed in International Application No. PCT/

GB2014/050175 (published as WO 2014/135838). Any configuration of one or more helicases and one or more spacers disclosed in the International Application may be used in this invention.

Membrane

The pore of the invention may be present in a membrane. In the method of the invention, the polynucleotide is typically contacted with the pore of the invention in a membrane. Any membrane may be used in accordance with the invention. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviours from vesicles through to laminar membranes. Membranes formed from these triblock copolymers hold several advantages over biological lipid membranes. Because the triblock copolymer is synthesized, the exact construction can be carefully controlled to provide the correct chain lengths and properties required to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customize polymer based membranes for a wide range of applications.

The membrane is most preferably one of the membranes disclosed in International Application No. PCT/GB2013/052766 (published as WO 2014/064443) or PCT/GB2013/052767 (published as WO 2014/064444).

The amphiphilic molecules may be chemically-modified or functionalised to facilitate coupling of the polynucleotide.

The amphiphilic layer may be a monolayer or a bilayer. The amphiphilic layer is typically planar. The amphiphilic layer may be curved. The amphiphilic layer may be supported.

Amphiphilic membranes are typically naturally mobile, essentially acting as two dimensional fluids with lipid diffusion rates of approximately $10^{-8}$ cm s$^{-1}$. This means that the pore and coupled polynucleotide can typically move within an amphiphilic membrane.

The membrane may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Coupling

The polynucleotide is preferably coupled to the membrane comprising the pore of the invention. The method may comprise coupling the polynucleotide to the membrane comprising the pore of the invention. The polynucleotide is preferably coupled to the membrane using one or more anchors. The polynucleotide may be coupled to the membrane using any known method. Suitable coupling methods are disclosed in International Application No. PCT/GB2012/051191 (published as WO 2012/164270) and PCT/GB2015/050991 (published as WO 2015/150786).

Double Stranded Polynucleotide

The polynucleotide may be double stranded. If the polynucleotide is double stranded, the method preferably further comprises before the contacting step ligating a bridging moiety, such as a hairpin loop, to one end of the polynucleotide. The two strands of the polynucleotide may then be separated as or before the polynucleotide is contacted with the pore in accordance with the invention. The two strands may be separated as the polynucleotide movement through the pore is controlled by a polynucleotide binding protein, such as a helicase, or molecular brake.

Linking and interrogating both strands on a double stranded construct in this way increases the efficiency and accuracy of characterisation as described in PCT/GB2010/000160 (published as WO 2010/086622) and PCT/GB2012/051786 (published as WO 2013/014451).

Modified Polynucleotides

Before characterisation, a target polynucleotide may be modified by contacting the polynucleotide with a polymerase and a population of free nucleotides under conditions in which the polymerase forms a modified polynucleotide using the target polynucleotide as a template, wherein the polymerase replaces one or more of the nucleotide species in the target polynucleotide with a different nucleotide species when forming the modified polynucleotide. The modified polynucleotide may then be provided with one or more helicases attached to the polynucleotide and one or more molecular brakes attached to the polynucleotide. This type of modification is described in International Application No. PCT/GB2015/050483 (published as WO2015/124935). Any of the polymerases discussed above may be used. The polymerase is preferably Klenow or 9° North.

Other Characterisation Method

In another embodiment, a polynucleotide is characterised by detecting labelled species that are released as a polymerase incorporates nucleotides into the polynucleotide. The polymerase uses the polynucleotide as a template. Each labelled species is specific for each nucleotide. The polynucleotide is contacted with a pore of the invention, a polymerase and labelled nucleotides such that phosphate labelled species are sequentially released when nucleotides are added to the polynucleotide(s) by the polymerase, wherein the phosphate species contain a label specific for each nucleotide. The polymerase may be any of those discussed above. The phosphate labelled species are detected using the pore and thereby characterising the polynucleotide. This type of method is disclosed in European Application No. 13187149.3 (published as EP 2682460). Any of the embodiments discussed above equally apply to this method.

Kits

The present invention also provides a kit for characterising a target polynucleotide. The kit comprises a hetero-oligomeric pore of the invention and the components of a membrane. The membrane is preferably formed from the components. The pore is preferably present in the membrane. The kit may comprise components of any of the membranes disclosed above, such as an amphiphilic layer or a triblock copolymer membrane.

The kit may further comprise a polynucleotide binding protein.

The kit may further comprise one or more anchors for coupling the polynucleotide to the membrane.

The kit is preferably for characterising a double stranded polynucleotide and preferably comprises a Y adaptor and a bridging moiety adaptor, such as a hairpin loop adaptor. The Y adaptor preferably has one or more helicases attached and the bridging moiety adaptor or hairpin loop adaptor preferably has one or more molecular brakes attached. The Y adaptor preferably comprises one or more first anchors for coupling the polynucleotide to the membrane, the bridging moiety adaptor or hairpin loop adaptor preferably comprises one or more second anchors for coupling the polynucleotide to the membrane and the strength of coupling of the bridging moiety adaptor or hairpin loop adaptor to the membrane is preferably greater than the strength of coupling of the Y adaptor to the membrane.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides or voltage or patch clamp apparatus. Reagents may be present in the kit in a dry state such that a fluid sample resuspends the reagents. The kit may also, optionally, comprise instructions to enable the kit to be used in the method of the invention or details regarding for which organism the method may be used.

Apparatus

The invention also provides an apparatus for characterising a target polynucleotide. The apparatus comprises a plurality of hetero-oligomeric pores of the invention and a plurality of membranes. The plurality of pores are preferably present in the plurality of membranes. The number of pores and membranes is preferably equal. Preferably, a single pore is present in each membrane.

The apparatus preferably further comprises instructions for carrying out the method of the invention. The apparatus may be any conventional apparatus for polynucleotide analysis, such as an array or a chip. Any of the embodiments discussed above with reference to the methods of the invention are equally applicable to the apparatus of the invention. The apparatus may further comprise any of the features present in the kit of the invention.

The apparatus is preferably set up to carry out the method of the invention.

The apparatus preferably comprises:

a sensor device that is capable of supporting the plurality of pores and membranes and being operable to perform polynucleotide characterisation using the pores and membranes; and at least one port for delivery of the material for performing the characterisation.

Alternatively, the apparatus preferably comprises:

a sensor device that is capable of supporting the plurality of pores and membranes being operable to perform polynucleotide characterisation using the pores and membranes; and at least one reservoir for holding material for performing the characterisation.

The apparatus more preferably comprises:

a sensor device that is capable of supporting the membrane and plurality of pores and membranes and being operable to perform polynucleotide characterising using the pores and membranes;

at least one reservoir for holding material for performing the characterising;

a fluidics system configured to controllably supply material from the at least one reservoir to the sensor device; and one or more containers for receiving respective samples, the fluidics system being configured to supply the samples selectively from one or more containers to the sensor device.

The apparatus may be any of those described in International Application No. PCT/GB08/004127 (published as WO 2009/077734), PCT/GB10/000789 (published as WO 2010/122293), International Application No. PCT/GB10/002206 (published as WO 2011/067559) or International Application No. PCT/US99/25679 (published as WO 00/28312).

Methods of Forming Sensors

The invention also provides a method of forming a sensor for characterising a target polynucleotide. The method comprises forming a complex between a hetero-oligomeric pore of the invention and a polynucleotide binding protein, such as a helicase or an exonuclease. The complex may be formed by contacting the pore and the protein in the presence of the target polynucleotide and then applying a potential across the pore. The applied potential may be a chemical potential or a voltage potential as described above. Alternatively, the complex may be formed by covalently attaching the pore to the protein. Methods for covalent attachment are known in the art and disclosed, for example, in International Application Nos. PCT/GB09/001679 (published as WO 2010/004265) and PCT/GB10/000133 (published as WO 2010/

086603). The complex is a sensor for characterising the target polynucleotide. The method preferably comprises forming a complex between a hetero-oligomeric pore of the invention and a helicase. Any of the embodiments discussed above equally apply to this method.

The invention also provides a sensor for characterising a target polynucleotide. The sensor comprises a complex between a hetero-oligomeric pore of the invention and a polynucleotide binding protein. Any of the embodiments discussed above equally apply to the sensor of the invention.

The following Example illustrates the invention.

EXAMPLE 1

This example describes a scaled up *E. coli* purification method that was used to purify an MspA hetero-oligomeric pore. The production of the mutant hetero-oligomeric nanopore MspA 1=MspA—((Del-L74/G75/D118/L119)D56N/E59R/L88N/D90N/D91N/Q126R/D134R/E139K)7((Del-L74/G75/D118/L119)D56N/E59R/L88N/D91N/Q126R/D134R/E139K/BasTL)1 (SEQ ID NO: 2 with the following mutations in seven monomers D56N/E59R/L88N/D90N/D91N/Q126R/D134R/E139K and deletion, of the following amino acids in seven monomers L74/G75/D118/L119 and the following mutations in one monomer of D56N/E59R/L88N/D91N/Q126R/D134R/E139K/BasTL, where the BasTL has SEQ ID NO: 26 and is attached at the C-terminus, and deletions of the following amino acids in one monomer of L74/G75/D118/L119) is described below. This method is suitable for making other hetero-oligomeric nanopores.

DNA encoding the polypeptide (SEQ ID NO: 27) for MspA—((Del-L74/G75/D118/L119)D56N/E59R/L88N/D90N/D91N/Q126R/D134R/E139K) (SEQ ID NO: 2 with the following mutations in the monomer D56N/E59R/L88N/D90N/D91N/Q126R/D134R/E139K and deletion, of the following amino acids in the monomers L74/G75/D118/L119) was synthesised (GenScript USA Inc.) and cloned into a pRham vector containing kanamycin resistance gene. Protein expression of the pRham vector can be induced by rhamnose. DNA encoding the polypeptide (SEQ ID NO: 28) MspA—(Del-L74/G75/D118/L119)D56N/E59R/L88N/D91N/Q126R/D134R/E139K/BasTL/H6) (SEQ ID NO: 2 with the following mutations in the monomer of D56N/E59R/L88N/D91N/Q126R/D134R/E139K/BasTL, where the BasTL has SEQ ID NO: 26 and is attached at the C-terminus, the six histidines (H6) are attached at the 3' end of the BasTL at the C-terminus and deletions of the following amino acids in one monomer of L74/G75/D118/L119) was synthesised (GenScript USA Inc) and cloned into a pT7 vector containing ampicillin resistance gene. Protein expression of the pT7 vector can be induced by IPTG (Isopropyl β-D-thiogalactopyranoside). Concentrations of both DNA solutions were adjusted to 400 ng/uL. The two DNA solutions were then mixed together in a 1:1 ratio and 1 uL of the mixture was used to transform Lemo21(DE3) competent *E. coli* cells (50 μl, NEB, catalogue number C2528H). The transformed cells were then incubated with SOC media (100 μl) with agitation at 37° C. for 2 hours. Cells were then plated out on LB agar containing both ampicillin (0.1 mg/ml) and kanamycin (0.034 mg/ml) and incubated for approx 16 hours at 37° C.

Bacterial colonies which grew in LB plates containing both ampicillin and kanamycin had been transformed with both plasmids: PRham containing the DNA of MspA—((Del-L74/G75/D118/L119)D56N/E59R/L88N/D90N/D91N/Q126R/D134R/E139K) and the pT7 containing the DNA of MspA—(Del-L74/G75/D118/L119)D56N/E59R/L88N/D91N/Q126R/D134R/E139K/BasTL/H6). One such colony was used to inoculate a starter culture of Terrific Broth (TB) media (10 mL) containing both ampicillin (0.1 mg/ml) and kanamycin (0.034 mg/ml). The starter culture was grown at 37° C. with agitation until OD600 was reached to 0.8-1.0. 1 mL of the starter culture was then used to inoculate 500 mL of TB media containing both ampicillin (0.1 mg/ml) and kanamycin (0.034 mg/ml). The culture was grown at 37° C. with agitation until OD600 was reached to 0.8-1.0. The temperature of the culture was then adjusted to 18° C. and induction was initiated by the addition of both IPTG (0.5 mM final concentration) and rhamnose (1.5% final concentration). Induction was carried out for approximately 18 hours with agitation at 18° C.

Following induction, the culture was pelleted by centrifugation at 6,000 g for 30 minutes. The pellet was then resuspended in 50 mM Tris pH9.0 (approximately 12.5 ml of buffer per gram of pellet). The suspension was mixed well until it was fully homogeneous. Lysis of cells was carried out by sonication (6×30 seconds on, 6×30 seconds off). DDM was added to the cell lysate to 1% final concentration and the mixture was incubated at 37° C. for 45 minutes with frequent mixing. The lysate was pelleted by centrifugation at 20,000 g for 45 minutes and the supernatant was then separated. The supernatant which contained both forms of monomers and a mixture of different oligomers was purified by column chromatography as described below.

The sample was diluted 1:1 with 50 mM Tris, 500 mM NaCl, 0.1% DDM, pH 8.0 (buffer A) and applied to a 5 ml His Crude FF column (GE Healthcare). The column was washed until a stable baseline of 10 column volumes was maintained. Loosely bound protein was removed by washing the column with 15 mM Imidazole (Sigma/Aldrich Biopuriss grade) until a stable base line was maintained. Elution was carried out with 200 mM imidazole (Sigma/Aldrich Biopuriss grade).

The elution peak was pooled and heated to 85° C. for 15 minutes to remove heat unstable contaminated proteins. The heated solution was then subjected to centrifugation at 20,000 g for 10 minutes and the pellet discarded. The supernatant was subjected to gel filtration on a 120 ml Sephadex S200 column (GE Healthcare) in buffer A at 1 ml/min. The sample was eluted at approximately 60 ml volume. The elution peak was run on a 10% TGX (Bio Rad) to confirm the presence of the heteropore of interest MspA 1. Identified fractions were pooled and carried forward for further purification.

The sample was loaded onto a 1 ml His HP column (GE Healthcare) in buffer A. Once a stable baseline was maintained for 10 column volumes, the column was washed with 15 mM imidazole (Sigma/Aldrich Biopuriss grade). Elution of MspA 1 was carried out with a gradient of 15 mM imidazole to 80 mM imidazole (Sigma/Aldrich Biopuriss grade) at 1 ml/min over 60 minutes. Other conformations of hetero pores containing more than one His tag were eluted by increasing the imidazole concentration in the elution to 100 mM.

The hetero-oligomeric nanopores listed below were also made using this method. In each case, DNA encoding the non-tagged subunits was cloned in the pRham vector and the DNA encoding the subunit containing BasTL-H6 was cloned in the pT7 vector and purified as explained in the above example.

MspA 2=MspA—((Del-L74/G75/D118/L119)D56N/E59R/L88N/D90N/D91N/N108P/Q126R/D134R/E139K)7((Del-L74/G75/D118/L119)D56N/E59R/

L88N/D91N/N108P/Q126R/D134R/E139K/BasTL/
H6)1 (SEQ ID NO: 2 with the following mutations in
seven monomers D56N/E59R/L88N/D90N/D91N/
N108P/Q126R/D134R/E139K and deletion, of the fol-
lowing amino acids in seven monomers L74/G75/
D118/L119 and the following mutations in one
monomer of D56N/E59R/L88N/D91N/N108P/Q126R/
D134R/E139K/BasTL/H6, where the BasTL has SEQ
ID NO: 26, the six histidines (H6) are attached at the 3'
end of the BasTL at the C-terminus and is attached at
the C-terminus, deletions of the following amino acids
in one monomer of L74/G75/D118/L119)

MspA 3=MspA—((Del-L74/G75/D118/L119)D56N/
E59R/L88N/D90N/D91N/N108P/Q126R/D134R/
E139K)7((Del-L74/G75/D118/L119)D56N/E59R/
L88N/D91G/N108P/Q126R/D134R/E139K/BasTL/
H6)1 (SEQ ID NO: 2 with the following mutations in
seven monomers D56N/E59R/L88N/D90N/D91N/
N108P/Q126R/D134R/E139K and deletion, of the fol-
lowing amino acids in seven monomers L74/G75/
D118/L119 and the following mutations in one
monomer of D56N/E59R/L88N/D91G/N108P/Q126R/
D134R/E139K/BasTL/H6, where the BasTL has SEQ
ID NO: 26, the six histidines (H6) are attached at the 3'
end of the BasTL at the C-terminus and is attached at
the C-terminus, deletions of the following amino acids
in one monomer of L74/G75/D118/L119)

MspA 4=MspA—((Del-L74/G75/D118/L119)D56F/
E59R/L88N/D90N/D91N/N108P/Q126R/D134R/
E139K)7((Del-L74/G75/D118/L119)D56F/E59R/
L88N/D91N/N108P/Q126R/D134R/E139K/BasTL/
H6)1 (SEQ ID NO: 2 with the following mutations in
seven monomers D56F/E59R/L88N/D90N/D91N/
N108P/Q126R/D134R/E139K and deletion, of the fol-
lowing amino acids in seven monomers L74/G75/
D118/L119 and the following mutations in one
monomer of D56F/E59R/L88N/D91N/N108P/Q126R/
D134R/E139K/BasTL/H6, where the BasTL has SEQ
ID NO: 26, the six histidines (H6) are attached at the 3'
end of the BasTL at the C-terminus and is attached at
the C-terminus, deletions of the following amino acids
in one monomer of L74/G75/D118/L119)

MspA 5=MspA—((Del-L74/G75/D118/L119)D56F/
E59R/L88N/D90N/D91N/N108P/Q126R/D134R/
E139K)7((Del-L74/G75/D118/L119)D56F/E59R/
L88N/D91G/N108P/Q126R/D134R/E139K/BasTL/
H6)1 (SEQ ID NO: 2 with the following mutations in
seven monomers D56F/E59R/L88N/D90N/D91N/
N108P/Q126R/D134R/E139K and deletion, of the fol-
lowing amino acids in seven monomers L74/G75/
D118/L119 and the following mutations in one
monomer of D56F/E59R/L88N/D91G/N108P/Q126R/
D134R/E139K/BasTL/H6, where the BasTL has SEQ
ID NO: 26, the six histidines (H6) are attached at the 3'
end of the BasTL at the C-terminus and is attached at
the C-terminus, deletions of the following amino acids
in one monomer of L74/G75/D118/L119)

MspA 7=MspA—((Del-L74/G75/D118/L119)(D56N/
E59R/L88N/D90N/D91N/N108P/Q126R/D134R/
E139K)7((Del-L74/G75/D118/L119)(D56N/E59R/
L88N/D91Q/N108P/Q126R/D134R/E139K/BasTL/
H6)1 (SEQ ID NO: 2 with the following mutations in
seven monomers D56N/E59R/L88N/D90N/D91N/
N108P/Q126R/D134R/E139K and deletion, of the fol-
lowing amino acids in seven monomers L74/G75/
D118/L119 and the following mutations in one
monomer of D56N/E59R/L88N/D91Q/N108P/Q126R/

D134R/E139K/BasTL/H6, where the BasTL has SEQ
ID NO: 26, the six histidines (H6) are attached at the 3'
end of the BasTL at the C-terminus and is attached at
the C-terminus, deletions of the following amino acids
in one monomer of L74/G75/D118/L119)

An example of the purified MspA 2 is shown in FIG. 1.
Proteins were analysed in a 10% TGX gel (BioRad) and
visualised with coomasie staining. Lane 3 shows the purified
MspA-2 with a band corresponding to a hetero-oligomeric
pore made up of 8 monomer units which have oligomerised.
Lane 4 shows the purified MspA-2 after heat treatment
which broke the pore down into its monomer units. Two
bands were observed in Lane 4—one which corresponded to
the monomer unit with the BasTL-H6 attached (band B) and
one which corresponded to the monomer unit without the
BasTL-H6 attached. This illustrated that the purified pore in
lane 8 broke down into two different monomer units which
was evidence that the MspA-2 heteropore had been formed.

EXAMPLE 2

This example describes a control experiment which
showed that co-transformation and subsequent controlled
expression of the two monomers was necessary to obtain the
hetero pores of interest. Two subunits which were trans-
formed individually, but grown together in the same culture
did not produce hetero-oligomeric pores.

DNA encoding polypeptide (SEQ ID NO: 27) MspA—
((Del-L74/G75/D118/L119)D56N/E59R/L88N/D90N/
D91N/Q126R//D134R/E139K) (SEQ ID NO: 2 with the
following mutations in the monomer D56N/E59R/L88N/
D90N/D91N/Q126R//D134R/E139K and deletion, of the
following amino acids in the monomers L74/G75/D118/
L119) and DNA encoding polypeptide (SEQ ID NO: 28)
MspA—((Del-L74/G75/D118/L119)D56N/E59R/L88N/
D91N/Q126R//D134R/E139K) (SEQ ID NO: 2 with the
following mutations in the monomer D56N/E59R/L88N/
D91N/Q126R//D134R/E139K and deletion, of the follow-
ing amino acids in the monomers L74/G75/D118/L119)
were cloned into the pT7 vector containing ampicilin resis-
tance gene. The two DNA encoding polypeptides were
transformed separately into BL21 DE3 PlysS competent
cells. Starter cultures were made by inoculating 10 ml of TB
media containing 0.1 mg/ml ampicillin with a single colony
from each transformant. Starter cultures were grown at 37°
C. with agitation to an OD600 of 0.8. 500 ml of TB media
containing 0.1 mg/ml ampicillin was inoculated with both
subunits by adding 1 ml of starter cultures of each subunit.
The inoculated culture was grown to an OD600 of 0.8. Once
the desired OD600 was reached, the culture was allowed to
cool to 18° C. and induced by the addition of 1 mM IPTG.
The culture was then incubated at 18° C. with agitation for
8 hours.

Following incubation, the sample was lysed as standard—
culture was pelleted by centrifugation at 6,000 g for 30
minutes and the pellet was resuspended in 50 mM Tris pH
9 (approximately 12.5 ml per gram of pellet). The suspen-
sion was mixed until fully homogeneous. Lysis was carried
out by sonication (6×30 seconds on, 6×30 seconds off).
DDM was added to the lysate (1% final concentration)
before incubation at 37° C. for 45 minutes with frequent
mixing. The lysate was pelleted by centrifugation at 20,000
g for 45 minutes. The samples were then visualised on 7.5%
Tris HCl gel pre and post heating to 85° C. to determine
whether hetero pore formation occurred.

For all of the samples tested no hetero pores were
observed. This confirmed that co-transformation of the same bacterial cell with the DNA encoding both subunits and subsequent induction of the expression in a controlled manner was necessary to obtain the heteropore of interest.

EXAMPLE 3

This example described a number of different conditions which were investigated in order to identify the optimised ratio of IPTG: Rhamnose that favoured stable 7:1 hetero pore formation.

In brief, pRham vector containing DNA encoding the polypeptide (SEQ ID NO: 29) for MspA—((Del-L74/G75/D118/L119)D56N/E59R/L88N/D90N/D91N/N108P/Q126R/D134R/E139K) (SEQ ID NO: 2 with the following mutations in the monomer D56N/E59R/L88N/D90N/D91N/Q126R/D134R/E139K and deletion, of the following amino acids in the monomers L74/G75/D118/L119) and the pT7 vector containing DNA encoding the polypeptide (SEQ ID NO: 30) for MspA—((Del-L74/G75/D118/L119)D56N/E59R/L88N/D91N/N108P/Q126R/D134R/E139K/BastL/H6) (SEQ ID NO: 2 with the following mutations in the monomer D56N/E59R/L88N/D90N/D91N/Q126R/D134R/E139K where the BasTL has SEQ ID NO: 26 and is attached at the C-terminus, the six histidines (H6) are attached at the 3' end of the BasTL at the C-terminus and deletions of the following amino acids in the monomers L74/G75/D118/L119) were co-transformed to Lemo21(DE3) competent *E. coli* cells and grown in 500 ml of TB media containing 0.1 mg/ml ampicillin and 0.034 mg/ml kanamycin as detailed above in Example 1. Once the culture had reached an OD600 of 0.85, it was aliquoted into 14×10 ml subcultures. Each subculture was induced with differing amounts of Rhamnose and IPTG as shown below:

1) 0.5% Rhamnose/1 mM IPTG
2) 1% Rhamnose/1 mM IPTG
3) 1% Rhamnose/0.5 mM IPTG
4) 1.5% Rhamnose/1 mM IPTG
5) 1.5% Rhamnose/0.5 mM IPTG
6) 2% Rhamnose/1 mM IPTG
7) 2% Rhamnose/0.5 mM IPTG
8) 3% Rhamnose/1 mM IPTG
9) 3% Rhamnose/0.5 mM IPTG
10) 1% Rhamnose/0.25 mM IPTG
11) 0.5% Rhamnose/0.5 mM IPTG
12) 0.5% Rhamnose/0.25 mM IPTG
13) 0% Rhamnose/1 mM IPTG
14) 0.5% Rhamnose/0 mM IPTG Induction was carried out for approximately 18 hours with agitation at 18° C. The cultures were pelleted by centrifugation at 6,000 g for 30 minutes. Pellets were resuspended in 50 mM Tris pH 9 (approx 12.5 ml per gram of pellet). Suspensions were mixed until fully homogeneous. Lysis was carried out by sonication (6×30 seconds on, 6×30 seconds off). DDM was added to the lysates (1% final concentration) before incubation at 37° C. for 45 minutes with frequent mixing. The lysates were pelleted by centrifugation at 20,000 g for 45 minutes.

Following solubilisation the samples were batch purified on Qiagen NiNTA sepharose beads as instructed by the manufacturer. The elution was split into two aliquots. One aliquot was kept unheated and the other aliquot was heated to 85° C. to assess heat stability before both samples were visualised on 10% TGX (bio rad) gel. Gel analysis confirmed that condition 5 with 1.5% Rhamnose and 0.5 mM IPTG gave the most amount of stable heteropore of interest MspA-2.

EXAMPLE 4

This example describes how a number of different tags were investigated for their ability to alter the oligomerisation efficiency of monomers. For the purpose of this experiment, different tags of various lengths and charges were added to the N or C termini of the MspA monomer MspA—(G75S/G77S/L88N/D90N/D91N/D93N/D118R/Q126R/D134R/E139K) (SEQ ID NO: 2 with the following mutations G75S/G77S/L88N/D90N/D91N/D93N/D118R/Q126R/D134R/E139K). DNA for such constructs was generated by PCR methods known in the art. The circular DNA plasmid containing the T7 promoter and DNA of MspA—(G75S/G77S/L88N/D90N/D91N/D93N/D118R/Q126R/D134R/E139K) (SEQ ID NO: 2 with the following mutations G75S/G77S/L88N/D90N/D91N/D93N/D118R/Q126R/D134R/E139K) with or without tags was prepared by QIAGEN Plasmid Midi Kit (catalogue number 12145) and the concentration of samples adjusted to 400 ng/uL. Proteins were generated by coupled in vitro transcription and translation (IVTT) by using an *Escherichia coli* T7-S30 extract system for circular DNA (Promega, no. L1130). Prepared rabbit red blood cell membranes (rRBCM) were used to facilitate oligomerisation of monomers into their oligomer. DNA (16 ul, 400 ng/ul) of the monomer of interest was used in a 100 uL IVTT reaction which generated homo-oligomeric pores where all monomers in the oligomer are identical. DNA for two monomers (eg: a tagged and untagged versions) were mixed together in specific ratios and the DNA mixture (16 µl, 400 ng/uL) was used in a 100 uL IVTT reaction to generate hetero-oligomeric pores. Depending on the ratio of DNA (untagged:tagged) used, a range of hetero-oligomers was produced (eg: 8:0, 7:1, 6:2, 5:3 etc.) within the reaction. Therefore, the ratio of DNA between the two monomers was adjusted to bias the desired oligomeric pores produced (eg: more of 8:0, 7:1 rather than 3:5, 2:6).

To generate proteins in IVTT, 50 uL of rRBCM (10 mM Mops pH 7.4, 2 mg/mL) were centrifuged in 1.5 mL Eppendorf tube and the supernatant was removed. The pellet was resuspended in IVTT reagents required to carry out a 100 uL IVTT reaction. The complete amino acid mixture (1 mM) minus cysteine and the complete amino acid mixture (1 mM) minus methionine, supplied in the kit, were mixed in equal volumes which produced the working amino acid solution required to generate high concentrations of the proteins. 10 uL of this amino acid mixture was mixed with the premix solution (40 uL), L-[35S]methionine (2 uL, PerkinElmer, product code NEG009A001MC), plasmid DNA as mentioned above (16 uL, 400 ng/uL), and T7-S30 extract (30 uL) supplemented with rifampicin (20 µg/ml final). Protein synthesis was carried out for 1.5 hours at 37° C. to produce radiolabelled IVTT protein. Due to the presence of rRBCM and *E. coli* cell membranes in the IVTT reaction mixture, monomers synthesized within the reaction assembled on the membranes to produce homo or hetero-oligomeric nanopores. After centrifugation, the resulting membrane pellets were washed with MBSA (100 uL, 10 mM MOPS titrated with NaOH, 150 mM NaCl, pH 7.4, containing 1 mg/ml BSA) and the pellets were resuspended in 100 uL of 1× laemmli sample buffer. The sample was divided into two and one sample was heated at 85° C. for 15 minutes to assess the heat stability of the oligomers. Heated and/or unheated samples were subjected to electrophoresis in 5% or 7.5% Tris HCl gels with TGS running buffer for 16 hours at 50 mV. The gels were dried and subjected to autoradiography to visualize the proteins.

4.1—Effect of the Length of the Tag

By changing the length of the tag, it was possible to bias the production of the desired oligomer. In the following example, MspA—(G75S/G77S/L88N/D90N/D91N/D93N/D118R/Q126R/D134R/E139K) (SEQ ID NO: 2 with the following mutations G75S/G77S/L88N/D90N/D91N/D93N/D118R/Q126R/D134R/E139K) was tagged with full length BasTL (SEQ ID NO: 26) and truncated versions of the BasTL. Tagged monomers were either oligomerised into their homo-oligomers or mixed with untagged MspA—(G75S/G77S/L88N/D90N/D91N/D93N/D118R/Q126R/D134R/E139K) (SEQ ID NO: 2 with the following mutations G75S/G77S/L88N/D90N/D91N/D93N/D118R/Q126R/D134R/E139K) to produce hetero-oligomers. Heated samples were run on a 7.5% Tris HCl gel (see FIG. 2).

Figure 2:
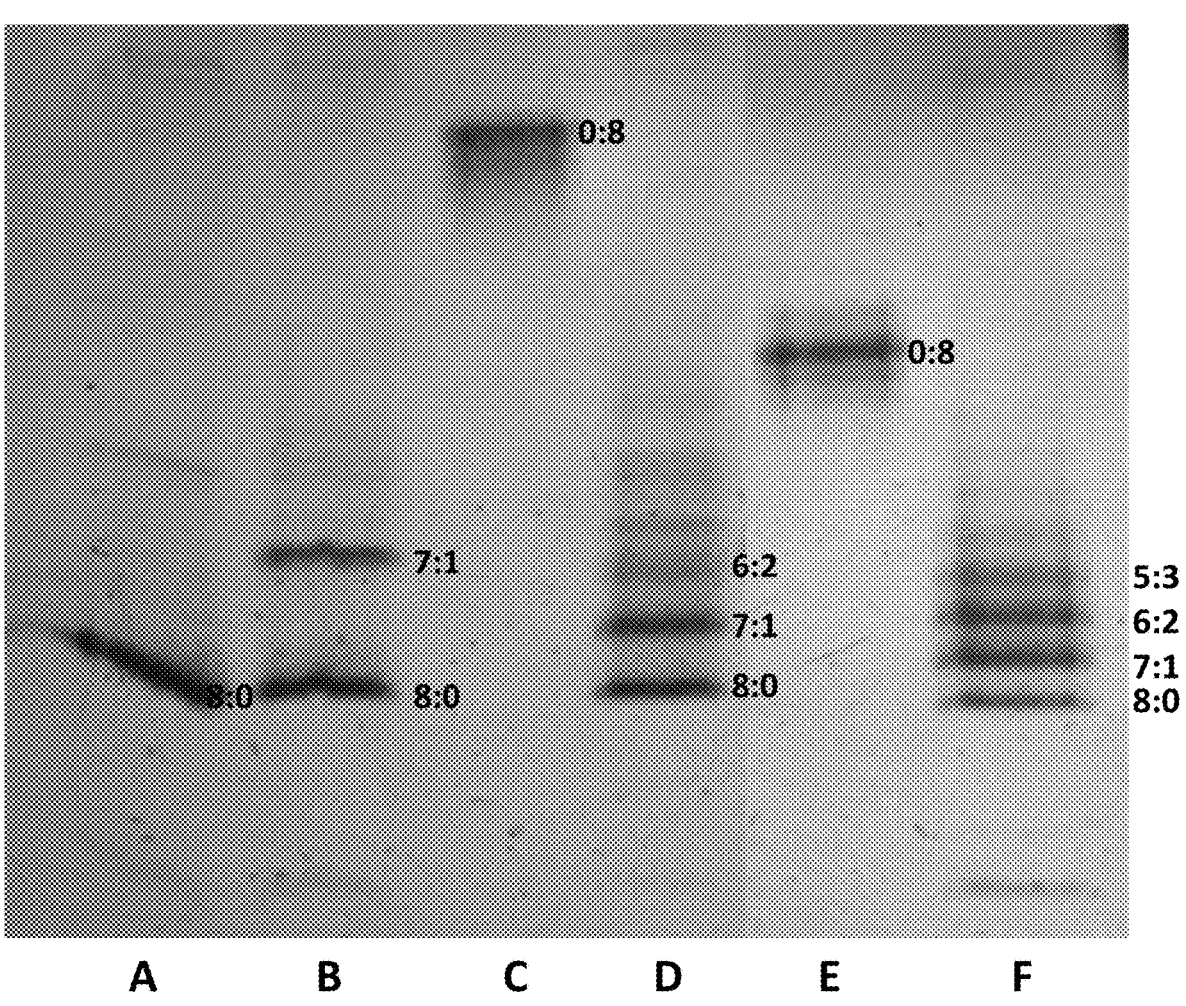
FIG. 2 shows a 7.5% Tris HCl gel which compares oligomerisation of MspA—(G75S/G77S/L88N/D90N/D91N/D93N/D118R/Q126R/D134R/E139K) (SEQ ID NO: 2 with the following mutations G75S/G77S/L88N/D90N/D91N/D93N/D118R/Q126R/D134R/E139K) with or without a BasTL tag of varying length. Lane A corresponded to homo-oligomer MspA—(G75S/G77S/L88N/D90N/D91N/D93N/D118R/Q126R/D134R/E139K)8 which had no tags attached to any of the monomers. Lane B corresponded to a 2:1 mixture of MspA—(G75S/G77S/L88N/D90N/D91N/D93N/D118R/Q126R/D134R/E139K) monomer and MspA—(G75S/G77S/L88N/D90N/D91N/D93N/D118R/Q126R/D134R/E139K/BasTL) monomer. Lane C corresponded to homo-oligomer MspA—(G75S/G77S/L88N/D90N/D91N/D93N/D118R/Q126R/D134R/E139K/BasTL (minus 20 aa))8. Lane D corresponded to a 2:1 mixture of MspA—(G75S/G77S/L88N/D90N/D91N/D93N/D118R/Q126R/D134R/E139K) monomer and MspA—(G75S/G77S/L88N/D90N/D91N/D93N/D118R/Q126R/D134R/E139K/BasTL(minus 20 aa)) monomer. Lane E corresponded to homo-oligomer MspA—(G75S/G77S/L88N/D90N/D91N/D93N/D118R/Q126R/D134R/E139K/BasTL(minus 40 aa))8. Lane F corresponded to a 2:1 mixture of MspA—(G75S/G77S/L88N/D90N/D91N/D93N/D118R/Q126R/D134R/E139K) monomer and MspA—(G75S/G77S/L88N/D90N/D91N/D93N/D118R/Q126R/D134R/E139K/BasTL(minus 40 aa)) monomer. The ratios quoted next to the gel bands correspond to the ratio of tagged monomer:non-tagged monomer.

Lane A of FIG. 2 shows the MspA—(G75S/G77S/L88N/D90N/D91N/D93N/D118R/Q126R/D134R/E139K)8 homo-oligomer. Lanes C and E show homo-oligomers for MspA—(G75S/G77S/L88N/D90N/D91N/D93N/D118R/Q126R/D134R/E139K/BasTL(minus20 aa))8 and MspA—(G75S/G77S/L88N/D90N/D91N/D93N/D118R/Q126R/D134R/E139K/BasTL(minus40 aa))8 respectively. Although the same amount of DNA was used in each experiment, the amount of homo-oligomer produced was diminished when a long polypeptide tag (BasTL in this instance) was attached (lanes C and E of FIG. 2) compared to the untagged version (lane A which showed a much darker band in FIG. 2). Lanes B, D and F of FIG. 2 showed hetero-oligomers produced when MspA—(G75S/G77S/L88N/D90N/D91N/D93N/D118R/Q126R/D134R/E139K) was mixed with MspA—(G75S/G77S/L88N/D90N/D91N/D93N/D118R/Q126R/D134R/E139K/BasTL), MspA—(G75S/G77S/L88N/D90N/D91N/D93N/D118R/Q126R/D134R/E139K/BasTL(minus20 aa)) and MspA—(G75S/G77S/L88N/D90N/D91N/D93N/D118R/Q126R/D134R/E139K/BasTL(minus40 aa)) respectively. Each band in each lane of FIG. 2 has the ratio of the monomer units which produced the band in the gel (untagged monomer:tagged monomer) marked next to the corresponding band. The results showed that by changing the length of the tag, it was possible to manipulate the production of desired hetero-oligomers.

4.2 Effect of Charges in the Tag

MspA—(G75S/G77S/L88N/D90N/D91N/D93N/D118R/Q126R/D134R/E139K) monomer was modified with various charged tags of different lengths at the N or C termini. Ability of these monomers to form pores was analysed in IVTT experiments. The full list of different tags tested included R8SG, D6SG, R6SG, R8, NGDSD6SG, D4SG, R4SG, D4, D6, GDSGD4SG, R4H6, D4H6, D8, R6, D10, R4, D4, D8H6, R8H9, D10H6, and R6H6. The MspA—(G75S/G77S/L88N/D90N/D91N/D93N/D118R/Q126R/D134R/E139K) monomer labelled with D10H6, R8 or R8H6 tags described in more detail below and in FIG. 3.

Figure 3:
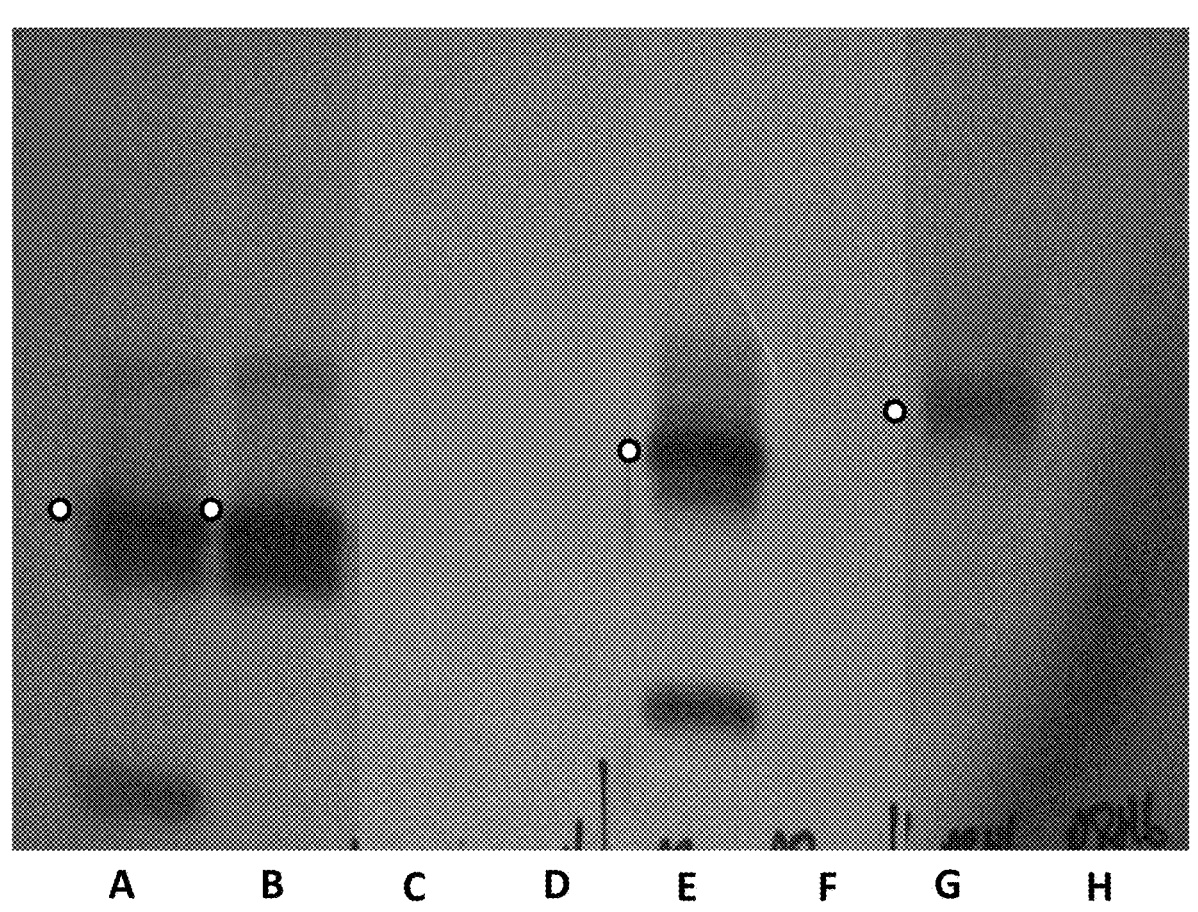
FIG. 3 shows 5% Tris HCl gel which compares oligomerisation of MspA—(G75S/G77S/L88N/D90N/D91N/D93N/D118R/Q126R/D134R/E139K) monomers when a variety of different tags were attached to the C terminus. Lane A corresponded to homo-oligomer MspA—(G75S/G77S/L88N/D90N/D91N/D93N/D118R/Q126R/D134R/E139K)8 which had no tags attached to any of the monomers. Lane B corresponded to homo-oligomer MspA—(G75S/G77S/L88N/D90N/D91N/D93N/D118R/Q126R/D134R/E139K)8 which had been heat treated at 85° C. for 15 minutes. Lane C corresponded to the attempt to oligomerise the homo-oligomer MspA—(G75S/G77S/L88N/D90N/D91N/D93N/D118R/Q126R/D134R/E139K/D10H6)8 (SEQ ID NO: 2 with the following mutations G75S/G77S/L88N/D90N/D91N/D93N/D118R/Q126R/D134R/E139K where there is a D10H6 tag attached at the C terminus). Lane D corresponded to the attempt to oligomerise the homo-oligomer MspA—(G75S/G77S/L88N/D90N/D91N/D93N/D118R/Q126R/D134R/E139K/D10H6)8 (SEQ ID NO: 2 with the following mutations G75S/G77S/L88N/D90N/D91N/D93N/D118R/Q126R/D134R/E139K where there is a D10H6 tag attached at the C terminus) which had been heat treated at 85° C. for 15 minutes. Lane E corresponded to the attempt to oligomerise the homo-oligomer MspA—(G75S/G77S/L88N/D90N/D91N/D93N/D118R/Q126R/D134R/E139K/R8)8 (SEQ ID NO: 2 with the following mutations G75S/G77S/L88N/D90N/D91N/D93N/D118R/Q126R/D134R/E139K where there is a R8 tag attached at the C terminus). Lane F corresponded to the attempt to oligomerise the homo-oligomer MspA—(G75S/G77S/L88N/D90N/D91N/D93N/

FIG. 3 shows 5% Tris HCl gel which compares oligomerisation of MspA—(G75S/G77S/L88N/D90N/D91N/D93N/D118R/Q126R/D134R/E139K) monomers when a variety of different tags were attached to the C terminus. White circles in FIG. 3 indicate the MspA homo-oligomer formed in each lane. Lanes A shows that the MspA—(G75S/G77S/L88N/D90N/D91N/D93N/D118R/Q126R/D134R/E139K) monomer without any tag at the C terminus oligomerised well. Lane B shows that the oligomer formed from the MspA—(G75S/G77S/L88N/D90N/D91N/D93N/D118R/Q126R/D134R/E139K) monomer was stable at least up to 85° C. Lane C shows that D10H6 tag at the C terminus of the MspA—(G75S/G77S/L88N/D90N/D91N/D93N/D118R/Q126R/D134R/E139K) monomer prevented it from oligomerising completely or at least the oligomer formed was not SDS stable. Lanes E and F show that although R8 tag at the C terminus of the MspA—(G75S/G77S/L88N/D90N/D91N/D93N/D118R/Q126R/D134R/E139K) monomer oligomerised well, heat stability of the oligomer had been compromised by that addition of the tag. Lane G shows that R8H6 tag at the C terminus of the MspA—(G75S/G77S/L88N/D90N/D91N/D93N/D118R/Q126R/D134R/E139K) monomer diminished its oligomerisation ability compared to the untagged monomer in lane A. Lane H shows that similar to the R8 tag, the R8H6 tag also compromised the heat stability of its oligomer.

The invention claimed is:

1. A method of characterising a target analyte, comprising:

(a) contacting the analyte with a hetero-oligomeric transmembrane pore such that the target analyte moves through the pore, wherein the pore comprises a first monomer and a second monomer at a specific stoichiometric ratio in the range of 1:13 to 13:1 and wherein the specific stoichiometric ratio is not 1:1, wherein the first monomer is different from the second monomer, and wherein:

(i) the first monomer comprises SEQ ID NO: 2, or 32 while the second monomer comprises a variant of SEQ ID NO: 2, or the first monomer comprises a variant of SEQ ID NO: 2 while the second monomer comprises SEQ ID NO: 2; or (ii) the first monomer comprises SEQ ID NO: 32 while the second monomer comprises a variant of SEQ ID NO: 32, or the first monomer comprises a variant of SEQ ID NO: 32 while the second monomer comprises SEQ ID NO: 32; and (b) taking one or more measurements as the target analyte moves with respect to the pore, wherein the measurements are indicative of one or more characteristics of the target analyte, and thereby characterising the target analyte.

2. The method of claim 1, wherein the one or more characteristics are selected from (i) the length of the target analyte, (ii) the identity of the target analyte, (iii) the sequence of the target analyte, (iv) the secondary structure of the target analyte and (v) whether or not the target analyte is modified.

3. The method of claim 1, wherein the one or more characteristics of the target analyte are measured by electrical measurement and/or optical measurement.

4. The method of claim 3, wherein the electrical measurement is a current measurement, an impedance measurement, a tunnelling measurement or a field effect transistor (FET) measurement.

5. The method of claim 1, wherein the pore is in a membrane.

6. The method of claim 5, wherein the membrane is an amphiphilic layer or a solid state layer.

7. The method of claim 1, wherein the specific stoichiometric ratio of the first monomer to the second monomer is at least 2:1, 3:1, 4:1, 5:1, 6:1, 7:1, or 8:1.

8. The method of claim 1, wherein the specific stoichio-metric ratio of the first monomer to the second monomer is 1:2, 2:1, 1:3, 3:1, 1:4, 2:3, 3:2, 4:1, 1:5, 1:6, 2:5, 3:4, 4:3, 5:2, 1:7, 3:5, 5:3, 1:8, 2:7, 4:5, 5:4, 7:2, 1:9, 3:7, 7:3, 5:1, 6:1, 7:1, 8:1, 9:1, 1:10, 2:9, 3:8, 4:7, 5:6, 6:5, 7:4, 8:3, 9:2, 10:1, 1:11, 5:7, 7:5, 11:1, 1:12, 2:11, 3:10, 4:9, 5:8, 6:7, 7:6, 8:5, 9:4, 10:3, 11:2, 12:1, 1:13, 3:11, 5:9, 9:5, 11:3, or 13:1.

9. The method of claim 1, wherein the variant of SEQ ID NO: 2 comprises an amino acid mutation at one or more of the positions corresponding to positions 88, 90, 91, 92, 93, 102, 103 and 105 of SEQ ID NO: 2.

10. The method of claim 1, wherein the variant of SEQ ID NO: 2 comprises a negatively charged amino acid at one or more of the positions corresponding to positions 90, 91, 93 and 105 of SEQ ID NO: 2.

11. The method of claim 1, wherein the variant of SEQ ID NO: 32 comprises an amino acid mutation at one or more of the positions corresponding to positions N40, D43, E44, S54, S57, Q62, R97, E101, E124, E131, R142, T150 and R192 of SEQ ID NO: 32.

* * * * *

SEQUENCE LISTING

```
<160> NUMBER OF SEQ ID NOS: 32

<210> SEQ ID NO 1
<211> LENGTH: 558
<212> TYPE: DNA
<213> ORGANISM: Mycobacterium smegmatis

<400> SEQUENCE: 1
atgggcctgg ataacgaact tagcctggtg gacggccaag atcgcacgct gacggtgcaa      60
caatgggata ccttcctgaa tggtgtgttt ccgctggatc gtaaccgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc gatgacggta atattaccgc accgccgttt     300
ggcctgaaca gcgtgattac gccgaacctg tttccgggtg ttagcatctc tgccgatctg     360
ggcaacggtc cgggcattca agaagtggca acctttagtg tggacgtttc cggcgctgaa     420
ggcggtgtcg cggtgtctaa tgcccacggt accgttacgg gcgcggccgg cggtgtcctg     480
ctgcgtccgt tcgcgcgcct gattgcgagc accggcgact ctgttacgac ctatggcgaa     540
```

```
ccgtggaata tgaactaa                                                 558

<210> SEQ ID NO 2
<211> LENGTH: 184
<212> TYPE: PRT
<213> ORGANISM: Mycobacterium smegmatis

<400> SEQUENCE: 2

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
            115                 120                 125

Ala Thr Phe Ser Val Asp Val Ser Gly Ala Glu Gly Gly Val Ala Val
        130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 3
<211> LENGTH: 885
<212> TYPE: DNA
<213> ORGANISM: Artificial Sequence
<220> FEATURE:
<223> OTHER INFORMATION: Synthetic polynucleotide

<400> SEQUENCE: 3
atggcagatt ctgatattaa tattaaaacc ggtactacag atattggaag caatactaca    60
gtaaaaacag tgatttagt cacttatgat aaagaaaatg gcatgcacaa aaaagtattt    120
tatagtttta tcgatgataa aaatcacaat aaaaaactgc tagttattag aacaaaaggt    180
accattgctg gtcaatatag agtttatagc gaagaaggtg ctaacaaaag tggtttagcc    240
tggccttcag cctttaaggt acagttgcaa ctacctgata atgaagtagc tcaaatatct    300
gattactatc caagaaattc gattgataca aaaaactata tgagtacttt aacttatgga    360
ttcaacggta atgttactgg tgatgataca ggaaaaattg gcggcctta tggtgcaaat    420 gtttcgattg tcatacact gaactatgtt caacctgatt caaaacaat tttagagagc    480 ccaactgata aaaagtagg ctggaaagtg atatttaaca atatggtgaa tcaaaattgg    540
ggaccatacg atcgagattc ttggaacccg gtatatggca atcaacttt catgaaaact    600 agaaatggtt ctatgaaagc agcagataac ttccttgatc ctaacaaagc aagttctcta    660
```

-continued

```
ttatcttcag ggttttcacc agacttcgct acagttatta ctatggatag aaaagcatcc      720
aaacaacaaa caaatataga tgtaatatac gaacgagttc gtgatgatta ccaattgcat      780
tggacttcaa caaattggaa aggtaccaat actaaagata aatggacaga tcgttcttca      840
gaaagatata aaatcgattg ggaaaaagaa gaaatgacaa attaa                      885
```

```
<210> SEQ ID NO 4
<211> LENGTH: 293
<212> TYPE: PRT
<213> ORGANISM: Artificial Sequence
<220> FEATURE:
<223> OTHER INFORMATION: Synthetic polypeptide

<400> SEQUENCE: 4

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
        130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

```
<210> SEQ ID NO 5
<211> LENGTH: 184
<212> TYPE: PRT
```

```
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
            115                 120                 125

Ala Thr Phe Ser Val Asp Val Ser Gly Pro Ala Gly Gly Val Ala Val
        130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
            165                 170                 175

Tyr Gly Glu Pro Trp Asn Met Asn
            180

<210> SEQ ID NO 6
<211> LENGTH: 184
<212> TYPE: PRT
<213> ORGANISM: Mycobacterium smegmatis

<400> SEQUENCE: 6

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
            115                 120                 125

Ala Thr Phe Ser Val Asp Val Ser Gly Pro Ala Gly Gly Val Ala Val
        130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
```

```
                165              170              175
Tyr Gly Glu Pro Trp Asn Met Asn
            180

<210> SEQ ID NO 7
<211> LENGTH: 183
<212> TYPE: PRT
<213> ORGANISM: Mycobacterium smegmatis

<400> SEQUENCE: 7

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180

<210> SEQ ID NO 8
<211> LENGTH: 1830
<212> TYPE: DNA
<213> ORGANISM: Bacillus subtilis phage phi29

<400> SEQUENCE: 8
atgaaacaca tgccgcgtaa aatgtatagc tgcgcgtttg aaaccacgac caaagtggaa       60
gattgtcgcg tttgggccta tggctacatg aacatcgaag atcattctga atacaaaatc      120
ggtaacagtc tggatgaatt tatggcatgg gtgctgaaag ttcaggcgga tctgtacttc      180
cacaacctga aatttgatgg cgcattcatt atcaactggc tggaacgtaa tggctttaaa      240
tggagcgcgg atggtctgcc gaacacgtat aataccatta tctctcgtat gggccagtgg      300
tatatgattg atatctgcct gggctacaaa ggtaaacgca aaattcatac cgtgatctat      360
gatagcctga aaaaactgcc gtttccggtg aagaaaattg cgaaagattt caaactgacg      420
gttctgaaag cgatattga ttatcacaaa gaacgtccgg ttggttacaa aatcaccccg      480
gaagaatacg catacatcaa aaacgatatc cagatcatcg cagaagcgct gctgattcag      540
tttaaacagg cctggatcg catgaccgcg ggcagtgata gcctgaaagg tttcaaagat      600
atcatcacga ccaaaaaatt caaaaaagtg ttcccgacgc tgagcctggg tctggataaa      660
```

```
gaagttcgtt atgcctaccg cggcggtttt acctggctga acgatcgttt caaagaaaaa    720
gaaattggcg agggtatggt gtttgatgtt aatagtctgt atccggcaca gatgtacagc    780
cgcctgctgc cgtatggcga accgatcgtg ttcgagggta aatatgtttg ggatgaagat    840
tacccgctgc atattcagca catccgttgt gaatttgaac tgaaagaagg ctatattccg    900
accattcaga tcaaacgtag tcgcttctat aagggtaacg aatacctgaa aagctctggc    960
ggtgaaatcg cggatctgtg gctgagtaac gtggatctgg aactgatgaa agaacactac   1020
gatctgtaca cgttgaata catcagcggc ctgaaattta aagccacgac cggtctgttc   1080
aaagatttca tcgataaatg gacctacatc aaaacgacct ctgaaggcgc gattaaacag   1140
ctggccaaac tgatgctgaa cagcctgtat ggcaaattcg cctctaatcc ggatgtgacc   1200
ggtaaagttc cgtacctgaa agaaaatggc gcactgggtt ttcgcctggg cgaagaagaa   1260
acgaaagatc cggtgtatac cccgatgggt gttttcatta cggcctgggc acgttacacg   1320
accatcaccg cggcccaggc atgctatgat cgcattatct actgtgatac cgattctatt   1380
catctgacgg gcaccgaaat cccggatgtg attaaagata tcgttgatcc gaaaaaactg   1440
ggttattggg cccacgaaag tacgtttaaa cgtgcaaat acctgcgcca gaaaacctac   1500
atccaggata tctacatgaa agaagtggat ggcaaactgg ttgaaggttc tccggatgat   1560
tacaccgata tcaaattcag tgtgaaatgc gccggcatga cggataaaat caaaaaagaa   1620
gtgaccttcg aaaacttcaa agttggtttc agccgcaaaa tgaaaccgaa accggtgcag   1680
gttccgggcg tgtgtggttct ggtggatgat acgtttacca ttaaatctgg cggtagtgcg   1740
tggagccatc cgcagttcga aaaaggcggt ggctctggtg cggttctggg cggtagtgcc   1800
tggagccacc cgcagtttga aaaataataa                                     1830
```

<210> SEQ ID NO 9
<211> LENGTH: 608
<212> TYPE: PRT
<213> ORGANISM: Bacillus subtilis phage phi29

<400> SEQUENCE: 9

```
Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
```

-continued

```
                165                   170                   175
Leu Leu Ile Gln Phe Lys Gln Gly Leu Asp Arg Met Thr Ala Gly Ser
            180                   185               190
Asp Ser Leu Lys Gly Phe Lys Asp Ile Ile Thr Thr Lys Lys Phe Lys
            195                   200               205
Lys Val Phe Pro Thr Leu Ser Leu Gly Leu Asp Lys Glu Val Arg Tyr
    210                   215                   220
Ala Tyr Arg Gly Gly Phe Thr Trp Leu Asn Asp Arg Phe Lys Glu Lys
225                   230                   235                   240
Glu Ile Gly Glu Gly Met Val Phe Asp Val Asn Ser Leu Tyr Pro Ala
                245                   250                   255
Gln Met Tyr Ser Arg Leu Leu Pro Tyr Gly Glu Pro Ile Val Phe Glu
                260                   265               270
Gly Lys Tyr Val Trp Asp Glu Asp Tyr Pro Leu His Ile Gln His Ile
            275                   280               285
Arg Cys Glu Phe Glu Leu Lys Glu Gly Tyr Ile Pro Thr Ile Gln Ile
    290                   295                   300
Lys Arg Ser Arg Phe Tyr Lys Gly Asn Glu Tyr Leu Lys Ser Ser Gly
305                   310                   315                   320
Gly Glu Ile Ala Asp Leu Trp Leu Ser Asn Val Asp Leu Glu Leu Met
                325                   330                   335
Lys Glu His Tyr Asp Leu Tyr Asn Val Glu Tyr Ile Ser Gly Leu Lys
            340                   345               350
Phe Lys Ala Thr Thr Gly Leu Phe Lys Asp Phe Ile Asp Lys Trp Thr
            355                   360               365
Tyr Ile Lys Thr Thr Ser Glu Gly Ala Ile Lys Gln Leu Ala Lys Leu
    370                   375                   380
Met Leu Asn Ser Leu Tyr Gly Lys Phe Ala Ser Asn Pro Asp Val Thr
385                   390                   395                   400
Gly Lys Val Pro Tyr Leu Lys Glu Asn Gly Ala Leu Gly Phe Arg Leu
                405                   410                   415
Gly Glu Glu Glu Thr Lys Asp Pro Val Tyr Thr Pro Met Gly Val Phe
                420                   425               430
Ile Thr Ala Trp Ala Arg Tyr Thr Thr Ile Thr Ala Ala Gln Ala Cys
            435                   440               445
Tyr Asp Arg Ile Ile Tyr Cys Asp Thr Asp Ser Ile His Leu Thr Gly
    450                   455                   460
Thr Glu Ile Pro Asp Val Ile Lys Asp Ile Val Asp Pro Lys Lys Leu
465                   470                   475                   480
Gly Tyr Trp Ala His Glu Ser Thr Phe Lys Arg Ala Lys Tyr Leu Arg
                485                   490               495
Gln Lys Thr Tyr Ile Gln Asp Ile Tyr Met Lys Glu Val Asp Gly Lys
            500                   505               510
Leu Val Glu Gly Ser Pro Asp Asp Tyr Thr Asp Ile Lys Phe Ser Val
            515                   520               525
Lys Cys Ala Gly Met Thr Asp Lys Ile Lys Lys Glu Val Thr Phe Glu
    530                   535                   540
Asn Phe Lys Val Gly Phe Ser Arg Lys Met Lys Pro Lys Pro Val Gln
545                   550                   555                   560
Val Pro Gly Gly Val Val Leu Val Asp Asp Thr Phe Thr Ile Lys Ser
                565                   570                   575
Gly Gly Ser Ala Trp Ser His Pro Gln Phe Glu Lys Gly Gly Gly Ser
            580                   585               590
```

-continued

```
Gly Gly Gly Ser Gly Gly Ser Ala Trp Ser His Pro Gln Phe Glu Lys
        595                 600                 605
```

```
<210> SEQ ID NO 10
<211> LENGTH: 1380
<212> TYPE: DNA
<213> ORGANISM: Escherichia coli

<400> SEQUENCE: 10
atgatgaacg atggcaaaca gcagagcacc ttcctgtttc atgattatga aaccttcggt        60
acccatccgg ccctggatcg tccggcgcag tttgcggcca ttcgcaccga tagcgaattc       120
aatgtgattg gcgaaccgga agtgtttat tgcaaaccgg ccgatgatta tctgccgcag        180
ccgggtgcgg tgctgattac cggtattacc ccgcaggaag cgcgcgcgaa aggtgaaaac       240
gaagcggcgt ttgccgcgcg cattcatagc ctgtttaccg tgccgaaaac ctgcattctg       300
ggctataaca atgtgcgctt cgatgatgaa gttacccgta atatctttta tcgtaacttt       360
tatgatccgt atgcgtggag ctggcagcat gataacagcc gttgggatct gctggatgtg       420
atgcgcgcgt gctatgcgct cgcgcccgaa ggcattaatt ggccggaaaa cgatgatggc       480
ctgccgagct ttcgtctgga acatctgacc aaagccaacg gcattgaaca tagcaatgcc       540
catgatgcga tggccgatgt ttatgcgacc attgcgatgg cgaaactggt taaaacccgt       600
cagccgcgcc tgtttgatta tctgtttacc caccgtaaca aacacaaact gatggcgctg       660
attgatgttc cgcagatgaa accgctggtg catgtgagcg gcatgtttgg cgcctggcgc       720
ggcaacacca ctgggtggc cccgctggcc tggcacccgg aaaatcgtaa cgccgtgatt       780
atggttgatc tggccggtga tattagcccg ctgctggaac tggatagcga taccctgcgt       840
gaacgcctgt ataccgccaa aaccgatctg ggcgataatg ccgccgtgcc ggtgaaactg       900
gttcacatta caaaatgccc ggtgctggcc caggcgaaca ccctgcgccc ggaagatgcg       960
gatcgtctgg gtattaatcg ccagcattgt ctggataatc tgaaaatcct gcgtgaaaac      1020
ccgcaggtgc gtgaaaaagt ggtggcgatc ttcgcggaag cggaaccgtt caccccgagc      1080
gataacgtgg atgcgcagct gtataacggc ttctttagcg atgccgatcg cgcggcgatg      1140
aaaatcgttc tggaaaccga accgcgcaat ctgccggcgc tggatattac ctttgttgat      1200
aaacgtattg aaaaactgct gtttaattat cgtgcgcgca attttccggg taccctggat      1260
tatgccgaac agcagcgttg gctggaacat cgtcgtcagg ttttcacccc ggaatttctg      1320
cagggttatg cggatgaact gcagatgctg gttcagcagt atgccgatga taaagaaaaa      1380
```

```
<210> SEQ ID NO 11
<211> LENGTH: 485
<212> TYPE: PRT
<213> ORGANISM: Escherichia coli

<400> SEQUENCE: 11

Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
```

```
          65                    70                    75                    80

Glu Ala Ala Phe Ala Ala Arg Ile His Ser Leu Phe Thr Val Pro Lys
                85                    90                    95

Thr Cys Ile Leu Gly Tyr Asn Asn Val Arg Phe Asp Asp Glu Val Thr
               100                   105                   110

Arg Asn Ile Phe Tyr Arg Asn Phe Tyr Asp Pro Tyr Ala Trp Ser Trp
           115                   120                   125

Gln His Asp Asn Ser Arg Trp Asp Leu Leu Asp Val Met Arg Ala Cys
       130                   135                   140

Tyr Ala Leu Arg Pro Glu Gly Ile Asn Trp Pro Glu Asn Asp Asp Gly
145                   150                   155                   160

Leu Pro Ser Phe Arg Leu Glu His Leu Thr Lys Ala Asn Gly Ile Glu
                165                   170                   175

His Ser Asn Ala His Asp Ala Met Ala Asp Val Tyr Ala Thr Ile Ala
               180                   185                   190

Met Ala Lys Leu Val Lys Thr Arg Gln Pro Arg Leu Phe Asp Tyr Leu
           195                   200                   205

Phe Thr His Arg Asn Lys His Lys Leu Met Ala Leu Ile Asp Val Pro
       210                   215                   220

Gln Met Lys Pro Leu Val His Val Ser Gly Met Phe Gly Ala Trp Arg
225                   230                   235                   240

Gly Asn Thr Ser Trp Val Ala Pro Leu Ala Trp His Pro Glu Asn Arg
                245                   250                   255

Asn Ala Val Ile Met Val Asp Leu Ala Gly Asp Ile Ser Pro Leu Leu
               260                   265                   270

Glu Leu Asp Ser Asp Thr Leu Arg Glu Arg Leu Tyr Thr Ala Lys Thr
           275                   280                   285

Asp Leu Gly Asp Asn Ala Ala Val Pro Val Lys Leu Val His Ile Asn
       290                   295                   300

Lys Cys Pro Val Leu Ala Gln Ala Asn Thr Leu Arg Pro Glu Asp Ala
305                   310                   315                   320

Asp Arg Leu Gly Ile Asn Arg Gln His Cys Leu Asp Asn Leu Lys Ile
               325                   330                   335

Leu Arg Glu Asn Pro Gln Val Arg Glu Lys Val Val Ala Ile Phe Ala
           340                   345                   350

Glu Ala Glu Pro Phe Thr Pro Ser Asp Asn Val Asp Ala Gln Leu Tyr
           355                   360                   365

Asn Gly Phe Phe Ser Asp Ala Asp Arg Ala Ala Met Lys Ile Val Leu
       370                   375                   380

Glu Thr Glu Pro Arg Asn Leu Pro Ala Leu Asp Ile Thr Phe Val Asp
385                   390                   395                   400

Lys Arg Ile Glu Lys Leu Leu Phe Asn Tyr Arg Ala Arg Asn Phe Pro
               405                   410                   415

Gly Thr Leu Asp Tyr Ala Glu Gln Gln Arg Trp Leu Glu His Arg Arg
           420                   425                   430

Gln Val Phe Thr Pro Glu Phe Leu Gln Gly Tyr Ala Asp Glu Leu Gln
           435                   440                   445

Met Leu Val Gln Gln Tyr Ala Asp Asp Lys Glu Lys Val Ala Leu Leu
       450                   455                   460

Lys Ala Leu Trp Gln Tyr Ala Glu Glu Ile Val Ser Gly Ser Gly His
465                   470                   475                   480

His His His His His
               485
```

```
<210> SEQ ID NO 12
<211> LENGTH: 804
<212> TYPE: DNA
<213> ORGANISM: Escherichia coli

<400> SEQUENCE: 12
atgaaatttg tctcttttaa tatcaacggc ctgcgcgcca gacctcacca gcttgaagcc      60
atcgtcgaaa agcaccaacc ggatgtgatt ggcctgcagg agacaaaagt tcatgacgat     120
atgtttccgc tcgaagaggt ggcgaagctc ggctacaacg tgttttatca cgggcagaaa     180
ggccattatg gcgtggcgct gctgaccaaa gagacgccga ttgccgtgcg tcgcggcttt     240
cccggtgacg acgaagaggc gcagcggcgg attattatgg cggaaatccc ctcactgctg     300
ggtaatgtca ccgtgatcaa cggttacttc ccgcagggtg aaagccgcga ccatccgata     360
aaattcccgg caaaagcgca gttttatcag aatctgcaaa actacctgga aaccgaactc     420
aaacgtgata tccggtact gattatgggc gatatgaata tcagccctac agatctggat     480
atcggcattg cgaagaaaa ccgtaagcgc tggctgcgta ccggtaaatg ctctttcctg     540
ccggaagagc gcgaatggat ggacaggctg atgagctggg ggttggtcga taccttccgc     600
catgcgaatc cgcaaacagc agatcgtttc tcatggtttg attaccgctc aaaaggtttt     660
gacgataacc gtggtctgcg catcgacctg ctgctcgcca gccaaccgct ggcagaatgt     720
tgcgtagaaa ccggcatcga ctatgaaatc cgcagcatgg aaaaaccgtc cgatcacgcc     780
cccgtctggg cgaccttccg ccgc                                           804

<210> SEQ ID NO 13
<211> LENGTH: 268
<212> TYPE: PRT
<213> ORGANISM: Escherichia coli

<400> SEQUENCE: 13

Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
```

```
               180              185              190
Trp Gly Leu Val Asp Thr Phe Arg His Ala Asn Pro Gln Thr Ala Asp
        195              200              205

Arg Phe Ser Trp Phe Asp Tyr Arg Ser Lys Gly Phe Asp Asp Asn Arg
        210              215              220

Gly Leu Arg Ile Asp Leu Leu Leu Ala Ser Gln Pro Leu Ala Glu Cys
225              230              235              240

Cys Val Glu Thr Gly Ile Asp Tyr Glu Ile Arg Ser Met Glu Lys Pro
                245              250              255

Ser Asp His Ala Pro Val Trp Ala Thr Phe Arg Arg
            260              265
```

<210> SEQ ID NO 14
<211> LENGTH: 1275
<212> TYPE: DNA
<213> ORGANISM: Thermus thermophilus

<400> SEQUENCE: 14

```
atgtttcgtc gtaaagaaga tctggatccg ccgctggcac tgctgccgct gaaaggcctg      60
cgcgaagccg ccgcactgct ggaagaagcg ctgcgtcaag gtaaacgcat tcgtgttcac     120
ggcgactatg atgcggatgg cctgaccggc accgcgatcc tggttcgtgg tctggccgcc     180
ctgggtgcgg atgttcatcc gtttatcccg caccgcctgg aagaaggcta tggtgtcctg     240
atggaacgcg tcccggaaca tctggaagcc tcggacctgt ttctgaccgt tgactgcggc     300
attaccaacc atgcggaact gcgcgaactg ctggaaaatg gcgtggaagt cattgttacc     360
gatcatcata cgccgggcaa aacgccgccg ccgggtctgg tcgtgcatcc ggcgctgacg     420
ccggatctga agaaaaaacc gaccggcgca ggcgtggcgt ttctgctgct gtgggcactg     480
catgaacgcc tgggcctgcc gccgccgctg gaatacgcgg acctggcagc cgttggcacc     540
attgccgacg ttgccccgct gtggggttgg aatcgtgcac tggtgaaaga aggtctggca     600
cgcatcccgg cttcatcttg ggtgggcctg cgtctgctgg ctgaagccgt gggctatacc     660
ggcaaagcgg tcgaagtcgc tttccgcatc gcgccgcgca tcaatgcggc ttcccgcctg     720
ggcgaagcgg aaaaagccct cgcgctgctg ctgacggatg atgcggcaga agctcaggcg     780
ctggtcggcg aactgcaccg tctgaacgcc cgtcgtcaga ccctggaaga agcgatgctg     840
cgcaaactgc tgccgcaggc cgacccggaa gcgaaagcca tcgttctgct ggacccggaa     900
ggccatccgg tgttatggg tattgtggcc tctcgcatcc tggaagcgac cctgcgcccg     960
gtctttctgg tggcccaggg caaaggcacc gtgcgttcgc tggctccgat ttccgccgtc    1020
gaagcactgc gcagcgcgga agatctgctg ctgcgttatg tggtcataa agaagcggcg    1080 ggtttcgcaa tggatgaagc gctgtttccg gcgttcaaag cacgcgttga agcgtatgcc    1140
gcacgtttcc cggatccggt tcgtgaagtg gcactgctgg atctgctgcc ggaaccgggc    1200
ctgctgccgc aggtgttccg tgaactggca ctgctggaac cgtatggtga aggtaacccg    1260
gaaccgctgt tcctg                                                      1275
```

<210> SEQ ID NO 15
<211> LENGTH: 425
<212> TYPE: PRT
<213> ORGANISM: Thermus thermophilus

<400> SEQUENCE: 15

```
Met Phe Arg Arg Lys Glu Asp Leu Asp Pro Pro Leu Ala Leu Leu Pro
1               5                   10                  15
```

```
Leu Lys Gly Leu Arg Glu Ala Ala Ala Leu Leu Glu Glu Ala Leu Arg
            20                  25                  30

Gln Gly Lys Arg Ile Arg Val His Gly Asp Tyr Asp Ala Asp Gly Leu
            35                  40                  45

Thr Gly Thr Ala Ile Leu Val Arg Gly Leu Ala Ala Leu Gly Ala Asp
        50                  55                  60

Val His Pro Phe Ile Pro His Arg Leu Glu Glu Gly Tyr Gly Val Leu
65                  70                  75                  80

Met Glu Arg Val Pro Glu His Leu Glu Ala Ser Asp Leu Phe Leu Thr
                85                  90                  95

Val Asp Cys Gly Ile Thr Asn His Ala Glu Leu Arg Glu Leu Leu Glu
            100                 105                 110

Asn Gly Val Glu Val Ile Val Thr Asp His His Thr Pro Gly Lys Thr
            115                 120                 125

Pro Pro Pro Gly Leu Val Val His Pro Ala Leu Thr Pro Asp Leu Lys
        130                 135                 140

Glu Lys Pro Thr Gly Ala Gly Val Ala Phe Leu Leu Leu Trp Ala Leu
145                 150                 155                 160

His Glu Arg Leu Gly Leu Pro Pro Pro Leu Glu Tyr Ala Asp Leu Ala
                165                 170                 175

Ala Val Gly Thr Ile Ala Asp Val Ala Pro Leu Trp Gly Trp Asn Arg
            180                 185                 190

Ala Leu Val Lys Glu Gly Leu Ala Arg Ile Pro Ala Ser Ser Trp Val
            195                 200                 205

Gly Leu Arg Leu Leu Ala Glu Ala Val Gly Tyr Thr Gly Lys Ala Val
        210                 215                 220

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Leu Thr Asp Asp Ala Ala
                245                 250                 255

Glu Ala Gln Ala Leu Val Gly Glu Leu His Arg Leu Asn Ala Arg Arg
            260                 265                 270

Gln Thr Leu Glu Glu Ala Met Leu Arg Lys Leu Leu Pro Gln Ala Asp
            275                 280                 285

Pro Glu Ala Lys Ala Ile Val Leu Leu Asp Pro Glu Gly His Pro Gly
        290                 295                 300

Val Met Gly Ile Val Ala Ser Arg Ile Leu Glu Ala Thr Leu Arg Pro
305                 310                 315                 320

Val Phe Leu Val Ala Gln Gly Lys Gly Thr Val Arg Ser Leu Ala Pro
                325                 330                 335

Ile Ser Ala Val Glu Ala Leu Arg Ser Ala Glu Asp Leu Leu Leu Arg
            340                 345                 350

Tyr Gly Gly His Lys Glu Ala Ala Gly Phe Ala Met Asp Glu Ala Leu
            355                 360                 365

Phe Pro Ala Phe Lys Ala Arg Val Glu Ala Tyr Ala Ala Arg Phe Pro
        370                 375                 380

Asp Pro Val Arg Glu Val Ala Leu Leu Asp Leu Leu Pro Glu Pro Gly
385                 390                 395                 400

Leu Leu Pro Gln Val Phe Arg Glu Leu Ala Leu Leu Glu Pro Tyr Gly
                405                 410                 415

Glu Gly Asn Pro Glu Pro Leu Phe Leu
            420                 425
```

<210> SEQ ID NO 16
<211> LENGTH: 738
<212> TYPE: DNA
<213> ORGANISM: Bacteriophage lambda

<400> SEQUENCE: 16
tccggaagcg gctctggtag tggttctggc atgacaccgg acattatcct gcagcgtacc      60
gggatcgatg tgagagctgt cgaacagggg gatgatgcgt ggcacaaatt acggctcggc     120
gtcatcaccg cttcagaagt tcacaacgtg atagcaaaac cccgctccgg aaagaagtgg     180
cctgacatga aaatgtccta cttccacacc ctgcttgctg aggtttgcac cggtgtggct     240
ccggaagtta acgctaaagc actggcctgg ggaaaacagt acgagaacga cgccagaacc     300
ctgtttgaat tcacttccgg cgtgaatgtt actgaatccc cgatcatcta tcgcgacgaa     360
agtatgcgta ccgcctgctc tcccgatggt ttatgcagtg acggcaacgg ccttgaactg     420
aaatgcccgt ttacctcccg ggatttcatg aagttccggc tcggtggttt cgaggccata     480
aagtcagctt acatggccca ggtgcagtac agcatgtggg tgacgcgaaa aaatgcctgg     540
tactttgcca actatgaccc gcgtatgaag cgtgaaggcc tgcattatgt cgtgattgag     600
cgggatgaaa agtacatggc gagttttgac gagatcgtgc cggagttcat cgaaaaaatg     660
gacgaggcac tggctgaaat tggttttgta tttggggagc aatggcgatc tggctctggt     720
tccggcagcg gttccgga                                                    738

<210> SEQ ID NO 17
<211> LENGTH: 226
<212> TYPE: PRT
<213> ORGANISM: Bacteriophage lambda

<400> SEQUENCE: 17

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
                20                  25                  30

Thr Ala Ser Glu Val His Asn Val Ile Ala Lys Pro Arg Ser Gly Lys
            35                  40                  45

Lys Trp Pro Asp Met Lys Met Ser Tyr Phe His Thr Leu Leu Ala Glu
        50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
                100                 105                 110

Arg Thr Ala Cys Ser Pro Asp Gly Leu Cys Ser Asp Gly Asn Gly Leu
            115                 120                 125

Glu Leu Lys Cys Pro Phe Thr Ser Arg Asp Phe Met Lys Phe Arg Leu
        130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu

-continued

```
            195                 200                 205

Lys Met Asp Glu Ala Leu Ala Glu Ile Gly Phe Val Phe Gly Glu Gln
    210                 215                 220

Trp Arg
225

<210> SEQ ID NO 18
<211> LENGTH: 760
<212> TYPE: PRT
<213> ORGANISM: Methanococcoides burtonii

<400> SEQUENCE: 18

Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
            20                  25                  30

Glu Met Gly Leu Leu Glu Lys Lys Asn Leu Leu Ala Ala Ile Pro Thr
        35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
            100                 105                 110

Val Asn Asp Ile Ile Val Ala Thr Ser Glu Lys Thr Asp Ser Leu Leu
            115                 120                 125

Arg Asn Gly Thr Ser Trp Met Asp Glu Ile Thr Thr Val Val Val Asp
    130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
            180                 185                 190

Ala Ala Leu Val Leu Ser Glu Trp Arg Pro Thr Asp Leu His Glu Gly
            195                 200                 205

Val Leu Phe Gly Asp Ala Ile Asn Phe Pro Gly Ser Gln Lys Lys Ile
    210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser
            275                 280                 285

Thr Gly Glu Thr Asp Thr Ala Ile Val Leu Ala Asn Cys Ile Arg Lys
    290                 295                 300

Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335
```

-continued

```
Pro Thr Leu Ala Ala Gly Leu Asn Leu Pro Ala Arg Arg Val Ile Ile
        340             345             350

Arg Ser Tyr Arg Arg Phe Asp Ser Asn Phe Gly Met Gln Pro Ile Pro
        355             360             365

Val Leu Glu Tyr Lys Gln Met Ala Gly Arg Ala Gly Arg Pro His Leu
        370             375             380

Asp Pro Tyr Gly Glu Ser Val Leu Leu Ala Lys Thr Tyr Asp Glu Phe
385             390             395             400

Ala Gln Leu Met Glu Asn Tyr Val Glu Ala Asp Ala Glu Asp Ile Trp
                405             410             415

Ser Lys Leu Gly Thr Glu Asn Ala Leu Arg Thr His Val Leu Ser Thr
        420             425             430

Ile Val Asn Gly Phe Ala Ser Thr Arg Gln Glu Leu Phe Asp Phe Phe
        435             440             445

Gly Ala Thr Phe Phe Ala Tyr Gln Gln Asp Lys Trp Met Leu Glu Glu
        450             455             460

Val Ile Asn Asp Cys Leu Glu Phe Leu Ile Asp Lys Ala Met Val Ser
465             470             475             480

Glu Thr Glu Asp Ile Glu Asp Ala Ser Lys Leu Phe Leu Arg Gly Thr
                485             490             495

Arg Leu Gly Ser Leu Val Ser Met Leu Tyr Ile Asp Pro Leu Ser Gly
        500             505             510

Ser Lys Ile Val Asp Gly Phe Lys Asp Ile Gly Lys Ser Thr Gly Gly
        515             520             525

Asn Met Gly Ser Leu Glu Asp Asp Lys Gly Asp Asp Ile Thr Val Thr
        530             535             540

Asp Met Thr Leu Leu His Leu Val Cys Ser Thr Pro Asp Met Arg Gln
545             550             555             560

Leu Tyr Leu Arg Asn Thr Asp Tyr Thr Ile Val Asn Glu Tyr Ile Val
                565             570             575

Ala His Ser Asp Glu Phe His Glu Ile Pro Asp Lys Leu Lys Glu Thr
        580             585             590

Asp Tyr Glu Trp Phe Met Gly Glu Val Lys Thr Ala Met Leu Leu Glu
        595             600             605

Glu Trp Val Thr Glu Val Ser Ala Glu Asp Ile Thr Arg His Phe Asn
        610             615             620

Val Gly Glu Gly Asp Ile His Ala Leu Ala Asp Thr Ser Glu Trp Leu
625             630             635             640

Met His Ala Ala Ala Lys Leu Ala Glu Leu Leu Gly Val Glu Tyr Ser
                645             650             655

Ser His Ala Tyr Ser Leu Glu Lys Arg Ile Arg Tyr Gly Ser Gly Leu
        660             665             670

Asp Leu Met Glu Leu Val Gly Ile Arg Gly Val Gly Arg Val Arg Ala
        675             680             685

Arg Lys Leu Tyr Asn Ala Gly Phe Val Ser Val Ala Lys Leu Lys Gly
        690             695             700

Ala Asp Ile Ser Val Leu Ser Lys Leu Val Gly Pro Lys Val Ala Tyr
705             710             715             720

Asn Ile Leu Ser Gly Ile Gly Val Arg Val Asn Asp Lys His Phe Asn
                725             730             735

Ser Ala Pro Ile Ser Ser Asn Thr Leu Asp Thr Leu Leu Asp Lys Asn
        740             745             750

Gln Lys Thr Phe Asn Asp Phe Gln
```

-continued

```
          755                  760
```

<210> SEQ ID NO 19
<211> LENGTH: 707
<212> TYPE: PRT
<213> ORGANISM: Cenarchaeum symbiosum

<400> SEQUENCE: 19

```
Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
                20                  25                  30

Lys Ala Gly Leu Thr Asp Gly Lys Ser Val Leu Val Ser Ala Pro Thr
            35                  40                  45

Ala Ser Gly Lys Thr Leu Ile Ala Ala Ile Ala Met Ile Ser His Leu
        50                  55                  60

Ser Arg Asn Arg Gly Lys Ala Val Tyr Leu Ser Pro Leu Arg Ala Leu
65                  70                  75                  80

Ala Ala Glu Lys Phe Ala Glu Phe Gly Lys Ile Gly Gly Ile Pro Leu
                85                  90                  95

Gly Arg Pro Val Arg Val Gly Val Ser Thr Gly Asp Phe Glu Lys Ala
                100                 105                 110

Gly Arg Ser Leu Gly Asn Asn Asp Ile Leu Val Leu Thr Asn Glu Arg
            115                 120                 125

Met Asp Ser Leu Ile Arg Arg Arg Pro Asp Trp Met Asp Glu Val Gly
        130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
                180                 185                 190

Ala Gly Trp Leu Asp Cys Thr Leu Val His Ser Thr Trp Arg Pro Val
            195                 200                 205

Pro Leu Ser Glu Gly Val Tyr Gln Asp Gly Glu Val Ala Met Gly Asp
        210                 215                 220

Gly Ser Arg His Glu Val Ala Ala Thr Gly Gly Gly Pro Ala Val Asp
225                 230                 235                 240

Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
                260                 265                 270

Ile Pro Glu Ala Lys Gly Ala Asp Ala Ala Lys Leu Ala Ala Ala Ala
            275                 280                 285

Lys Lys Ile Ile Ser Ser Gly Gly Glu Thr Lys Leu Ala Lys Thr Leu
        290                 295                 300

Ala Glu Leu Val Glu Lys Gly Ala Ala Phe His His Ala Gly Leu Asn
305                 310                 315                 320

Gln Asp Cys Arg Ser Val Val Glu Glu Glu Phe Arg Ser Gly Arg Ile
                325                 330                 335

Arg Leu Leu Ala Ser Thr Pro Thr Leu Ala Ala Gly Val Asn Leu Pro
            340                 345                 350

Ala Arg Arg Val Val Ile Ser Ser Val Met Arg Tyr Asn Ser Ser Ser
            355                 360                 365
```

-continued

```
Gly Met Ser Glu Pro Ile Ser Ile Leu Glu Tyr Lys Gln Leu Cys Gly
    370             375             380

Arg Ala Gly Arg Pro Gln Tyr Asp Lys Ser Gly Glu Ala Ile Val Val
385             390             395             400

Gly Gly Val Asn Ala Asp Glu Ile Phe Asp Arg Tyr Ile Gly Gly Glu
            405             410             415

Pro Glu Pro Ile Arg Ser Ala Met Val Asp Asp Arg Ala Leu Arg Ile
            420             425             430

His Val Leu Ser Leu Val Thr Thr Ser Pro Gly Ile Lys Glu Asp Asp
        435             440             445

Val Thr Glu Phe Phe Leu Gly Thr Leu Gly Gly Gln Gln Ser Gly Glu
    450             455             460

Ser Thr Val Lys Phe Ser Val Ala Val Ala Leu Arg Phe Leu Gln Glu
465             470             475             480

Glu Gly Met Leu Gly Arg Arg Gly Gly Arg Leu Ala Ala Thr Lys Met
            485             490             495

Gly Arg Leu Val Ser Arg Leu Tyr Met Asp Pro Met Thr Ala Val Thr
            500             505             510

Leu Arg Asp Ala Val Gly Glu Ala Ser Pro Gly Arg Met His Thr Leu
        515             520             525

Gly Phe Leu His Leu Val Ser Glu Cys Ser Glu Phe Met Pro Arg Phe
    530             535             540

Ala Leu Arg Gln Lys Asp His Glu Val Ala Glu Met Met Leu Glu Ala
545             550             555             560

Gly Arg Gly Glu Leu Leu Arg Pro Val Tyr Ser Tyr Glu Cys Gly Arg
            565             570             575

Gly Leu Leu Ala Leu His Arg Trp Ile Gly Glu Ser Pro Glu Ala Lys
            580             585             590

Leu Ala Glu Asp Leu Lys Phe Glu Ser Gly Asp Val His Arg Met Val
        595             600             605

Glu Ser Ser Gly Trp Leu Leu Arg Cys Ile Trp Glu Ile Ser Lys His
    610             615             620

Gln Glu Arg Pro Asp Leu Leu Gly Glu Leu Asp Val Leu Arg Ser Arg
625             630             635             640

Val Ala Tyr Gly Ile Lys Ala Glu Leu Val Pro Leu Val Ser Ile Lys
            645             650             655

Gly Ile Gly Arg Val Arg Ser Arg Arg Leu Phe Arg Gly Gly Ile Lys
            660             665             670

Gly Pro Gly Asp Leu Ala Ala Val Pro Val Glu Arg Leu Ser Arg Val
            675             680             685

Glu Gly Ile Gly Ala Thr Leu Ala Asn Asn Ile Lys Ser Gln Leu Arg
    690             695             700

Lys Gly Gly
705
```

<210> SEQ ID NO 20
<211> LENGTH: 720
<212> TYPE: PRT
<213> ORGANISM: Thermococcus gammatolerans

<400> SEQUENCE: 20

```
Met Lys Val Asp Glu Leu Pro Val Asp Glu Arg Leu Lys Ala Val Leu
1               5               10              15

Lys Glu Arg Gly Ile Glu Glu Leu Tyr Pro Pro Gln Ala Glu Ala Leu
            20              25              30
```

-continued

```
Lys Ser Gly Ala Leu Glu Gly Arg Asn Leu Val Leu Ala Ile Pro Thr
        35                  40                  45

Ala Ser Gly Lys Thr Leu Val Ser Glu Ile Val Met Val Asn Lys Leu
        50                  55                  60

Ile Gln Glu Gly Gly Lys Ala Val Tyr Leu Val Pro Leu Lys Ala Leu
65                  70                  75                  80

Ala Glu Glu Lys Tyr Arg Glu Phe Lys Glu Trp Glu Lys Leu Gly Leu
                85                  90                  95

Lys Val Ala Ala Thr Thr Gly Asp Tyr Asp Ser Thr Asp Asp Trp Leu
                100                 105                 110

Gly Arg Tyr Asp Ile Ile Val Ala Thr Ala Glu Lys Phe Asp Ser Leu
                115                 120                 125

Leu Arg His Gly Ala Arg Trp Ile Asn Asp Val Lys Leu Val Val Ala
        130                 135                 140

Asp Glu Val His Leu Ile Gly Ser Tyr Asp Arg Gly Ala Thr Leu Glu
145                 150                 155                 160

Met Ile Leu Thr His Met Leu Gly Arg Ala Gln Ile Leu Ala Leu Ser
                165                 170                 175

Ala Thr Val Gly Asn Ala Glu Glu Leu Ala Glu Trp Leu Asp Ala Ser
                180                 185                 190

Leu Val Val Ser Asp Trp Arg Pro Val Gln Leu Arg Arg Gly Val Phe
                195                 200                 205

His Leu Gly Thr Leu Ile Trp Glu Asp Gly Lys Val Glu Ser Tyr Pro
        210                 215                 220

Glu Asn Trp Tyr Ser Leu Val Val Asp Ala Val Lys Arg Gly Lys Gly
225                 230                 235                 240

Ala Leu Val Phe Val Asn Thr Arg Arg Ser Ala Glu Lys Glu Ala Leu
                245                 250                 255

Ala Leu Ser Lys Leu Val Ser Ser His Leu Thr Lys Pro Glu Lys Arg
                260                 265                 270

Ala Leu Glu Ser Leu Ala Ser Gln Leu Glu Asp Asn Pro Thr Ser Glu
        275                 280                 285

Lys Leu Lys Arg Ala Leu Arg Gly Gly Val Ala Phe His His Ala Gly
        290                 295                 300

Leu Ser Arg Val Glu Arg Thr Leu Ile Glu Asp Ala Phe Arg Glu Gly
305                 310                 315                 320

Leu Ile Lys Val Ile Thr Ala Thr Pro Thr Leu Ser Ala Gly Val Asn
                325                 330                 335

Leu Pro Ser Phe Arg Val Ile Ile Arg Asp Thr Lys Arg Tyr Ala Gly
                340                 345                 350

Phe Gly Trp Thr Asp Ile Pro Val Leu Glu Ile Gln Gln Met Met Gly
        355                 360                 365

Arg Ala Gly Arg Pro Arg Tyr Asp Lys Tyr Gly Glu Ala Ile Ile Val
        370                 375                 380

Ala Arg Thr Asp Glu Pro Gly Lys Leu Met Glu Arg Tyr Ile Arg Gly
385                 390                 395                 400

Lys Pro Glu Lys Leu Phe Ser Met Leu Ala Asn Glu Gln Ala Phe Arg
                405                 410                 415

Ser Gln Val Leu Ala Leu Ile Thr Asn Phe Gly Ile Arg Ser Phe Pro
                420                 425                 430

Glu Leu Val Arg Phe Leu Glu Arg Thr Phe Tyr Ala His Gln Arg Lys
        435                 440                 445
```

```
Asp Leu Ser Ser Leu Glu Tyr Lys Ala Lys Glu Val Val Tyr Phe Leu
    450                 455                 460

Ile Glu Asn Glu Phe Ile Asp Leu Asp Leu Glu Asp Arg Phe Ile Pro
465                 470                 475                 480

Leu Pro Phe Gly Lys Arg Thr Ser Gln Leu Tyr Ile Asp Pro Leu Thr
                485                 490                 495

Ala Lys Lys Phe Lys Asp Ala Phe Pro Ala Ile Glu Arg Asn Pro Asn
                500                 505                 510

Pro Phe Gly Ile Phe Gln Leu Ile Ala Ser Thr Pro Asp Met Ala Thr
                515                 520                 525

Leu Thr Ala Arg Arg Arg Glu Met Glu Asp Tyr Leu Asp Leu Ala Tyr
    530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                565                 570                 575

Asp Trp Ile Asn Glu Val Pro Glu Ala Arg Ile Tyr Glu Thr Tyr Ser
                580                 585                 590

Ile Asp Pro Gly Asp Leu Tyr Arg Leu Leu Glu Leu Ala Asp Trp Leu
                595                 600                 605

Met Tyr Ser Leu Ile Glu Leu Tyr Lys Leu Phe Glu Pro Lys Glu Glu
    610                 615                 620

Ile Leu Asn Tyr Leu Arg Asp Leu His Leu Arg Leu Arg His Gly Val
625                 630                 635                 640

Arg Glu Glu Leu Leu Glu Leu Val Arg Leu Pro Asn Ile Gly Arg Lys
                645                 650                 655

Arg Ala Arg Ala Leu Tyr Asn Ala Gly Phe Arg Ser Val Glu Ala Ile
                660                 665                 670

Ala Asn Ala Lys Pro Ala Glu Leu Leu Ala Val Glu Gly Ile Gly Ala
                675                 680                 685

Lys Ile Leu Asp Gly Ile Tyr Arg His Leu Gly Ile Glu Lys Arg Val
    690                 695                 700

Thr Glu Glu Lys Pro Lys Arg Lys Gly Thr Leu Glu Asp Phe Leu Arg
705                 710                 715                 720

<210> SEQ ID NO 21
<211> LENGTH: 799
<212> TYPE: PRT
<213> ORGANISM: Methanospirillum hungatei

<400> SEQUENCE: 21

Met Glu Ile Ala Ser Leu Pro Leu Pro Asp Ser Phe Ile Arg Ala Cys
1               5                   10                  15

His Ala Lys Gly Ile Arg Ser Leu Tyr Pro Pro Gln Ala Glu Cys Ile
                20                  25                  30

Glu Lys Gly Leu Leu Glu Gly Lys Asn Leu Leu Ile Ser Ile Pro Thr
                35                  40                  45

Ala Ser Gly Lys Thr Leu Leu Ala Glu Met Ala Met Trp Ser Arg Ile
    50                  55                  60

Ala Ala Gly Gly Lys Cys Leu Tyr Ile Val Pro Leu Arg Ala Leu Ala
65                  70                  75                  80

Ser Glu Lys Tyr Asp Glu Phe Ser Lys Lys Gly Val Ile Arg Val Gly
                85                  90                  95

Ile Ala Thr Gly Asp Leu Asp Arg Thr Asp Ala Tyr Leu Gly Glu Asn
                100                 105                 110
```

-continued

```
Asp Ile Ile Val Ala Thr Ser Glu Lys Thr Asp Ser Leu Leu Arg Asn
        115                 120                 125

Arg Thr Pro Trp Leu Ser Gln Ile Thr Cys Ile Val Leu Asp Glu Val
    130                 135                 140

His Leu Ile Gly Ser Glu Asn Arg Gly Ala Thr Leu Glu Met Val Ile
145                 150                 155                 160

Thr Lys Leu Arg Tyr Thr Asn Pro Val Met Gln Ile Ile Gly Leu Ser
                165                 170                 175

Ala Thr Ile Gly Asn Pro Ala Gln Leu Ala Glu Trp Leu Asp Ala Thr
            180                 185                 190

Leu Ile Thr Ser Thr Trp Arg Pro Val Asp Leu Arg Gln Gly Val Tyr
            195                 200                 205

Tyr Asn Gly Lys Ile Arg Phe Ser Asp Ser Glu Arg Pro Ile Gln Gly
    210                 215                 220

Lys Thr Lys His Asp Asp Leu Asn Leu Cys Leu Asp Thr Ile Glu Glu
225                 230                 235                 240

Gly Gly Gln Cys Leu Val Phe Val Ser Ser Arg Arg Asn Ala Glu Gly
            245                 250                 255

Phe Ala Lys Lys Ala Ala Gly Ala Leu Lys Ala Gly Ser Pro Asp Ser
            260                 265                 270

Lys Ala Leu Ala Gln Glu Leu Arg Arg Leu Arg Asp Arg Asp Glu Gly
    275                 280                 285

Asn Val Leu Ala Asp Cys Val Glu Arg Gly Ala Ala Phe His His Ala
    290                 295                 300

Gly Leu Ile Arg Gln Glu Arg Thr Ile Ile Glu Glu Gly Phe Arg Asn
305                 310                 315                 320

Gly Tyr Ile Glu Val Ile Ala Ala Thr Pro Thr Leu Ala Ala Gly Leu
                325                 330                 335

Asn Leu Pro Ala Arg Arg Val Ile Ile Arg Asp Tyr Asn Arg Phe Ala
            340                 345                 350

Ser Gly Leu Gly Met Val Pro Ile Pro Val Gly Glu Tyr His Gln Met
            355                 360                 365

Ala Gly Arg Ala Gly Arg Pro His Leu Asp Pro Tyr Gly Glu Ala Val
    370                 375                 380

Leu Leu Ala Lys Asp Ala Pro Ser Val Glu Arg Leu Phe Glu Thr Phe
385                 390                 395                 400

Ile Asp Ala Glu Ala Glu Arg Val Asp Ser Gln Cys Val Asp Asp Ala
                405                 410                 415

Ser Leu Cys Ala His Ile Leu Ser Leu Ile Ala Thr Gly Phe Ala His
            420                 425                 430

Asp Gln Glu Ala Leu Ser Ser Phe Met Glu Arg Thr Phe Tyr Phe Phe
    435                 440                 445

Gln His Pro Lys Thr Arg Ser Leu Pro Arg Leu Val Ala Asp Ala Ile
    450                 455                 460

Arg Phe Leu Thr Thr Ala Gly Met Val Glu Glu Arg Glu Asn Thr Leu
465                 470                 475                 480

Ser Ala Thr Arg Leu Gly Ser Leu Val Ser Arg Leu Tyr Leu Asn Pro
            485                 490                 495

Cys Thr Ala Arg Leu Ile Leu Asp Ser Leu Lys Ser Cys Lys Thr Pro
            500                 505                 510

Thr Leu Ile Gly Leu Leu His Val Ile Cys Val Ser Pro Asp Met Gln
            515                 520                 525
```

-continued

```
Arg Leu Tyr Leu Lys Ala Ala Asp Thr Gln Leu Leu Arg Thr Phe Leu
    530                 535                 540

Phe Lys His Lys Asp Asp Leu Ile Leu Pro Leu Pro Phe Glu Gln Glu
545                 550                 555                 560

Glu Glu Glu Leu Trp Leu Ser Gly Leu Lys Thr Ala Leu Val Leu Thr
                565                 570                 575

Asp Trp Ala Asp Glu Phe Ser Glu Gly Met Ile Glu Glu Arg Tyr Gly
                580                 585                 590

Ile Gly Ala Gly Asp Leu Tyr Asn Ile Val Asp Ser Gly Lys Trp Leu
                595                 600                 605

Leu His Gly Thr Glu Arg Leu Val Ser Val Glu Met Pro Glu Met Ser
    610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
                645                 650                 655

Arg Thr Leu Tyr Asn Ala Gly Tyr Pro Asp Pro Glu Ala Val Ala Arg
                660                 665                 670

Ala Gly Leu Ser Thr Ile Ala Arg Ile Ile Gly Glu Gly Ile Ala Arg
                675                 680                 685

Gln Val Ile Asp Glu Ile Thr Gly Val Lys Arg Ser Gly Ile His Ser
    690                 695                 700

Ser Asp Asp Asp Tyr Gln Gln Lys Thr Pro Glu Leu Leu Thr Asp Ile
705                 710                 715                 720

Pro Gly Ile Gly Lys Lys Met Ala Glu Lys Leu Gln Asn Ala Gly Ile
                725                 730                 735

Ile Thr Val Ser Asp Leu Leu Thr Ala Asp Glu Val Leu Leu Ser Asp
                740                 745                 750

Val Leu Gly Ala Ala Arg Ala Arg Lys Val Leu Ala Phe Leu Ser Asn
                755                 760                 765

Ser Glu Lys Glu Asn Ser Ser Ser Asp Lys Thr Glu Glu Ile Pro Asp
    770                 775                 780

Thr Gln Lys Ile Arg Gly Gln Ser Ser Trp Glu Asp Phe Gly Cys
785                 790                 795
```

<210> SEQ ID NO 22
<211> LENGTH: 1756
<212> TYPE: PRT
<213> ORGANISM: Escherichia coli

<400> SEQUENCE: 22

```
Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
                20                  25                  30

Trp Ala Gly Lys Gly Ala Glu Gln Leu Gly Leu Gln Gly Ser Val Asp
            35                  40                  45

Lys Asp Val Phe Thr Arg Leu Leu Glu Gly Arg Leu Pro Asp Gly Ala
    50                  55                  60

Asp Leu Ser Arg Met Gln Asp Gly Ser Asn Lys His Arg Pro Gly Tyr
65                  70                  75                  80

Asp Leu Thr Phe Ser Ala Pro Lys Ser Val Ser Met Met Ala Met Leu
                85                  90                  95

Gly Gly Asp Lys Arg Leu Ile Asp Ala His Asn Gln Ala Val Asp Phe
                100                 105                 110
```

```
Ala Val Arg Gln Val Glu Ala Leu Ala Ser Thr Arg Val Met Thr Asp
        115             120             125

Gly Gln Ser Glu Thr Val Leu Thr Gly Asn Leu Val Met Ala Leu Phe
    130             135             140

Asn His Asp Thr Ser Arg Asp Gln Glu Pro Gln Leu His Thr His Ala
145             150             155             160

Val Val Ala Asn Val Thr Gln His Asn Gly Glu Trp Lys Thr Leu Ser
            165             170             175

Ser Asp Lys Val Gly Lys Thr Gly Phe Ile Glu Asn Val Tyr Ala Asn
            180             185             190

Gln Ile Ala Phe Gly Arg Leu Tyr Arg Glu Lys Leu Lys Glu Gln Val
            195             200             205

Glu Ala Leu Gly Tyr Glu Thr Glu Val Val Gly Lys His Gly Met Trp
    210             215             220

Glu Met Pro Gly Val Pro Val Glu Ala Phe Ser Gly Arg Ser Gln Ala
225             230             235             240

Ile Arg Glu Ala Val Gly Glu Asp Ala Ser Leu Lys Ser Arg Asp Val
            245             250             255

Ala Ala Leu Asp Thr Arg Lys Ser Lys Gln His Val Asp Pro Glu Ile
            260             265             270

Arg Met Ala Glu Trp Met Gln Thr Leu Lys Glu Thr Gly Phe Asp Ile
            275             280             285

Arg Ala Tyr Arg Asp Ala Ala Asp Gln Arg Thr Glu Ile Arg Thr Gln
    290             295             300

Ala Pro Gly Pro Ala Ser Gln Asp Gly Pro Asp Val Gln Gln Ala Val
305             310             315             320

Thr Gln Ala Ile Ala Gly Leu Ser Glu Arg Lys Val Gln Phe Thr Tyr
            325             330             335

Thr Asp Val Leu Ala Arg Thr Val Gly Ile Leu Pro Pro Glu Asn Gly
            340             345             350

Val Ile Glu Arg Ala Arg Ala Gly Ile Asp Glu Ala Ile Ser Arg Glu
            355             360             365

Gln Leu Ile Pro Leu Asp Arg Glu Lys Gly Leu Phe Thr Ser Gly Ile
    370             375             380

His Val Leu Asp Glu Leu Ser Val Arg Ala Leu Ser Arg Asp Ile Met
385             390             395             400

Lys Gln Asn Arg Val Thr Val His Pro Glu Lys Ser Val Pro Arg Thr
            405             410             415

Ala Gly Tyr Ser Asp Ala Val Ser Val Leu Ala Gln Asp Arg Pro Ser
            420             425             430

Leu Ala Ile Val Ser Gly Gln Gly Gly Ala Ala Gly Gln Arg Glu Arg
            435             440             445

Val Ala Glu Leu Val Met Met Ala Arg Glu Gln Gly Arg Glu Val Gln
    450             455             460

Ile Ile Ala Ala Asp Arg Arg Ser Gln Met Asn Leu Lys Gln Asp Glu
465             470             475             480

Arg Leu Ser Gly Glu Leu Ile Thr Gly Arg Arg Gln Leu Leu Glu Gly
            485             490             495

Met Ala Phe Thr Pro Gly Ser Thr Val Ile Val Asp Gln Gly Glu Lys
            500             505             510

Leu Ser Leu Lys Glu Thr Leu Thr Leu Leu Asp Gly Ala Ala Arg His
            515             520             525
```

-continued

```
Asn Val Gln Val Leu Ile Thr Asp Ser Gly Gln Arg Thr Gly Thr Gly
    530                 535                 540

Ser Ala Leu Met Ala Met Lys Asp Ala Gly Val Asn Thr Tyr Arg Trp
545                 550                 555                 560

Gln Gly Gly Glu Gln Arg Pro Ala Thr Ile Ile Ser Glu Pro Asp Arg
                565                 570                 575

Asn Val Arg Tyr Ala Arg Leu Ala Gly Asp Phe Ala Ala Ser Val Lys
                580                 585                 590

Ala Gly Glu Glu Ser Val Ala Gln Val Ser Gly Val Arg Glu Gln Ala
                595                 600                 605

Ile Leu Thr Gln Ala Ile Arg Ser Glu Leu Lys Thr Gln Gly Val Leu
    610                 615                 620

Gly His Pro Glu Val Thr Met Thr Ala Leu Ser Pro Val Trp Leu Asp
625                 630                 635                 640

Ser Arg Ser Arg Tyr Leu Arg Asp Met Tyr Arg Pro Gly Met Val Met
                645                 650                 655

Glu Gln Trp Asn Pro Glu Thr Arg Ser His Asp Arg Tyr Val Ile Asp
                660                 665                 670

Arg Val Thr Ala Gln Ser His Ser Leu Thr Leu Arg Asp Ala Gln Gly
                675                 680                 685

Glu Thr Gln Val Val Arg Ile Ser Ser Leu Asp Ser Ser Trp Ser Leu
    690                 695                 700

Phe Arg Pro Glu Lys Met Pro Val Ala Asp Gly Glu Arg Leu Arg Val
705                 710                 715                 720

Thr Gly Lys Ile Pro Gly Leu Arg Val Ser Gly Gly Asp Arg Leu Gln
                725                 730                 735

Val Ala Ser Val Ser Glu Asp Ala Met Thr Val Val Val Pro Gly Arg
                740                 745                 750

Ala Glu Pro Ala Ser Leu Pro Val Ser Asp Ser Pro Phe Thr Ala Leu
                755                 760                 765

Lys Leu Glu Asn Gly Trp Val Glu Thr Pro Gly His Ser Val Ser Asp
    770                 775                 780

Ser Ala Thr Val Phe Ala Ser Val Thr Gln Met Ala Met Asp Asn Ala
785                 790                 795                 800

Thr Leu Asn Gly Leu Ala Arg Ser Gly Arg Asp Val Arg Leu Tyr Ser
                805                 810                 815

Ser Leu Asp Glu Thr Arg Thr Ala Glu Lys Leu Ala Arg His Pro Ser
                820                 825                 830

Phe Thr Val Val Ser Glu Gln Ile Lys Ala Arg Ala Gly Glu Thr Leu
                835                 840                 845

Leu Glu Thr Ala Ile Ser Leu Gln Lys Ala Gly Leu His Thr Pro Ala
    850                 855                 860

Gln Gln Ala Ile His Leu Ala Leu Pro Val Leu Glu Ser Lys Asn Leu
865                 870                 875                 880

Ala Phe Ser Met Val Asp Leu Leu Thr Glu Ala Lys Ser Phe Ala Ala
                885                 890                 895

Glu Gly Thr Gly Phe Thr Glu Leu Gly Gly Glu Ile Asn Ala Gln Ile
                900                 905                 910

Lys Arg Gly Asp Leu Leu Tyr Val Asp Val Ala Lys Gly Tyr Gly Thr
                915                 920                 925

Gly Leu Leu Val Ser Arg Ala Ser Tyr Glu Ala Glu Lys Ser Ile Leu
    930                 935                 940

Arg His Ile Leu Glu Gly Lys Glu Ala Val Thr Pro Leu Met Glu Arg
```

-continued

```
945                   950                   955                   960
Val Pro Gly Glu Leu Met Glu Thr Leu Thr Ser Gly Gln Arg Ala Ala
                965                   970                   975
Thr Arg Met Ile Leu Glu Thr Ser Asp Arg Phe Thr Val Val Gln Gly
            980                   985                   990
Tyr Ala Gly Val Gly Lys Thr Thr  Gln Phe Arg Ala Val  Met Ser Ala
        995                   1000                  1005
Val Asn  Met Leu Pro Ala Ser  Glu Arg Pro Arg Val  Val Gly Leu
    1010                  1015                  1020
Gly Pro  Thr His Arg Ala Val  Gly Glu Met Arg Ser  Ala Gly Val
    1025                  1030                  1035
Asp Ala  Gln Thr Leu Ala Ser  Phe Leu His Asp Thr  Gln Leu Gln
    1040                  1045                  1050
Gln Arg  Ser Gly Glu Thr Pro  Asp Phe Ser Asn Thr  Leu Phe Leu
    1055                  1060                  1065
Leu Asp  Glu Ser Ser Met Val  Gly Asn Thr Glu Met  Ala Arg Ala
    1070                  1075                  1080
Tyr Ala  Leu Ile Ala Ala Gly  Gly Gly Arg Ala Val  Ala Ser Gly
    1085                  1090                  1095
Asp Thr  Asp Gln Leu Gln Ala  Ile Ala Pro Gly Gln  Ser Phe Arg
    1100                  1105                  1110
Leu Gln  Gln Thr Arg Ser Ala  Ala Asp Val Val Ile  Met Lys Glu
    1115                  1120                  1125
Ile Val  Arg Gln Thr Pro Glu  Leu Arg Glu Ala Val  Tyr Ser Leu
    1130                  1135                  1140
Ile Asn  Arg Asp Val Glu Arg  Ala Leu Ser Gly Leu  Glu Ser Val
    1145                  1150                  1155
Lys Pro  Ser Gln Val Pro Arg  Leu Glu Gly Ala Trp  Ala Pro Glu
    1160                  1165                  1170
His Ser  Val Thr Glu Phe Ser  His Ser Gln Glu Ala  Lys Leu Ala
    1175                  1180                  1185
Glu Ala  Gln Gln Lys Ala Met  Leu Lys Gly Glu Ala  Phe Pro Asp
    1190                  1195                  1200
Ile Pro  Met Thr Leu Tyr Glu  Ala Ile Val Arg Asp  Tyr Thr Gly
    1205                  1210                  1215
Arg Thr  Pro Glu Ala Arg Glu  Gln Thr Leu Ile Val  Thr His Leu
    1220                  1225                  1230
Asn Glu  Asp Arg Arg Val Leu  Asn Ser Met Ile His  Asp Ala Arg
    1235                  1240                  1245
Glu Lys  Ala Gly Glu Leu Gly  Lys Glu Gln Val Met  Val Pro Val
    1250                  1255                  1260
Leu Asn  Thr Ala Asn Ile Arg  Asp Gly Glu Leu Arg  Arg Leu Ser
    1265                  1270                  1275
Thr Trp  Glu Lys Asn Pro Asp  Ala Leu Ala Leu Val  Asp Asn Val
    1280                  1285                  1290
Tyr His  Arg Ile Ala Gly Ile  Ser Lys Asp Asp Gly  Leu Ile Thr
    1295                  1300                  1305
Leu Gln  Asp Ala Glu Gly Asn  Thr Arg Leu Ile Ser  Pro Arg Glu
    1310                  1315                  1320
Ala Val  Ala Glu Gly Val Thr  Leu Tyr Thr Pro Asp  Lys Ile Arg
    1325                  1330                  1335
Val Gly  Thr Gly Asp Arg Met  Arg Phe Thr Lys Ser  Asp Arg Glu
    1340                  1345                  1350
```

-continued

```
Arg Gly Tyr Val Ala Asn Ser  Val Trp Thr Val Thr  Ala Val Ser
    1355             1360              1365

Gly Asp Ser Val Thr Leu Ser  Asp Gly Gln Gln Thr  Arg Val Ile
    1370             1375              1380

Arg Pro Gly Gln Glu Arg Ala  Glu Gln His Ile Asp  Leu Ala Tyr
    1385             1390              1395

Ala Ile Thr Ala His Gly Ala  Gln Gly Ala Ser Glu  Thr Phe Ala
    1400             1405              1410

Ile Ala Leu Glu Gly Thr Glu  Gly Asn Arg Lys Leu  Met Ala Gly
    1415             1420              1425

Phe Glu Ser Ala Tyr Val Ala  Leu Ser Arg Met Lys  Gln His Val
    1430             1435              1440

Gln Val Tyr Thr Asp Asn Arg  Gln Gly Trp Thr Asp  Ala Ile Asn
    1445             1450              1455

Asn Ala Val Gln Lys Gly Thr  Ala His Asp Val Leu  Glu Pro Lys
    1460             1465              1470

Pro Asp Arg Glu Val Met Asn  Ala Gln Arg Leu Phe  Ser Thr Ala
    1475             1480              1485

Arg Glu Leu Arg Asp Val Ala  Ala Gly Arg Ala Val  Leu Arg Gln
    1490             1495              1500

Ala Gly Leu Ala Gly Gly Asp  Ser Pro Ala Arg Phe  Ile Ala Pro
    1505             1510              1515

Gly Arg Lys Tyr Pro Gln Pro  Tyr Val Ala Leu Pro  Ala Phe Asp
    1520             1525              1530

Arg Asn Gly Lys Ser Ala Gly  Ile Trp Leu Asn Pro  Leu Thr Thr
    1535             1540              1545

Asp Asp Gly Asn Gly Leu Arg  Gly Phe Ser Gly Glu  Gly Arg Val
    1550             1555              1560

Lys Gly Ser Gly Asp Ala Gln  Phe Val Ala Leu Gln  Gly Ser Arg
    1565             1570              1575

Asn Gly Glu Ser Leu Leu Ala  Asp Asn Met Gln Asp  Gly Val Arg
    1580             1585              1590

Ile Ala Arg Asp Asn Pro Asp  Ser Gly Val Val Val  Arg Ile Ala
    1595             1600              1605

Gly Glu Gly Arg Pro Trp Asn  Pro Gly Ala Ile Thr  Gly Gly Arg
    1610             1615              1620

Val Trp Gly Asp Ile Pro Asp  Asn Ser Val Gln Pro  Gly Ala Gly
    1625             1630              1635

Asn Gly Glu Pro Val Thr Ala  Glu Val Leu Ala Gln  Arg Gln Ala
    1640             1645              1650

Glu Glu Ala Ile Arg Arg Glu  Thr Glu Arg Arg Ala  Asp Glu Ile
    1655             1660              1665

Val Arg Lys Met Ala Glu Asn  Lys Pro Asp Leu Pro  Asp Gly Lys
    1670             1675              1680

Thr Glu Leu Ala Val Arg Asp  Ile Ala Gly Gln Glu  Arg Asp Arg
    1685             1690              1695

Ser Ala Ile Ser Glu Arg Glu  Thr Ala Leu Pro Glu  Ser Val Leu
    1700             1705              1710

Arg Glu Ser Gln Arg Glu Arg  Glu Ala Val Arg Glu  Val Ala Arg
    1715             1720              1725

Glu Asn Leu Leu Gln Glu Arg  Leu Gln Gln Met Glu  Arg Asp Met
    1730             1735              1740
```

-continued

```
Val Arg  Asp Leu Gln Lys Glu  Lys Thr Leu Gly Gly  Asp
   1745              1750                 1755

<210> SEQ ID NO 23
<211> LENGTH: 726
<212> TYPE: PRT
<213> ORGANISM: Methanococcoides burtonii

<400> SEQUENCE: 23

Met Ser Asp Lys Pro Ala Phe Met Lys Tyr Phe Thr Gln Ser Ser Cys
1               5                   10                  15

Tyr Pro Asn Gln Gln Glu Ala Met Asp Arg Ile His Ser Ala Leu Met
                20                  25                  30

Gln Gln Gln Leu Val Leu Phe Glu Gly Ala Cys Gly Thr Gly Lys Thr
            35                  40                  45

Leu Ser Ala Leu Val Pro Ala Leu His Val Gly Lys Met Leu Gly Lys
        50                  55                  60

Thr Val Ile Ile Ala Thr Asn Val His Gln Gln Met Val Gln Phe Ile
65                  70                  75                  80

Asn Glu Ala Arg Asp Ile Lys Lys Val Gln Asp Val Lys Val Ala Val
                85                  90                  95

Ile Lys Gly Lys Thr Ala Met Cys Pro Gln Glu Ala Asp Tyr Glu Glu
                100                 105                 110

Cys Ser Val Lys Arg Glu Asn Thr Phe Glu Leu Met Glu Thr Glu Arg
            115                 120                 125

Glu Ile Tyr Leu Lys Arg Gln Glu Leu Asn Ser Ala Arg Asp Ser Tyr
    130                 135                 140

Lys Lys Ser His Asp Pro Ala Phe Val Thr Leu Arg Asp Glu Leu Ser
145                 150                 155                 160

Lys Glu Ile Asp Ala Val Glu Glu Lys Ala Arg Gly Leu Arg Asp Arg
                165                 170                 175

Ala Cys Asn Asp Leu Tyr Glu Val Leu Arg Ser Asp Ser Glu Lys Phe
                180                 185                 190

Arg Glu Trp Leu Tyr Lys Glu Val Arg Ser Pro Glu Glu Ile Asn Asp
            195                 200                 205

His Ala Ile Lys Asp Gly Met Cys Gly Tyr Glu Leu Val Lys Arg Glu
    210                 215                 220

Leu Lys His Ala Asp Leu Leu Ile Cys Asn Tyr His His Val Leu Asn
225                 230                 235                 240

Pro Asp Ile Phe Ser Thr Val Leu Gly Trp Ile Glu Lys Glu Pro Gln
                245                 250                 255

Glu Thr Ile Val Ile Phe Asp Glu Ala His Asn Leu Glu Ser Ala Ala
            260                 265                 270

Arg Ser His Ser Ser Leu Ser Leu Thr Glu His Ser Ile Glu Lys Ala
        275                 280                 285

Ile Thr Glu Leu Glu Ala Asn Leu Asp Leu Leu Ala Asp Asp Asn Ile
    290                 295                 300

His Asn Leu Phe Asn Ile Phe Leu Glu Val Ile Ser Asp Thr Tyr Asn
305                 310                 315                 320

Ser Arg Phe Lys Phe Gly Glu Arg Glu Arg Val Arg Lys Asn Trp Tyr
                325                 330                 335

Asp Ile Arg Ile Ser Asp Pro Tyr Glu Arg Asn Asp Ile Val Arg Gly
            340                 345                 350

Lys Phe Leu Arg Gln Ala Lys Gly Asp Phe Gly Glu Lys Asp Asp Ile
        355                 360                 365
```

```
Gln Ile Leu Leu Ser Glu Ala Ser Glu Leu Gly Ala Lys Leu Asp Glu
    370                 375                 380

Thr Tyr Arg Asp Gln Tyr Lys Lys Gly Leu Ser Ser Val Met Lys Arg
385                 390                 395                 400

Ser His Ile Arg Tyr Val Ala Asp Phe Met Ser Ala Tyr Ile Glu Leu
                405                 410                 415

Ser His Asn Leu Asn Tyr Tyr Pro Ile Leu Asn Val Arg Arg Asp Met
                420                 425                 430

Asn Asp Glu Ile Tyr Gly Arg Val Glu Leu Phe Thr Cys Ile Pro Lys
            435                 440                 445

Asn Val Thr Glu Pro Leu Phe Asn Ser Leu Phe Ser Val Ile Leu Met
    450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
                485                 490                 495

Lys Arg Leu Ser Ile Ala Val Ser Ile Pro Pro Leu Phe Ala Lys Asn
                500                 505                 510

Arg Asp Asp Arg His Val Thr Glu Leu Leu Glu Gln Val Leu Leu Asp
            515                 520                 525

Ser Ile Glu Asn Ser Lys Gly Asn Val Ile Leu Phe Phe Gln Ser Ala
    530                 535                 540

Phe Glu Ala Lys Arg Tyr Tyr Ser Lys Ile Glu Pro Leu Val Asn Val
545                 550                 555                 560

Pro Val Phe Leu Asp Glu Val Gly Ile Ser Ser Gln Asp Val Arg Glu
                565                 570                 575

Glu Phe Phe Ser Ile Gly Glu Glu Asn Gly Lys Ala Val Leu Leu Ser
                580                 585                 590

Tyr Leu Trp Gly Thr Leu Ser Glu Gly Ile Asp Tyr Arg Asp Gly Arg
        595                 600                 605

Gly Arg Thr Val Ile Ile Ile Gly Val Gly Tyr Pro Ala Leu Asn Asp
    610                 615                 620

Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
                645                 650                 655

Gln Ala Met Gly Arg Val Val Arg Ser Pro Thr Asp Tyr Gly Ala Arg
                660                 665                 670

Ile Leu Leu Asp Gly Arg Phe Leu Thr Asp Ser Lys Lys Arg Phe Gly
            675                 680                 685

Lys Phe Ser Val Phe Glu Val Phe Pro Pro Ala Glu Arg Ser Glu Phe
    690                 695                 700

Val Asp Val Asp Pro Glu Lys Val Lys Tyr Ser Leu Met Asn Phe Phe
705                 710                 715                 720

Met Asp Asn Asp Glu Gln
                725
```

<210> SEQ ID NO 24
<211> LENGTH: 439
<212> TYPE: PRT
<213> ORGANISM: Enterobacteria phage T4

<400> SEQUENCE: 24

```
Met Thr Phe Asp Asp Leu Thr Glu Gly Gln Lys Asn Ala Phe Asn Ile
```

```
1                5                        10                       15

Val Met Lys Ala Ile Lys Glu Lys Lys His His Val Thr Ile Asn Gly
                20                       25                       30

Pro Ala Gly Thr Gly Lys Thr Thr Leu Thr Lys Phe Ile Ile Glu Ala
                35                       40                       45

Leu Ile Ser Thr Gly Glu Thr Gly Ile Ile Leu Ala Ala Pro Thr His
        50                       55                       60

Ala Ala Lys Lys Ile Leu Ser Lys Leu Ser Gly Lys Glu Ala Ser Thr
65                       70                       75                       80

Ile His Ser Ile Leu Lys Ile Asn Pro Val Thr Tyr Glu Glu Asn Val
                85                       90                       95

Leu Phe Glu Gln Lys Glu Val Pro Asp Leu Ala Lys Cys Arg Val Leu
                100                      105                      110

Ile Cys Asp Glu Val Ser Met Tyr Asp Arg Lys Leu Phe Lys Ile Leu
        115                      120                      125

Leu Ser Thr Ile Pro Pro Trp Cys Thr Ile Ile Gly Ile Gly Asp Asn
        130                      135                      140

Lys Gln Ile Arg Pro Val Asp Pro Gly Glu Asn Thr Ala Tyr Ile Ser
145                      150                      155                      160

Pro Phe Phe Thr His Lys Asp Phe Tyr Gln Cys Glu Leu Thr Glu Val
                165                      170                      175

Lys Arg Ser Asn Ala Pro Ile Ile Asp Val Ala Thr Asp Val Arg Asn
                180                      185                      190

Gly Lys Trp Ile Tyr Asp Lys Val Val Asp Gly His Gly Val Arg Gly
                195                      200                      205

Phe Thr Gly Asp Thr Ala Leu Arg Asp Phe Met Val Asn Tyr Phe Ser
        210                      215                      220

Ile Val Lys Ser Leu Asp Asp Leu Phe Glu Asn Arg Val Met Ala Phe
225                      230                      235                      240

Thr Asn Lys Ser Val Asp Lys Leu Asn Ser Ile Ile Arg Lys Lys Ile
                245                      250                      255

Phe Glu Thr Asp Lys Asp Phe Ile Val Gly Glu Ile Ile Val Met Gln
                260                      265                      270

Glu Pro Leu Phe Lys Thr Tyr Lys Ile Asp Gly Lys Pro Val Ser Glu
        275                      280                      285

Ile Ile Phe Asn Asn Gly Gln Leu Val Arg Ile Ile Glu Ala Glu Tyr
        290                      295                      300

Thr Ser Thr Phe Val Lys Ala Arg Gly Val Pro Gly Glu Tyr Leu Ile
305                      310                      315                      320

Arg His Trp Asp Leu Thr Val Glu Thr Tyr Gly Asp Asp Glu Tyr Tyr
                325                      330                      335

Arg Glu Lys Ile Lys Ile Ile Ser Ser Asp Glu Glu Leu Tyr Lys Phe
                340                      345                      350

Asn Leu Phe Leu Gly Lys Thr Ala Glu Thr Tyr Lys Asn Trp Asn Lys
                355                      360                      365

Gly Gly Lys Ala Pro Trp Ser Asp Phe Trp Asp Ala Lys Ser Gln Phe
        370                      375                      380

Ser Lys Val Lys Ala Leu Pro Ala Ser Thr Phe His Lys Ala Gln Gly
385                      390                      395                      400

Met Ser Val Asp Arg Ala Phe Ile Tyr Thr Pro Cys Ile His Tyr Ala
                405                      410                      415

Asp Val Glu Leu Ala Gln Gln Leu Leu Tyr Val Gly Val Thr Arg Gly
                420                      425                      430
```

```
Arg Tyr Asp Val Phe Tyr Val
        435

<210> SEQ ID NO 25
<211> LENGTH: 970
<212> TYPE: PRT
<213> ORGANISM: Clostridium botulinum

<400> SEQUENCE: 25

Met Leu Ser Val Ala Asn Val Arg Ser Pro Ser Ala Ala Ala Ser Tyr
1               5                   10                  15

Phe Ala Ser Asp Asn Tyr Tyr Ala Ser Ala Asp Ala Asp Arg Ser Gly
            20                  25                  30

Gln Trp Ile Gly Asp Gly Ala Lys Arg Leu Gly Leu Glu Gly Lys Val
        35                  40                  45

Glu Ala Arg Ala Phe Asp Ala Leu Leu Arg Gly Glu Leu Pro Asp Gly
    50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
            100                 105                 110

His Trp Ala Glu Lys Asn Ala Ala Glu Thr Arg Val Val Glu Lys Gly
            115                 120                 125

Met Val Val Thr Gln Ala Thr Gly Asn Leu Ala Ile Gly Leu Phe Gln
    130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
            195                 200                 205

Val Leu Lys His Gly Asn Phe Glu Ala Arg Gly Ile Ser Arg Glu Gln
    210                 215                 220

Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
            245                 250                 255

Ser Lys Glu Gly Ile Glu Asp Arg Ala Thr Leu Ser Lys Gln Trp Ser
            260                 265                 270

Glu Ala Ala Gln Ser Ile Gly Leu Asp Leu Lys Pro Leu Val Asp Arg
        275                 280                 285

Ala Arg Thr Lys Ala Leu Gly Gln Gly Met Glu Ala Thr Arg Ile Gly
    290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Ser Val Leu Lys
                325                 330                 335

Gln Asp Arg Gln Thr Ile Ala Ala Ala Gln Ala Val Ala Ser Ala Val
            340                 345                 350

Arg His Leu Ser Gln Arg Glu Ala Ala Phe Glu Arg Thr Ala Leu Tyr
```

-continued

```
            355                 360                 365

Lys Ala Ala Leu Asp Phe Gly Leu Pro Thr Thr Ile Ala Asp Val Glu
    370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu
                405                 410                 415

Gln Arg Ile Leu Ser Glu Val Ala Ala Gly Lys Gly Asp Ser Ser Pro
                420                 425                 430

Ala Ile Thr Pro Gln Lys Ala Ala Ala Ser Val Gln Ala Ala Ala Leu
                435                 440                 445

Thr Gly Gln Gly Phe Arg Leu Asn Glu Gly Gln Leu Ala Ala Ala Arg
    450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
                485                 490                 495

Asp Glu Gly His Pro Val Ile Gly Leu Ala Ile Gln Asn Thr Leu Val
                500                 505                 510

Gln Met Leu Glu Arg Asp Thr Gly Ile Gly Ser Gln Thr Leu Ala Arg
                515                 520                 525

Phe Leu Gly Gly Trp Asn Lys Leu Leu Asp Asp Pro Gly Asn Val Ala
    530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
                580                 585                 590

Lys Gln Leu Gly Ala Val Asp Ala Gly Lys Pro Phe Ala Leu Leu Gln
                595                 600                 605

Arg Ala Gly Ile Ala Arg Ala Glu Met Ala Thr Asn Leu Arg Ala Arg
    610                 615                 620

Asp Pro Val Val Arg Glu Ala Gln Ala Ala Ala Gln Ala Gly Asp Val
625                 630                 635                 640

Arg Lys Ala Leu Arg His Leu Lys Ser His Thr Val Glu Ala Arg Gly
                645                 650                 655

Asp Gly Ala Gln Val Ala Ala Glu Thr Trp Leu Ala Leu Asp Lys Glu
                660                 665                 670

Thr Arg Ala Arg Thr Ser Ile Tyr Ala Ser Gly Arg Ala Ile Arg Ser
    675                 680                 685

Ala Val Asn Ala Ala Val Gln Gln Gly Leu Leu Ala Ser Arg Glu Ile
    690                 695                 700

Gly Pro Ala Lys Met Lys Leu Glu Val Leu Asp Arg Val Asn Thr Thr
705                 710                 715                 720

Arg Glu Glu Leu Arg His Leu Pro Ala Tyr Arg Ala Gly Arg Val Leu
                725                 730                 735

Glu Val Ser Arg Lys Gln Gln Ala Leu Gly Leu Phe Ile Gly Glu Tyr
                740                 745                 750

Arg Val Ile Gly Gln Asp Arg Lys Gly Lys Leu Val Glu Val Glu Asp
                755                 760                 765

Lys Arg Gly Lys Arg Phe Arg Phe Asp Pro Ala Arg Ile Arg Ala Gly
    770                 775                 780
```

```
Lys Gly Asp Asp Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly
                    805                 810                 815

Leu Phe Asn Ala Asp Gln Ala Arg Val Val Glu Ile Ala Asn Gly Lys
                820                 825                 830

Val Thr Phe Glu Thr Ser Lys Gly Asp Leu Val Glu Leu Lys Lys Asp
                835                 840                 845

Asp Pro Met Leu Lys Arg Ile Asp Leu Ala Tyr Ala Leu Asn Val His
        850                 855                 860

Met Ala Gln Gly Leu Thr Ser Asp Arg Gly Ile Ala Val Met Asp Ser
865                 870                 875                 880

Arg Glu Arg Asn Leu Ser Asn Gln Lys Thr Phe Leu Val Thr Val Thr
                885                 890                 895

Arg Leu Arg Asp His Leu Thr Leu Val Val Asp Ser Ala Asp Lys Leu
                900                 905                 910

Gly Ala Ala Val Ala Arg Asn Lys Gly Glu Lys Ala Ser Ala Ile Glu
        915                 920                 925

Val Thr Gly Ser Val Lys Pro Thr Ala Thr Lys Gly Ser Gly Val Asp
        930                 935                 940

Gln Pro Lys Ser Val Glu Ala Asn Lys Ala Glu Lys Glu Leu Thr Arg
945                 950                 955                 960

Ser Lys Ser Lys Thr Leu Asp Phe Gly Ile
                965                 970
```

```
<210> SEQ ID NO 26
<211> LENGTH: 94
<212> TYPE: PRT
<213> ORGANISM: Artificial Sequence
<220> FEATURE:
<223> OTHER INFORMATION: Synthetic polypeptide

<400> SEQUENCE: 26
```

```
Asp Asn Gln Lys Ala Leu Glu Glu Gln Met Asn Ser Ile Asn Ser Val
1                 5                 10                 15

Asn Asp Lys Leu Asn Lys Gly Lys Gly Lys Leu Ser Leu Ser Met Asn
                20                 25                 30

Gly Asn Gln Leu Lys Ala Thr Ser Ser Asn Ala Gly Tyr Gly Ile Ser
        35                 40                 45

Tyr Glu Asp Lys Asn Trp Gly Ile Phe Val Asn Gly Glu Lys Val Tyr
    50                 55                 60

Thr Phe Asn Glu Lys Ser Thr Val Gly Asn Ile Ser Asn Asp Ile Asn
65                 70                 75                 80

Lys Leu Asn Ile Lys Gly Pro Tyr Ile Glu Ile Lys Lys Ile
                85                 90
```

```
<210> SEQ ID NO 27
<211> LENGTH: 549
<212> TYPE: PRT
<213> ORGANISM: Artificial Sequence
<220> FEATURE:
<223> OTHER INFORMATION: Synthetic polypeptide

<400> SEQUENCE: 27
```

```
Ala Thr Gly Gly Gly Thr Cys Thr Gly Gly Ala Thr Ala Ala Cys Gly
1                 5                 10                 15

Ala Ala Cys Thr Gly Ala Gly Cys Cys Thr Gly Gly Thr Thr Gly Ala
```

-continued

```
                20              25              30

Thr Gly Gly Thr Cys Ala Ala Gly Ala Cys Cys Gly Thr Ala Cys Cys
            35              40              45

Cys Thr Gly Ala Cys Cys Gly Thr Cys Cys Ala Ala Cys Ala Ala Thr
        50              55              60

Gly Gly Gly Ala Thr Ala Cys Cys Thr Thr Thr Cys Thr Gly Ala Ala
65              70              75              80

Thr Gly Gly Thr Gly Thr Gly Thr Thr Thr Cys Cys Gly Cys Thr Gly
            85              90              95

Gly Ala Thr Cys Gly Thr Ala Ala Cys Cys Gly Cys Cys Thr Gly Ala
            100             105             110

Cys Cys Cys Gly Thr Gly Ala Ala Thr Gly Gly Thr Thr Cys Cys Ala
        115             120             125

Thr Ala Gly Thr Gly Gly Thr Cys Gly Cys Gly Cys Gly Ala Ala Ala
    130             135             140

Thr Ala Thr Ala Thr Thr Gly Thr Cys Gly Cys Ala Gly Gly Cys Cys
145             150             155             160

Cys Gly Gly Gly Thr Gly Cys Thr Ala Ala Cys Gly Ala Ala Thr Thr
            165             170             175

Thr Ala Gly Ala Gly Gly Thr Ala Cys Gly Cys Thr Gly Gly Ala Ala
            180             185             190

Cys Thr Gly Gly Gly Thr Thr Ala Thr Cys Ala Gly Ala Thr Thr Gly
        195             200             205

Gly Cys Thr Thr Thr Cys Cys Gly Thr Gly Gly Ala Gly Cys Gly Thr
    210             215             220

Thr Gly Gly Cys Ala Thr Cys Ala Ala Cys Thr Thr Cys Thr Cys Thr
225             230             235             240

Thr Ala Cys Ala Cys Cys Ala Cys Gly Cys Cys Gly Ala Ala Cys Ala
            245             250             255

Thr Cys Ala Ala Cys Ala Thr Cys Ala Ala Cys Ala Ala Thr Gly Gly
        260             265             270

Thr Gly Ala Cys Ala Thr Thr Ala Cys Cys Gly Cys Ala Cys Cys Gly
        275             280             285

Cys Cys Gly Thr Thr Thr Gly Gly Cys Cys Thr Gly Ala Ala Cys Thr
    290             295             300

Cys Cys Gly Thr Gly Ala Thr Cys Ala Cys Gly Cys Cys Gly Ala Ala
305             310             315             320

Cys Cys Thr Gly Thr Thr Thr Cys Cys Gly Gly Gly Thr Gly Thr Thr
            325             330             335

Ala Gly Cys Ala Thr Thr Thr Cys Thr Gly Cys Gly Gly Gly Cys Ala
            340             345             350

Ala Cys Gly Gly Thr Cys Cys Gly Gly Gly Cys Ala Thr Cys Cys Gly
        355             360             365

Ala Gly Ala Ala Gly Thr Gly Gly Cys Gly Ala Cys Cys Thr Thr Thr
    370             375             380

Ala Gly Thr Gly Thr Gly Cys Gly Thr Gly Thr Thr Thr Cys Cys Gly
385             390             395             400

Gly Thr Gly Cys Ala Ala Ala Gly Gly Gly Cys Gly Gly Thr Gly Thr
            405             410             415

Cys Gly Cys Ala Gly Thr Gly Ala Gly Cys Ala Ala Thr Gly Cys Ala
            420             425             430

Cys Ala Cys Gly Gly Thr Ala Cys Cys Gly Thr Thr Ala Cys Gly Gly
        435             440             445
```

```
Gly Thr Gly Cys Ala Gly Cys Cys Gly Gly Cys Gly Gly Thr Gly Thr
    450             455             460

Cys Cys Thr Gly Cys Thr Gly Cys Gly Thr Cys Cys Gly Thr Thr Cys
465             470             475             480

Gly Cys Ala Cys Gly Cys Cys Thr Gly Ala Thr Cys Gly Cys Thr Thr
            485             490             495

Cys Ala Ala Cys Cys Gly Gly Thr Gly Ala Thr Thr Cys Gly Gly Thr
            500             505             510

Thr Ala Cys Cys Ala Cys Gly Thr Ala Cys Gly Gly Cys Gly Ala Ala
        515             520             525

Cys Cys Gly Thr Gly Gly Ala Ala Cys Ala Thr Gly Ala Ala Thr Thr
    530             535             540

Ala Ala Thr Gly Ala
545

<210> SEQ ID NO 28
<211> LENGTH: 849
<212> TYPE: PRT
<213> ORGANISM: Artificial Sequence
<220> FEATURE:
<223> OTHER INFORMATION: Synthetic polypeptide

<400> SEQUENCE: 28

Ala Thr Gly Gly Gly Thr Cys Thr Gly Gly Ala Thr Ala Ala Cys Gly
1               5               10              15

Ala Ala Cys Thr Gly Ala Gly Cys Cys Thr Gly Gly Thr Thr Gly Ala
            20              25              30

Thr Gly Gly Thr Cys Ala Ala Gly Ala Cys Cys Gly Thr Ala Cys Cys
        35              40              45

Cys Thr Gly Ala Cys Cys Gly Thr Cys Cys Ala Ala Cys Ala Ala Thr
    50              55              60

Gly Gly Gly Ala Thr Ala Cys Cys Thr Thr Thr Cys Thr Gly Ala Ala
65              70              75              80

Thr Gly Gly Thr Gly Thr Gly Thr Thr Thr Cys Cys Gly Cys Thr Gly
            85              90              95

Gly Ala Thr Cys Gly Thr Ala Ala Cys Cys Gly Cys Cys Thr Gly Ala
        100             105             110

Cys Cys Cys Gly Thr Gly Ala Ala Thr Gly Gly Thr Thr Cys Cys Ala
        115             120             125

Thr Ala Gly Thr Gly Gly Thr Cys Gly Cys Gly Cys Gly Ala Ala Ala
    130             135             140

Thr Ala Thr Ala Thr Thr Gly Thr Cys Gly Cys Ala Gly Gly Cys Cys
145             150             155             160

Cys Gly Gly Gly Thr Gly Cys Thr Ala Ala Cys Gly Ala Ala Thr Thr
            165             170             175

Thr Ala Gly Ala Gly Gly Thr Ala Cys Gly Cys Thr Gly Gly Ala Ala
        180             185             190

Cys Thr Gly Gly Gly Thr Thr Ala Thr Cys Ala Gly Ala Thr Thr Gly
    195             200             205

Gly Cys Thr Thr Thr Cys Cys Gly Thr Gly Gly Ala Gly Cys Gly Thr
    210             215             220

Thr Gly Gly Cys Ala Thr Cys Ala Ala Cys Thr Thr Cys Thr Cys Thr
225             230             235             240

Thr Ala Cys Ala Cys Cys Ala Cys Gly Cys Cys Gly Ala Ala Cys Ala
            245             250             255
```

```
Thr Cys Ala Ala Cys Ala Thr Cys Gly Ala Cys Ala Ala Cys Gly Gly
        260                     265                     270

Thr Gly Ala Cys Ala Thr Cys Ala Cys Cys Gly Cys Ala Cys Cys Gly
        275                     280                     285

Cys Cys Gly Thr Thr Thr Gly Gly Cys Cys Thr Gly Ala Ala Cys Thr
        290                     295                     300

Cys Cys Gly Thr Gly Ala Thr Cys Ala Cys Gly Cys Cys Gly Ala Ala
305                     310                     315                     320

Cys Cys Thr Gly Thr Thr Thr Cys Cys Gly Gly Gly Thr Gly Thr Thr
                325                     330                     335

Ala Gly Cys Ala Thr Thr Thr Cys Thr Gly Cys Gly Gly Gly Cys Ala
                340                     345                     350

Ala Cys Gly Gly Thr Cys Cys Gly Gly Gly Cys Ala Thr Cys Cys Gly
        355                     360                     365

Ala Gly Ala Ala Gly Thr Gly Gly Cys Gly Ala Cys Cys Thr Thr Thr
        370                     375                     380

Ala Gly Thr Gly Thr Gly Cys Gly Thr Gly Thr Thr Thr Cys Cys Gly
385                     390                     395                     400

Gly Thr Gly Cys Ala Ala Ala Gly Gly Gly Cys Gly Gly Thr Gly Thr
                405                     410                     415

Cys Gly Cys Ala Gly Thr Gly Ala Gly Cys Ala Ala Thr Gly Cys Ala
                420                     425                     430

Cys Ala Cys Gly Gly Thr Ala Cys Cys Gly Thr Thr Ala Cys Gly Gly
        435                     440                     445

Gly Thr Gly Cys Ala Gly Cys Cys Gly Gly Cys Gly Gly Thr Gly Thr
        450                     455                     460

Cys Cys Thr Gly Cys Thr Gly Cys Gly Thr Cys Cys Gly Thr Thr Cys
465                     470                     475                     480

Gly Cys Ala Cys Gly Cys Cys Thr Gly Ala Thr Cys Gly Cys Thr Thr
                485                     490                     495

Cys Ala Ala Cys Cys Gly Gly Thr Gly Ala Thr Thr Cys Gly Gly Thr
                500                     505                     510

Thr Ala Cys Cys Ala Cys Gly Thr Ala Cys Gly Gly Cys Gly Ala Ala
                515                     520                     525

Cys Cys Gly Thr Gly Gly Ala Ala Thr Ala Thr Gly Ala Ala Cys Gly
        530                     535                     540

Ala Thr Ala Ala Cys Cys Ala Ala Ala Ala Gly Cys Cys Cys Thr
545                     550                     555                     560

Thr Gly Ala Ala Gly Ala Ala Cys Ala Ala Ala Thr Gly Ala Ala Thr
                565                     570                     575

Ala Gly Thr Ala Thr Cys Ala Ala Cys Ala Gly Cys Gly Thr Gly Ala
                580                     585                     590

Ala Thr Gly Ala Thr Ala Ala Ala Cys Thr Thr Ala Ala Cys Ala Ala
        595                     600                     605

Ala Gly Gly Ala Ala Ala Ala Gly Gly Gly Ala Ala Ala Thr Thr Ala
        610                     615                     620

Thr Cys Thr Cys Thr Thr Thr Cys Ala Ala Thr Gly Ala Ala Thr Gly
625                     630                     635                     640

Gly Ala Ala Ala Thr Cys Ala Ala Cys Thr Thr Ala Ala Ala Gly Cys
                645                     650                     655

Thr Ala Cys Ala Thr Cys Thr Ala Gly Cys Ala Ala Thr Gly Cys Thr
        660                     665                     670
```

```
Gly Gly Thr Thr Ala Thr Gly Gly Thr Ala Thr Cys Ala Gly Thr Thr
        675                 680                 685

Ala Cys Gly Ala Ala Gly Ala Thr Ala Ala Ala Ala Thr Thr Gly
        690                 695                 700

Gly Gly Gly Thr Ala Thr Cys Thr Thr Thr Gly Thr Ala Ala Ala Thr
705                 710                 715                 720

Gly Gly Thr Gly Ala Ala Ala Ala Gly Gly Thr Cys Thr Ala Thr Ala
                725                 730                 735

Cys Thr Thr Thr Thr Ala Ala Thr Gly Ala Ala Ala Ala Thr Cys
                740                 745                 750

Ala Ala Cys Thr Gly Thr Ala Gly Gly Cys Ala Ala Thr Ala Thr Cys
        755                 760                 765

Thr Cys Thr Ala Ala Thr Gly Ala Thr Ala Thr Thr Ala Ala Cys Ala
        770                 775                 780

Ala Ala Thr Thr Ala Ala Ala Cys Ala Thr Thr Ala Ala Ala Gly Gly
785                 790                 795                 800

Ala Cys Cys Thr Thr Ala Thr Ala Thr Thr Gly Ala Gly Ala Thr Thr
                805                 810                 815

Ala Ala Gly Ala Ala Gly Ala Thr Cys Cys Ala Thr Cys Ala Cys Cys
                820                 825                 830

Ala Thr Cys Ala Cys Cys Ala Thr Cys Ala Cys Thr Ala Ala Thr Gly
        835                 840                 845

Ala
```

```
<210> SEQ ID NO 29
<211> LENGTH: 546
<212> TYPE: PRT
<213> ORGANISM: Artificial Sequence
<220> FEATURE:
<223> OTHER INFORMATION: Synthetic polypeptide

<400> SEQUENCE: 29

Ala Thr Gly Gly Gly Thr Cys Thr Gly Gly Ala Thr Ala Ala Cys Gly
1               5                   10                  15

Ala Ala Cys Thr Gly Ala Gly Cys Cys Thr Gly Gly Thr Thr Gly Ala
                20                  25                  30

Thr Gly Gly Thr Cys Ala Ala Gly Ala Cys Cys Gly Thr Ala Cys Cys
        35                  40                  45

Cys Thr Gly Ala Cys Cys Gly Thr Cys Cys Ala Ala Cys Ala Ala Thr
        50                  55                  60

Gly Gly Gly Ala Thr Ala Cys Cys Thr Thr Thr Cys Thr Gly Ala Ala
65                  70                  75                  80

Thr Gly Gly Thr Gly Thr Gly Thr Thr Thr Cys Cys Gly Cys Thr Gly
                85                  90                  95

Gly Ala Thr Cys Gly Thr Ala Ala Cys Cys Gly Cys Cys Thr Gly Ala
                100                 105                 110

Cys Cys Cys Gly Thr Gly Ala Ala Thr Gly Gly Thr Thr Cys Cys Ala
        115                 120                 125

Thr Ala Gly Thr Gly Gly Thr Cys Gly Cys Gly Cys Gly Ala Ala Ala
        130                 135                 140

Thr Ala Thr Ala Thr Thr Gly Thr Cys Gly Cys Ala Gly Gly Cys Cys
145                 150                 155                 160

Cys Gly Gly Gly Thr Gly Cys Thr Ala Ala Cys Gly Ala Ala Thr Thr
                165                 170                 175

Thr Ala Gly Ala Gly Gly Thr Ala Cys Gly Cys Thr Gly Gly Ala Ala
```

-continued

```
                180              185              190
Cys Thr Gly Gly Gly Thr Thr Ala Thr Cys Ala Gly Ala Thr Thr Gly
            195              200              205

Gly Cys Thr Thr Thr Cys Cys Gly Thr Gly Gly Ala Gly Cys Gly Thr
    210              215              220

Thr Gly Gly Cys Ala Thr Cys Ala Ala Cys Thr Thr Cys Thr Cys Thr
225              230              235              240

Thr Ala Cys Ala Cys Cys Ala Cys Gly Cys Cys Gly Ala Ala Cys Ala
            245              250              255

Thr Cys Ala Ala Cys Ala Thr Cys Ala Ala Cys Ala Ala Thr Gly Gly
            260              265              270

Thr Gly Ala Cys Ala Thr Thr Ala Cys Cys Gly Cys Ala Cys Cys Gly
            275              280              285

Cys Cys Gly Thr Thr Thr Gly Gly Cys Cys Thr Gly Ala Ala Cys Thr
    290              295              300

Cys Cys Gly Thr Gly Ala Thr Thr Ala Cys Gly Cys Cys Gly Cys Cys
305              310              315              320

Thr Cys Thr Gly Thr Thr Thr Cys Cys Gly Gly Gly Thr Gly Thr Thr
            325              330              335

Ala Gly Cys Ala Thr Thr Thr Cys Thr Gly Cys Gly Gly Gly Cys Ala
            340              345              350

Ala Cys Gly Gly Thr Cys Cys Gly Gly Gly Cys Ala Thr Cys Cys Gly
            355              360              365

Ala Gly Ala Ala Gly Thr Gly Gly Cys Gly Ala Cys Cys Thr Thr Thr
    370              375              380

Ala Gly Thr Gly Thr Gly Cys Gly Thr Gly Thr Thr Thr Cys Cys Gly
385              390              395              400

Gly Thr Gly Cys Ala Ala Ala Gly Gly Gly Cys Gly Gly Thr Gly Thr
            405              410              415

Cys Gly Cys Ala Gly Thr Gly Ala Gly Cys Ala Ala Thr Gly Cys Ala
            420              425              430

Cys Ala Cys Gly Gly Thr Ala Cys Cys Gly Thr Thr Ala Cys Gly Gly
            435              440              445

Gly Thr Gly Cys Ala Gly Cys Cys Gly Gly Cys Gly Gly Thr Gly Thr
    450              455              460

Cys Cys Thr Gly Cys Thr Gly Cys Gly Thr Cys Cys Gly Thr Thr Cys
465              470              475              480

Gly Cys Ala Cys Gly Cys Cys Thr Gly Ala Thr Cys Gly Cys Thr Thr
            485              490              495

Cys Ala Ala Cys Cys Gly Gly Thr Gly Ala Thr Thr Cys Gly Gly Thr
            500              505              510

Thr Ala Cys Cys Ala Cys Gly Thr Ala Cys Gly Gly Cys Gly Ala Ala
            515              520              525

Cys Cys Gly Thr Gly Gly Ala Ala Cys Ala Thr Gly Ala Ala Thr Thr
    530              535              540

Ala Ala
545
```

<210> SEQ ID NO 30
<211> LENGTH: 849
<212> TYPE: PRT
<213> ORGANISM: Artificial Sequence
<220> FEATURE:
<223> OTHER INFORMATION: Synthetic polypeptide -continued

```
<400> SEQUENCE: 30

Ala Thr Gly Gly Gly Thr Cys Thr Gly Gly Ala Thr Ala Ala Cys Gly
1               5                   10                  15

Ala Ala Cys Thr Gly Ala Gly Cys Cys Thr Gly Gly Thr Thr Gly Ala
                20                  25                  30

Thr Gly Gly Thr Cys Ala Ala Gly Ala Cys Cys Gly Thr Ala Cys Cys
        35                  40                  45

Cys Thr Gly Ala Cys Cys Gly Thr Cys Ala Ala Cys Ala Ala Thr
    50                  55                  60

Gly Gly Gly Ala Thr Ala Cys Cys Thr Thr Thr Cys Thr Gly Ala Ala
65                  70                  75                  80

Thr Gly Gly Thr Gly Thr Gly Thr Thr Cys Cys Gly Cys Thr Gly
        85                  90                  95

Gly Ala Thr Cys Gly Thr Ala Ala Cys Cys Gly Cys Cys Thr Gly Ala
        100                 105                 110

Cys Cys Cys Gly Thr Gly Ala Ala Thr Gly Gly Thr Thr Cys Cys Ala
    115                 120                 125

Thr Ala Gly Thr Gly Gly Thr Cys Gly Cys Gly Cys Gly Ala Ala Ala
    130                 135                 140

Thr Ala Thr Ala Thr Thr Gly Thr Cys Gly Cys Ala Gly Gly Cys Cys
145                 150                 155                 160

Cys Gly Gly Gly Thr Gly Cys Thr Ala Ala Cys Gly Ala Ala Thr Thr
        165                 170                 175

Thr Ala Gly Ala Gly Gly Thr Ala Cys Gly Cys Thr Gly Gly Ala Ala
        180                 185                 190

Cys Thr Gly Gly Gly Thr Thr Ala Thr Cys Ala Gly Ala Thr Thr Gly
        195                 200                 205

Gly Cys Thr Thr Thr Cys Cys Gly Thr Gly Gly Ala Gly Cys Gly Thr
    210                 215                 220

Thr Gly Gly Cys Ala Thr Cys Ala Ala Cys Thr Thr Cys Thr Cys Thr
225                 230                 235                 240

Thr Ala Cys Ala Cys Cys Ala Cys Gly Cys Cys Gly Ala Ala Cys Ala
        245                 250                 255

Thr Cys Ala Ala Cys Ala Thr Cys Gly Ala Cys Ala Ala Cys Gly Gly
        260                 265                 270

Thr Gly Ala Cys Ala Thr Cys Ala Cys Cys Gly Cys Ala Cys Cys Gly
        275                 280                 285

Cys Cys Gly Thr Thr Thr Gly Gly Cys Cys Thr Gly Ala Ala Cys Thr
    290                 295                 300

Cys Cys Gly Thr Gly Ala Thr Thr Ala Cys Gly Cys Cys Gly Cys Cys
305                 310                 315                 320

Thr Cys Thr Gly Thr Thr Thr Cys Cys Gly Gly Gly Thr Gly Thr Thr
        325                 330                 335

Ala Gly Cys Ala Thr Thr Thr Cys Thr Gly Cys Gly Gly Gly Cys Ala
        340                 345                 350

Ala Cys Gly Gly Thr Cys Cys Gly Gly Gly Cys Ala Thr Cys Cys Gly
        355                 360                 365

Ala Gly Ala Ala Gly Thr Gly Gly Cys Gly Ala Cys Cys Thr Thr Thr
    370                 375                 380

Ala Gly Thr Gly Thr Gly Cys Gly Thr Gly Thr Thr Thr Cys Cys Gly
385                 390                 395                 400

Gly Thr Gly Cys Ala Ala Ala Gly Gly Gly Cys Gly Gly Thr Gly Thr
        405                 410                 415
```

-continued

```
Cys Gly Cys Ala Gly Thr Gly Ala Gly Cys Ala Ala Thr Gly Cys Ala
            420                 425                 430

Cys Ala Cys Gly Gly Thr Ala Cys Cys Gly Thr Thr Ala Cys Gly Gly
            435                 440                 445

Gly Thr Gly Cys Ala Gly Cys Cys Gly Gly Cys Gly Gly Thr Gly Thr
            450                 455                 460

Cys Cys Thr Gly Cys Thr Gly Cys Gly Thr Cys Cys Gly Thr Thr Cys
465                 470                 475                 480

Gly Cys Ala Cys Gly Cys Cys Thr Gly Ala Thr Cys Gly Cys Thr Thr
            485                 490                 495

Cys Ala Ala Cys Cys Gly Gly Thr Gly Ala Thr Thr Cys Gly Gly Thr
            500                 505                 510

Thr Ala Cys Cys Ala Cys Gly Thr Ala Cys Gly Gly Cys Gly Ala Ala
            515                 520                 525

Cys Cys Gly Thr Gly Gly Ala Ala Thr Ala Thr Gly Ala Ala Cys Gly
            530                 535                 540

Ala Thr Ala Ala Cys Cys Ala Ala Ala Ala Gly Cys Cys Cys Thr
545                 550                 555                 560

Thr Gly Ala Ala Gly Ala Ala Cys Ala Ala Ala Thr Gly Ala Ala Thr
            565                 570                 575

Ala Gly Thr Ala Thr Cys Ala Ala Cys Ala Gly Cys Gly Thr Gly Ala
            580                 585                 590

Ala Thr Gly Ala Thr Ala Ala Ala Cys Thr Thr Ala Ala Cys Ala Ala
            595                 600                 605

Ala Gly Gly Ala Ala Ala Gly Gly Gly Ala Ala Ala Thr Thr Ala
            610                 615                 620

Thr Cys Thr Cys Thr Thr Thr Cys Ala Ala Thr Gly Ala Ala Thr Gly
625                 630                 635                 640

Gly Ala Ala Ala Thr Cys Ala Ala Cys Thr Thr Ala Ala Ala Gly Cys
            645                 650                 655

Thr Ala Cys Ala Thr Cys Thr Ala Gly Cys Ala Ala Thr Gly Cys Thr
            660                 665                 670

Gly Gly Thr Thr Ala Thr Gly Gly Thr Ala Thr Cys Ala Gly Thr Thr
            675                 680                 685

Ala Cys Gly Ala Ala Gly Ala Thr Ala Ala Ala Ala Thr Thr Gly
            690                 695                 700

Gly Gly Gly Thr Ala Thr Cys Thr Thr Thr Gly Thr Ala Ala Ala Thr
705                 710                 715                 720

Gly Gly Thr Gly Ala Ala Ala Ala Gly Gly Thr Cys Thr Ala Thr Ala
            725                 730                 735

Cys Thr Thr Thr Thr Ala Ala Thr Gly Ala Ala Ala Ala Thr Cys
            740                 745                 750

Ala Ala Cys Thr Gly Thr Ala Gly Gly Cys Ala Ala Thr Ala Thr Cys
            755                 760                 765

Thr Cys Thr Ala Ala Thr Gly Ala Thr Ala Thr Thr Ala Ala Cys Ala
            770                 775                 780

Ala Ala Thr Thr Ala Ala Ala Cys Ala Thr Thr Ala Ala Ala Gly Gly
785                 790                 795                 800

Ala Cys Cys Thr Thr Ala Thr Ala Thr Thr Gly Ala Gly Ala Thr Thr
            805                 810                 815

Ala Ala Gly Ala Ala Gly Ala Thr Cys Cys Ala Thr Cys Ala Cys Cys
            820                 825                 830
```

```
Ala Thr Cys Ala Cys Cys Ala Thr Cys Ala Cys Thr Ala Ala Thr Gly
        835                 840                 845

Ala
```

<210> SEQ ID NO 31
<211> LENGTH: 297
<212> TYPE: PRT
<213> ORGANISM: Eisenia fetida

<400> SEQUENCE: 31

```
Met Ser Ala Lys Ala Ala Glu Gly Tyr Glu Gln Ile Glu Val Asp Val
1               5                  10                  15

Val Ala Val Trp Lys Glu Gly Tyr Val Tyr Glu Asn Arg Gly Ser Thr
            20                  25                  30

Ser Val Asp Gln Lys Ile Thr Ile Thr Lys Gly Met Lys Asn Val Asn
        35                  40                  45

Ser Glu Thr Arg Thr Val Thr Ala Thr His Ser Ile Gly Ser Thr Ile
    50                  55                  60

Ser Thr Gly Asp Ala Phe Glu Ile Gly Ser Val Glu Val Ser Tyr Ser
65                  70                  75                  80

His Ser His Glu Glu Ser Gln Val Ser Met Thr Glu Thr Glu Val Tyr
                85                  90                  95

Glu Ser Lys Val Ile Glu His Thr Ile Thr Ile Pro Pro Thr Ser Lys
            100                 105                 110

Phe Thr Arg Trp Gln Leu Asn Ala Asp Val Gly Gly Ala Asp Ile Glu
        115                 120                 125

Tyr Met Tyr Leu Ile Asp Glu Val Thr Pro Ile Gly Gly Thr Gln Ser
    130                 135                 140

Ile Pro Gln Val Ile Thr Ser Arg Ala Lys Ile Ile Val Gly Arg Gln
145                 150                 155                 160

Ile Ile Leu Gly Lys Thr Glu Ile Arg Ile Lys His Ala Glu Arg Lys
                165                 170                 175

Glu Tyr Met Thr Val Val Ser Arg Lys Ser Trp Pro Ala Ala Thr Leu
            180                 185                 190

Gly His Ser Lys Leu Phe Lys Phe Val Leu Tyr Glu Asp Trp Gly Gly
        195                 200                 205

Phe Arg Ile Lys Thr Leu Asn Thr Met Tyr Ser Gly Tyr Glu Tyr Ala
    210                 215                 220

Tyr Ser Ser Asp Gln Gly Gly Ile Tyr Phe Asp Gln Gly Thr Asp Asn
225                 230                 235                 240

Pro Lys Gln Arg Trp Ala Ile Asn Lys Ser Leu Pro Leu Arg His Gly
                245                 250                 255

Asp Val Val Thr Phe Met Asn Lys Tyr Phe Thr Arg Ser Gly Leu Cys
            260                 265                 270

Tyr Asp Asp Gly Pro Ala Thr Asn Val Tyr Cys Leu Asp Lys Arg Glu
        275                 280                 285

Asp Lys Trp Ile Leu Glu Val Val Gly
    290                 295
```

<210> SEQ ID NO 32
<211> LENGTH: 262
<212> TYPE: PRT
<213> ORGANISM: Escherichia coli

<400> SEQUENCE: 32

```
Cys Leu Thr Ala Pro Pro Lys Glu Ala Ala Arg Pro Thr Leu Met Pro
```

-continued

```
1                 5                    10                   15

Arg Ala Gln Ser Tyr Lys Asp Leu Thr His Leu Pro Ala Pro Thr Gly
            20                  25                  30

Lys Ile Phe Val Ser Val Tyr Asn Ile Gln Asp Glu Thr Gly Gln Phe
            35                  40                  45

Lys Pro Tyr Pro Ala Ser Asn Phe Ser Thr Ala Val Pro Gln Ser Ala
      50                  55                  60

Thr Ala Met Leu Val Thr Ala Leu Lys Asp Ser Arg Trp Phe Ile Pro
65                  70                  75                  80

Leu Glu Arg Gln Gly Leu Gln Asn Leu Leu Asn Glu Arg Lys Ile Ile
                  85                  90                  95

Arg Ala Ala Gln Glu Asn Gly Thr Val Ala Ile Asn Asn Arg Ile Pro
                  100                 105                 110

Leu Gln Ser Leu Thr Ala Ala Asn Ile Met Val Glu Gly Ser Ile Ile
            115                 120                 125

Gly Tyr Glu Ser Asn Val Lys Ser Gly Gly Val Gly Ala Arg Tyr Phe
      130                 135                 140

Gly Ile Gly Ala Asp Thr Gln Tyr Gln Leu Asp Gln Ile Ala Val Asn
145                 150                 155                 160

Leu Arg Val Val Asn Val Ser Thr Gly Glu Ile Leu Ser Ser Val Asn
                  165                 170                 175

Thr Ser Lys Thr Ile Leu Ser Tyr Glu Val Gln Ala Gly Val Phe Arg
                  180                 185                 190

Phe Ile Asp Tyr Gln Arg Leu Leu Glu Gly Glu Val Gly Tyr Thr Ser
            195                 200                 205

Asn Glu Pro Val Met Leu Cys Leu Met Ser Ala Ile Glu Thr Gly Val
      210                 215                 220

Ile Phe Leu Ile Asn Asp Gly Ile Asp Arg Gly Leu Trp Asp Leu Gln
225                 230                 235                 240

Asn Lys Ala Glu Arg Gln Asn Asp Ile Leu Val Lys Tyr Arg His Met
                  245                 250                 255

Ser Val Pro Pro Glu Ser
                  260
```